US012789018B2

(12) United States Patent
Hall et al.

(10) Patent No.: US 12,789,018 B2
(45) Date of Patent: Nov. 10, 2026

(54) ULTRASOUND TRANSDUCER WITH TRANSMIT-RECEIVE CAPABILITY FOR HISTOTRIPSY

(71) Applicant: THE REGENTS OF THE UNIVERSITY OF MICHIGAN, Ann Arbor, MI (US)

(72) Inventors: Timothy Lewis Hall, Ann Arbor, MI (US); Jonathan Robert Sukovich, Ann Arbor, MI (US); Zhen Xu, Ann Arbor, MI (US); Jonathan Jenner Macoskey, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 19/229,825

(22) Filed: Jun. 5, 2025

(65) Prior Publication Data

US 2025/0360344 A1 Nov. 27, 2025

Related U.S. Application Data

(63) Continuation of application No. 18/043,251, filed as application No. PCT/US2021/048008 on Aug. 27, 2021, now Pat. No. 12,343,568.

(Continued)

(51) Int. Cl.
*A61N 7/00* (2006.01)
*B06B 1/02* (2006.01)

(Continued)

(52) U.S. Cl.
CPC .............. *A61N 7/00* (2013.01); *B06B 1/0215* (2013.01); *A61B 2017/22008* (2013.01);

(Continued)

(58) Field of Classification Search
CPC ................................ A61N 7/00; B06B 1/0215

(Continued)

(56) References Cited

U.S. PATENT DOCUMENTS 3,243,497 A 3/1966 Kendall et al.
3,679,021 A 7/1972 Goldberg et al.

(Continued)

FOREIGN PATENT DOCUMENTS

AU 2017222925 B2 11/2021
AU 2021406651 B2 4/2025

(Continued)

OTHER PUBLICATIONS

Allen et al.; Controlling cavitation?based image contrast in focused ultrasound histotripsy surgery; Magnetic resonance in medicine; 73(1); pp. 204-213; Jan. 2015.

(Continued)

*Primary Examiner* — Tomi Skibinski
(74) *Attorney, Agent, or Firm* — Shay Glenn LLP

(57) ABSTRACT

A histotripsy therapy system configured for the treatment of tissue is provided, which may include any number of features. Provided herein are systems and methods that provide efficacious non-invasive and minimally invasive therapeutic, diagnostic and research procedures. In particular, provided herein are optimized systems and methods that provide targeted, efficacious histotripsy in a variety of different regions and under a variety of different conditions without causing undesired tissue damage to intervening/non-target tissues or structures.

16 Claims, 12 Drawing Sheets

Related U.S. Application Data

(60) Provisional application No. 63/071,301, filed on Aug. 27, 2020.

(51) Int. Cl.
*A61B 17/22* (2006.01)
*A61B 17/32* (2006.01)

(52) U.S. Cl.
CPC ............. *A61B 2017/320069* (2017.08); *A61N 2007/0052* (2013.01); *B06B 2201/76* (2013.01)

(58) Field of Classification Search
USPC .......................................................... 327/100
See application file for complete search history.

(56) References Cited

U.S. PATENT DOCUMENTS

| | | | |
|---|---|---|---|
| 3,693,415 | A | 9/1972 | Whittington |
| 3,879,699 | A | 4/1975 | Pepper |
| 4,016,749 | A | 4/1977 | Wachter |
| 4,024,501 | A | 5/1977 | Herring et al. |
| 4,051,394 | A | 9/1977 | Tieden |
| 4,114,457 | A | 9/1978 | Thun |
| 4,117,446 | A | 9/1978 | Alais |
| 4,266,747 | A | 5/1981 | Souder, Jr. et al. |
| 4,269,174 | A | 5/1981 | Adair |
| 4,277,367 | A | 7/1981 | Madsen et al. |
| 4,351,038 | A | 9/1982 | Alais |
| 4,406,153 | A | 9/1983 | Ophir et al. |
| 4,440,025 | A | 4/1984 | Hayakawa et al. |
| 4,447,031 | A | 5/1984 | Souder, Jr. et al. |
| 4,453,408 | A | 6/1984 | Claymar |
| 4,483,343 | A | 11/1984 | Beyer et al. |
| 4,483,345 | A | 11/1984 | Miwa |
| 4,548,374 | A | 10/1985 | Thompson et al. |
| 4,549,533 | A | 10/1985 | Cain et al. |
| 4,550,606 | A | 11/1985 | Drost |
| 4,551,794 | A | 11/1985 | Sandell |
| 4,575,330 | A | 3/1986 | Hull |
| 4,622,972 | A | 11/1986 | Giebeler, Jr. |
| 4,625,731 | A | 12/1986 | Quedens et al. |
| 4,641,378 | A | 2/1987 | McConnell et al. |
| 4,669,483 | A | 6/1987 | Hepp et al. |
| 4,689,986 | A | 9/1987 | Carson et al. |
| 4,757,820 | A | 7/1988 | Itoh |
| 4,791,915 | A | 12/1988 | Barsotti et al. |
| 4,819,621 | A | 4/1989 | Ueberle et al. |
| 4,829,491 | A | 5/1989 | Saugeon et al. |
| 4,856,107 | A | 8/1989 | Dory |
| 4,865,042 | A | 9/1989 | Umemura et al. |
| 4,888,746 | A | 12/1989 | Wurster et al. |
| 4,890,267 | A | 12/1989 | Rudolph |
| 4,922,917 | A | 5/1990 | Dory |
| 4,928,672 | A | 5/1990 | Grasser et al. |
| 4,938,217 | A | 7/1990 | Lele |
| 4,957,099 | A | 9/1990 | Hassler |
| 4,973,980 | A | 11/1990 | Howkins et al. |
| 4,984,575 | A | 1/1991 | Uchiyama et al. |
| 4,991,151 | A | 2/1991 | Dory |
| 4,995,012 | A | 2/1991 | Dory |
| RE33,590 | E | 5/1991 | Dory |
| 5,014,686 | A | 5/1991 | Schafer |
| 5,065,751 | A | 11/1991 | Wolf |
| 5,078,140 | A | 1/1992 | Kwoh |
| 5,080,101 | A | 1/1992 | Dory |
| 5,080,102 | A | 1/1992 | Dory |
| 5,091,893 | A | 2/1992 | Smith et al. |
| 5,092,336 | A | 3/1992 | Fink |
| 5,097,709 | A | 3/1992 | Masuzawa et al. |
| 5,111,822 | A | 5/1992 | Dory |
| 5,143,073 | A | 9/1992 | Dory |
| 5,143,074 | A | 9/1992 | Dory |
| 5,150,711 | A | 9/1992 | Dory |
| 5,158,070 | A | 10/1992 | Dory |
| 5,158,071 | A | 10/1992 | Umemura et al. |
| 5,163,421 | A | 11/1992 | Bernstein et al. |
| 5,165,412 | A | 11/1992 | Okazaki |
| 5,174,294 | A | 12/1992 | Saito et al. |
| 5,195,509 | A | 3/1993 | Rentschler et al. |
| 5,201,314 | A | 4/1993 | Bosley et al. |
| 5,209,221 | A | 5/1993 | Riedlinger |
| 5,215,680 | A | 6/1993 | D'Arrigo |
| 5,219,401 | A | 6/1993 | Cathignol et al. |
| 5,222,806 | A | 6/1993 | Roberts |
| 5,230,340 | A | 7/1993 | Rhyne |
| 5,295,484 | A | 3/1994 | Marcus et al. |
| 5,316,000 | A | 5/1994 | Chapeion et al. |
| 5,354,258 | A | 10/1994 | Dory |
| 5,380,411 | A | 1/1995 | Schlief |
| 5,393,296 | A | 2/1995 | Rattner |
| 5,409,002 | A | 4/1995 | Pell |
| 5,431,621 | A | 7/1995 | Dory |
| 5,435,311 | A | 7/1995 | Umemura et al. |
| 5,443,069 | A | 8/1995 | Schaetzle |
| 5,450,305 | A | 9/1995 | Boys et al. |
| 5,469,852 | A | 11/1995 | Nakamura et al. |
| 5,474,071 | A | 12/1995 | Chapelon et al. |
| 5,474,531 | A | 12/1995 | Carter |
| 5,490,051 | A | 2/1996 | Messana |
| 5,492,126 | A | 2/1996 | Hennige et al. |
| 5,501,655 | A | 3/1996 | Rolt et al. |
| 5,520,188 | A | 5/1996 | Hennige et al. |
| 5,523,058 | A | 6/1996 | Umemura et al. |
| 5,524,620 | A | 6/1996 | Rosenschein |
| 5,524,875 | A | 6/1996 | Thommen, Jr. |
| 5,540,909 | A | 7/1996 | Schutt |
| 5,542,935 | A | 8/1996 | Unger et al. |
| 5,558,092 | A | 9/1996 | Unger et al. |
| 5,563,346 | A | 10/1996 | Bartelt et al. |
| 5,566,675 | A | 10/1996 | Li et al. |
| 5,573,497 | A | 11/1996 | Chapelon |
| 5,580,575 | A | 12/1996 | Unger et al. |
| 5,582,578 | A | 12/1996 | Zhong et al. |
| 5,590,657 | A | 1/1997 | Cain et al. |
| 5,601,526 | A | 2/1997 | Chapeion et al. |
| 5,617,862 | A | 4/1997 | Cole et al. |
| 5,648,098 | A | 7/1997 | Porter |
| 5,665,054 | A | 9/1997 | Dory |
| 5,666,954 | A | 9/1997 | Chapelon et al. |
| 5,676,452 | A | 10/1997 | Scholz |
| 5,676,692 | A | 10/1997 | Sanghvi et al. |
| 5,678,554 | A | 10/1997 | Hossack et al. |
| 5,683,064 | A | 11/1997 | Copeland et al. |
| 5,694,936 | A | 12/1997 | Fujimoto et al. |
| 5,695,460 | A | 12/1997 | Siegel et al. |
| 5,717,657 | A | 2/1998 | Ruffa |
| 5,720,287 | A | 2/1998 | Chapelon et al. |
| 5,724,972 | A | 3/1998 | Petrofsky |
| 5,743,863 | A | 4/1998 | Chapelon |
| 5,753,929 | A | 5/1998 | Bliss |
| 5,759,162 | A | 6/1998 | Oppelt et al. |
| 5,766,138 | A | 6/1998 | Rattner |
| 5,769,790 | A | 6/1998 | Watkins et al. |
| 5,797,848 | A | 8/1998 | Marian et al. |
| 5,800,365 | A | 9/1998 | Zhong et al. |
| 5,820,623 | A | 10/1998 | Ng |
| 5,823,962 | A | 10/1998 | Schaetzle et al. |
| 5,827,204 | A | 10/1998 | Grandia et al. |
| 5,836,896 | A | 11/1998 | Rosenschein |
| 5,849,727 | A | 12/1998 | Porter et al. |
| 5,873,902 | A | 2/1999 | Sanghvi et al. |
| 5,879,314 | A | 3/1999 | Peterson et al. |
| 5,928,169 | A | 7/1999 | Schitzle et al. |
| 5,932,807 | A | 8/1999 | Mallart |
| 5,947,904 | A | 9/1999 | Hossack et al. |
| 6,001,069 | A | 12/1999 | Tachibana et al. |
| 6,007,499 | A | 12/1999 | Martin et al. |
| 6,022,309 | A | 2/2000 | Celliers et al. |
| 6,036,667 | A | 3/2000 | Manna et al. |
| 6,065,166 | A | 5/2000 | Sharrock et al. |
| 6,088,613 | A | 7/2000 | Unger |
| 6,093,883 | A | 7/2000 | Sanghvi et al. |
| 6,113,558 | A | 9/2000 | Rosenschein et al. |

(56) References Cited

U.S. PATENT DOCUMENTS 6,126,607 A 10/2000 Whitmore, III et al.
6,128,958 A 10/2000 Cain
6,143,018 A 11/2000 Beuthan et al.
6,165,144 A 12/2000 Talish et al.
6,176,842 B1 1/2001 Tachibana et al.
6,296,619 B1 10/2001 Brisken et al.
6,308,585 B1 10/2001 Nilsson et al.
6,308,710 B1 10/2001 Silva
6,309,355 B1 10/2001 Cain et al.
6,318,146 B1 11/2001 Madsen et al.
6,321,109 B2 11/2001 Ben-Haim et al.
6,338,566 B1 1/2002 Verdier
6,344,489 B1 2/2002 Spears
6,391,020 B1 5/2002 Kurtz et al.
6,413,216 B1 7/2002 Cain et al.
6,419,648 B1 7/2002 Vitek et al.
6,424,885 B1 7/2002 Niemeyer et al.
6,470,204 B1 10/2002 Uzgiris et al.
6,488,639 B1 12/2002 Ribault et al.
6,490,469 B2 12/2002 Candy
6,500,141 B1 12/2002 Irion et al.
6,506,154 B1 1/2003 Ezion et al.
6,506,171 B1 1/2003 Vitek et al.
6,508,774 B1 1/2003 Acker et al.
6,511,428 B1 1/2003 Azuma et al.
6,511,444 B2 1/2003 Hynynen et al.
6,522,142 B1 2/2003 Freundlich
6,524,251 B2 2/2003 Rabiner et al.
6,536,553 B1 3/2003 Scanlon
6,543,272 B1 4/2003 Vitek
6,556,750 B2 4/2003 Constantino et al.
6,559,644 B2 5/2003 Froundlich et al.
6,576,220 B2 6/2003 Unger
6,599,288 B2 7/2003 Maguire et al.
6,607,498 B2 8/2003 Eshel
6,612,988 B2 9/2003 Maor et al.
6,613,004 B1 9/2003 Vitek et al.
6,613,005 B1 9/2003 Friedman et al.
6,626,854 B2 9/2003 Friedman et al.
6,626,855 B1 9/2003 Weng et al.
6,645,162 B2 11/2003 Friedman et al.
6,648,839 B2 11/2003 Manna et al.
6,666,833 B1 12/2003 Friedman et al.
6,685,640 B1 2/2004 Fry et al.
6,685,657 B2 2/2004 Jones
6,705,994 B2 3/2004 Vortman et al.
6,719,449 B1 4/2004 Laugharn, Jr. et al.
6,719,694 B2 4/2004 Weng et al.
6,735,461 B2 5/2004 Vitek et al.
6,736,814 B2 5/2004 Manna et al.
6,750,463 B1 6/2004 Riley
6,770,031 B2 8/2004 Hynynen et al.
6,773,401 B1 8/2004 Dreschel et al.
6,775,438 B1 8/2004 Gaedke et al.
6,788,977 B2 9/2004 Fenn et al.
6,790,180 B2 9/2004 Vitek
6,820,160 B1 11/2004 Allman
6,852,082 B2 2/2005 Strickberger et al.
6,869,439 B2 3/2005 White et al.
6,890,332 B2 5/2005 Truckai et al.
6,929,609 B2 8/2005 Asafusa
7,004,282 B2 2/2006 Manna et al.
7,059,168 B2 6/2006 Hibi et al.
7,128,711 B2 10/2006 Medan et al.
7,128,719 B2 10/2006 Rosenberg
7,175,596 B2 2/2007 Vitek et al.
7,175,599 B2 2/2007 Hynynen et al.
7,196,313 B2 3/2007 Quinones
7,223,238 B2 5/2007 Swanbom
7,223,239 B2 5/2007 Schulze et al.
7,258,674 B2 8/2007 Cribbs et al.
7,273,458 B2 9/2007 Prausnitz et al.
7,273,459 B2 9/2007 Desilets et al.
7,300,414 B1 11/2007 Holland et al.
7,311,679 B2 12/2007 Desilets et al.
7,331,951 B2 2/2008 Eshel et al.
7,341,569 B2 3/2008 Soltani et al.
7,347,855 B2 3/2008 Eshel et al.
7,358,226 B2 4/2008 Dayton et al.
7,359,640 B2 4/2008 Onde et al.
7,367,948 B2 5/2008 O'Donnell et al.
7,374,551 B2 5/2008 Liang et al.
7,377,900 B2 5/2008 Vitek et al.
7,429,249 B1 9/2008 Winder et al.
7,431,704 B2 10/2008 Babaev
7,442,168 B2 10/2008 Novak et al.
7,462,488 B2 12/2008 Madsen et al.
7,559,905 B2 7/2009 Kagosaki et al.
7,656,638 B2 2/2010 Laakso et al.
7,695,437 B2 4/2010 Quistgaard et al.
7,714,481 B2 5/2010 Sakai
7,771,359 B2 8/2010 Adam
7,967,763 B2 6/2011 Deem et al.
8,057,408 B2 11/2011 Cain et al.
8,295,912 B2 10/2012 Gertner
8,333,115 B1 12/2012 Garvey et al.
8,337,407 B2 12/2012 Quistgaard et al.
8,342,467 B2 1/2013 Stachowski et al.
8,376,970 B2 2/2013 Babaev
8,539,813 B2 9/2013 Cain et al.
8,568,339 B2 10/2013 Rybyanets
8,636,664 B2 1/2014 Brannan
8,715,187 B2 5/2014 Landberg Davis et al.
8,845,537 B2 9/2014 Tanaka et al.
8,932,239 B2 1/2015 Sokka et al.
9,028,434 B2 5/2015 Tanaka
9,049,783 B2 6/2015 Teofilovic
9,061,131 B2 6/2015 Jahnke et al.
9,144,694 B2 9/2015 Cain
9,220,476 B2 12/2015 Coussios et al.
9,220,574 B2 12/2015 Troesken et al.
9,228,730 B1 1/2016 Inbody
9,302,124 B2 4/2016 Konofagou et al.
9,457,201 B2 10/2016 Hoelscher et al.
9,526,923 B2 12/2016 Jahnke et al.
9,636,133 B2 5/2017 Hall et al.
9,642,634 B2 5/2017 Cain et al.
9,763,688 B2 9/2017 Stulen et al.
9,901,753 B2 2/2018 Cain et al.
9,943,708 B2 4/2018 Roberts et al.
10,022,107 B2 7/2018 Thornton et al.
10,046,179 B2 8/2018 Oskar-Kohler
10,046,181 B2 8/2018 Barthe et al.
10,058,352 B2 8/2018 Carvell et al.
10,071,266 B2 9/2018 Cain
10,130,828 B2 11/2018 Vortman et al.
10,219,815 B2 3/2019 Maxwell et al.
10,293,187 B2 5/2019 Cannata et al.
10,293,374 B2 5/2019 Torashima et al.
10,751,015 B2 8/2020 Anderson et al.
10,751,125 B2 8/2020 Levy et al.
10,765,892 B1 9/2020 Vitek et al.
10,772,646 B2 9/2020 Lu et al.
10,780,298 B2 9/2020 Cain et al.
10,791,991 B2 10/2020 Burkett et al.
10,799,209 B2 10/2020 Lahti et al.
10,806,421 B2 10/2020 Keller
10,820,813 B2 11/2020 Alpert
10,847,264 B2 11/2020 Mansker et al.
10,849,511 B2 12/2020 Tochterman et al.
10,869,603 B2 12/2020 Millett et al.
10,869,633 B2 12/2020 Burkett
10,869,648 B2 12/2020 Hubbard et al.
10,874,353 B2 12/2020 Assif
10,874,409 B2 12/2020 Matsubara et al.
10,878,586 B2 12/2020 Brokman et al.
10,888,232 B2 1/2021 Anderson et al.
10,893,808 B2 1/2021 Dorando
10,900,933 B2 1/2021 Prus et al.
10,905,394 B2 2/2021 Stigall et al.
10,912,463 B2 2/2021 Davies et al.
10,925,688 B2 2/2021 Millett et al.
10,927,003 B2 2/2021 Millett et al.
10,932,678 B2 3/2021 Burkett

(56) References Cited

U.S. PATENT DOCUMENTS

| | | | |
|---|---|---|---|
| 10,939,826 | B2 | 3/2021 | Glynn et al. |
| 10,942,022 | B2 | 3/2021 | Johansson et al. |
| 10,973,419 | B2 | 4/2021 | Cort |
| 10,993,618 | B2 | 5/2021 | Mansker et al. |
| 10,993,628 | B2 | 5/2021 | Tochterman |
| 10,993,694 | B2 | 5/2021 | Meyer et al. |
| 11,000,185 | B2 | 5/2021 | Stigall et al. |
| 11,006,840 | B2 | 5/2021 | Stigall |
| 11,013,491 | B2 | 5/2021 | Rice et al. |
| 11,020,087 | B2 | 6/2021 | Hoffman |
| 11,020,089 | B2 | 6/2021 | Corl |
| 11,026,591 | B2 | 6/2021 | Burkett et al. |
| 11,040,140 | B2 | 6/2021 | Unser et al. |
| 11,058,399 | B2 | 7/2021 | Xu et al. |
| 11,071,522 | B2 | 7/2021 | Hynynen et al. |
| 11,103,731 | B2 | 8/2021 | Vortman et al. |
| 11,112,473 | B2 | 9/2021 | Assif |
| 11,119,552 | B2 | 9/2021 | Spencer et al. |
| 11,120,896 | B2 | 9/2021 | Balignasay et al. |
| 11,123,019 | B2 | 9/2021 | Merritt et al. |
| 11,123,575 | B2 | 9/2021 | Vortman et al. |
| 11,135,454 | B2 | 10/2021 | Xu et al. |
| 11,141,063 | B2 | 10/2021 | Kemp et al. |
| 11,141,131 | B2 | 10/2021 | Stigall et al. |
| 11,160,513 | B2 | 11/2021 | Anderson et al. |
| 11,205,507 | B2 | 12/2021 | Anderson et al. |
| 11,219,748 | B2 | 1/2022 | Burkett et al. |
| 11,224,349 | B2 | 1/2022 | Davies et al. |
| 11,224,403 | B2 | 1/2022 | Cor! |
| 11,224,407 | B2 | 1/2022 | Wrolstad et al. |
| 11,234,649 | B2 | 2/2022 | Matsubara et al. |
| 11,246,533 | B2 | 2/2022 | Henderson et al. |
| 11,246,565 | B2 | 2/2022 | Cori |
| 11,253,225 | B2 | 2/2022 | Hancock et al. |
| 11,260,160 | B2 | 3/2022 | Matsubara et al. |
| 11,272,845 | B2 | 3/2022 | Cheline et al. |
| 11,272,904 | B2 | 3/2022 | Vortman et al. |
| 11,291,866 | B2 | 4/2022 | Levy et al. |
| 11,298,030 | B2 | 4/2022 | Davies et al. |
| 11,309,071 | B2 | 4/2022 | Anderson |
| 11,311,271 | B2 | 4/2022 | Stigall et al. |
| 11,324,410 | B2 | 5/2022 | Burkett |
| 11,350,906 | B2 | 6/2022 | Castella et al. |
| 11,350,954 | B2 | 6/2022 | De Cicco et al. |
| 11,364,042 | B2 | 6/2022 | Maxwell et al. |
| 11,369,346 | B2 | 6/2022 | De Cicco et al. |
| 11,369,994 | B2 | 6/2022 | Greenberg et al. |
| 11,395,638 | B2 | 7/2022 | Shin et al. |
| 11,406,334 | B2 | 8/2022 | Merritt |
| 11,406,355 | B2 | 8/2022 | Hoffman et al. |
| 11,406,498 | B2 | 8/2022 | Stigall et al. |
| 11,408,987 | B2 | 8/2022 | Vignon et al. |
| 11,413,017 | B2 | 8/2022 | Stigall et al. |
| 11,419,580 | B2 | 8/2022 | Stigall et al. |
| 11,426,140 | B2 | 8/2022 | Sudol et al. |
| 11,432,795 | B2 | 9/2022 | Merritt |
| 11,432,900 | B2 | 9/2022 | Rakic et al. |
| 11,446,000 | B2 | 9/2022 | Minas et al. |
| 11,452,496 | B2 | 9/2022 | Minas et al. |
| 11,452,506 | B2 | 9/2022 | Perez et al. |
| 11,471,215 | B2 | 10/2022 | Stigall et al. |
| 11,484,294 | B2 | 11/2022 | Hancock et al. |
| 11,510,632 | B2 | 11/2022 | Begin et al. |
| 11,517,291 | B2 | 12/2022 | Kantor et al. |
| 11,520,874 | B2 | 12/2022 | Kennedy et al. |
| 11,527,001 | B2 | 12/2022 | Brokman et al. |
| 11,547,389 | B2 | 1/2023 | Shin et al. |
| 11,553,889 | B2 | 1/2023 | Spencer et al. |
| 11,554,386 | B2 | 1/2023 | Pernot et al. |
| 11,559,207 | B2 | 1/2023 | Stigall et al. |
| 11,567,153 | B2 | 1/2023 | Stormont et al. |
| 11,576,649 | B2 | 2/2023 | Corl |
| 11,576,652 | B2 | 2/2023 | De Cicco et al. |
| 11,583,193 | B2 | 2/2023 | Groenland et al. |
| 11,589,835 | B2 | 2/2023 | Stigall et al. |
| 11,596,351 | B2 | 3/2023 | Nair |
| 11,596,384 | B2 | 3/2023 | Nair et al. |
| 11,596,387 | B2 | 3/2023 | Song |
| 11,596,389 | B2 | 3/2023 | Nair |
| 11,596,469 | B2 | 3/2023 | Nair |
| 11,622,746 | B2 | 4/2023 | Minas et al. |
| 11,638,576 | B2 | 5/2023 | Groenland et al. |
| 11,647,989 | B2 | 5/2023 | Hope Simpson et al. |
| 11,648,424 | B2 | 5/2023 | Cannata et al. |
| 11,653,895 | B2 | 5/2023 | Stigall et al. |
| 11,660,070 | B2 | 5/2023 | Stigall et al. |
| 11,666,245 | B2 | 6/2023 | Rajguru et al. |
| 11,666,307 | B2 | 6/2023 | Unser |
| 11,672,433 | B2 | 6/2023 | Park et al. |
| 11,672,552 | B2 | 6/2023 | Pasquino et al. |
| 11,672,953 | B2 | 6/2023 | May |
| 11,684,342 | B2 | 6/2023 | Groenland et al. |
| 11,684,807 | B2 | 6/2023 | Vortman et al. |
| 11,701,134 | B2 | 7/2023 | Maxwell et al. |
| 11,707,207 | B2 | 7/2023 | Stigall et al. |
| 11,707,254 | B2 | 7/2023 | Di Tullio et al. |
| 11,733,881 | B2 | 8/2023 | Perez |
| 11,737,728 | B2 | 8/2023 | Davies et al. |
| 11,744,527 | B2 | 9/2023 | Scott et al. |
| 11,744,547 | B2 | 9/2023 | Hynynen |
| 11,759,169 | B2 | 9/2023 | Cort |
| 11,759,174 | B2 | 9/2023 | Saroha et al. |
| 11,766,237 | B2 | 9/2023 | Anderson |
| 11,771,370 | B2 | 10/2023 | Hynynen |
| 11,771,405 | B2 | 10/2023 | Rhodes |
| 11,771,869 | B2 | 10/2023 | Cicco |
| 11,779,307 | B2 | 10/2023 | Norris et al. |
| 11,806,167 | B2 | 11/2023 | Burkett |
| 11,813,484 | B2 | 11/2023 | Cannata et al. |
| 11,813,485 | B2 | 11/2023 | Xu et al. |
| 11,819,712 | B2 | 11/2023 | Cain et al. |
| 11,854,687 | B2 | 12/2023 | Keller |
| 11,857,362 | B2 | 1/2024 | Wrolstad et al. |
| 11,857,807 | B2 | 1/2024 | Levy et al. |
| 11,864,918 | B2 | 1/2024 | Burkett et al. |
| 11,872,412 | B2 | 1/2024 | Vortman et al. |
| 11,879,973 | B2 | 1/2024 | Prus et al. |
| 11,883,235 | B2 | 1/2024 | Stigall et al. |
| 11,890,025 | B2 | 2/2024 | Stigall et al. |
| 11,890,136 | B2 | 2/2024 | Stigall et al. |
| 11,890,137 | B2 | 2/2024 | Jenkins et al. |
| 11,950,954 | B2 | 4/2024 | Hyun et al. |
| 11,959,707 | B2 | 4/2024 | Luct et al. |
| 11,963,822 | B2 | 4/2024 | Wrolstad |
| 11,980,778 | B2 | 5/2024 | Cannata et al. |
| 11,986,682 | B2 | 5/2024 | Prus et al. |
| 11,992,366 | B2 | 5/2024 | Stigall et al. |
| 12,035,919 | B2 | 7/2024 | Unser |
| 12,036,066 | B2 | 7/2024 | De Cicco et al. |
| 12,053,194 | B2 | 8/2024 | Goertz et al. |
| 12,082,970 | B2 | 9/2024 | Goodman |
| 12,096,949 | B2 | 9/2024 | Fermi et al. |
| 12,097,072 | B2 | 9/2024 | Stigall et al. |
| 12,112,850 | B2 | 10/2024 | Kuo et al. |
| 12,115,007 | B2 | 10/2024 | Merritt et al. |
| 12,144,677 | B2 | 11/2024 | Corl |
| 12,150,661 | B2 | 11/2024 | Maxwell et al. |
| 12,167,931 | B2 | 12/2024 | iCori |
| 12,178,642 | B2 | 12/2024 | Rajguru et al. |
| 12,178,643 | B2 | 12/2024 | Stigall et al. |
| 12,186,130 | B2 | 1/2025 | Davies |
| 12,220,259 | B2 | 2/2025 | Burkett et al. |
| 12,220,602 | B2 | 2/2025 | Xu et al. |
| 12,232,907 | B2 | 2/2025 | Chao et al. |
| 12,246,195 | B2 | 3/2025 | Levy et al. |
| 12,257,461 | B2 | 3/2025 | Son et al. |
| 12,263,035 | B2 | 4/2025 | Stigall et al. |
| 12,295,600 | B2 | 5/2025 | Stigall et al. |
| 12,303,327 | B2 | 5/2025 | Stigall et al. |
| 12,318,636 | B2 | 6/2025 | Duryea et al. |
| 12,343,198 | B2 | 7/2025 | Laroya |
| 12,350,525 | B2 | 7/2025 | Cain et al. |
| 12,390,665 | B1 | 8/2025 | Duryea et al. |
| 12,402,802 | B2 | 9/2025 | Vitek et al. |

(56) References Cited

U.S. PATENT DOCUMENTS

| | | | |
|---|---|---|---|
| 12,440,188 | B2 | 10/2025 | Chao et al. |
| 12,465,477 | B2 | 11/2025 | Pasquino et al. |
| 12,490,936 | B2 | 12/2025 | Corl |
| 12,558,473 | B2 | 2/2026 | Saroha et al. |
| 12,611,167 | B2 | 4/2026 | Hancock et al. |
| 2001/0039420 | A1 | 11/2001 | Dory |
| 2001/0041163 | A1 | 11/2001 | Sugita |
| 2002/0045890 | A1 | 4/2002 | Celliers et al. |
| 2002/0078964 | A1 | 6/2002 | Kovac et al. |
| 2002/0091315 | A1 | 7/2002 | Spetz |
| 2002/0099356 | A1 | 7/2002 | Unger et al. |
| 2002/0145091 | A1 | 10/2002 | Talish et al. |
| 2003/0092982 | A1 | 5/2003 | Eppstein |
| 2003/0112922 | A1 | 6/2003 | Burdette et al. |
| 2003/0149352 | A1 | 8/2003 | Liang et al. |
| 2003/0157025 | A1 | 8/2003 | Unger et al. |
| 2003/0169591 | A1 | 9/2003 | Cochran |
| 2003/0181833 | A1 | 9/2003 | Faragalla et al. |
| 2003/0199857 | A1 | 10/2003 | Eizenhofer |
| 2003/0221561 | A1 | 12/2003 | Milo |
| 2003/0236539 | A1 | 12/2003 | Rabiner et al. |
| 2004/0127815 | A1 | 7/2004 | Marchitto et al. |
| 2004/0138563 | A1 | 7/2004 | Moehring et al. |
| 2004/0162571 | A1 | 8/2004 | Rabiner et al. |
| 2004/0164213 | A1 | 8/2004 | Stephan |
| 2004/0236248 | A1 | 11/2004 | Svedman |
| 2004/0243021 | A1 | 12/2004 | Murphy et al. |
| 2004/0249509 | A1 | 12/2004 | Rogers et al. |
| 2004/0260214 | A1 | 12/2004 | Echt et al. |
| 2005/0011296 | A1 | 1/2005 | Koseki |
| 2005/0020945 | A1 | 1/2005 | Tosaya et al. |
| 2005/0028289 | A1 | 2/2005 | Hakamiun |
| 2005/0038339 | A1 | 2/2005 | Chauhan et al. |
| 2005/0038361 | A1 | 2/2005 | Zhong et al. |
| 2005/0119572 | A1 | 6/2005 | Angelsen et al. |
| 2005/0121734 | A1 | 6/2005 | Degertekin et al. |
| 2005/0152561 | A1 | 7/2005 | Spencer |
| 2005/0154314 | A1 | 7/2005 | Quistgaard |
| 2005/0154431 | A1 | 7/2005 | Quistgaard et al. |
| 2005/0203399 | A1 | 9/2005 | Vaezy et al. |
| 2005/0215901 | A1 | 9/2005 | Anderson et al. |
| 2005/0234438 | A1 | 10/2005 | Mast et al. |
| 2005/0283098 | A1 | 12/2005 | Conston et al. |
| 2006/0058678 | A1 | 3/2006 | Vitek et al. |
| 2006/0060991 | A1 | 3/2006 | Holsteyns et al. |
| 2006/0074303 | A1 | 4/2006 | Chornenky et al. |
| 2006/0089636 | A1 | 4/2006 | Christopherson et al. |
| 2006/0173321 | A1 | 8/2006 | Kubota et al. |
| 2006/0173387 | A1 | 8/2006 | Hansmann et al. |
| 2006/0184166 | A1 | 8/2006 | Valle et al. |
| 2006/0206028 | A1 | 9/2006 | Lee et al. |
| 2006/0229659 | A1 | 10/2006 | Gifford et al. |
| 2006/0241466 | A1 | 10/2006 | Ottoboni et al. |
| 2006/0241523 | A1 | 10/2006 | Sinelnikov et al. |
| 2006/0241533 | A1 | 10/2006 | Geller |
| 2006/0264760 | A1 | 11/2006 | Liu et al. |
| 2006/0293598 | A1 | 12/2006 | Fraser |
| 2006/0293630 | A1 | 12/2006 | Manna et al. |
| 2007/0004984 | A1 | 1/2007 | Crum et al. |
| 2007/0010805 | A1 | 1/2007 | Fedewa et al. |
| 2007/0016039 | A1 | 1/2007 | Vortman et al. |
| 2007/0044562 | A1 | 3/2007 | Sarr |
| 2007/0065420 | A1 | 3/2007 | Johnson |
| 2007/0083120 | A1 | 4/2007 | Cain et al. |
| 2007/0140413 | A1 | 6/2007 | Saracen |
| 2007/0161902 | A1 | 7/2007 | Dan |
| 2007/0167764 | A1 | 7/2007 | Hynynen |
| 2007/0205785 | A1 | 9/2007 | Nilsson |
| 2007/0219448 | A1 | 9/2007 | Seip et al. |
| 2007/0230757 | A1 | 10/2007 | Trachtenberg et al. |
| 2007/0239001 | A1 | 10/2007 | Mehl et al. |
| 2007/0270683 | A1 | 11/2007 | Meloy |
| 2007/0293762 | A1 | 12/2007 | Sawada et al. |
| 2008/0013593 | A1 | 1/2008 | Kawabata |
| 2008/0033297 | A1 | 2/2008 | Sliwa |
| 2008/0033417 | A1 | 2/2008 | Nields et al. |
| 2008/0051656 | A1 | 2/2008 | Vaezy et al. |
| 2008/0055003 | A1 | 3/2008 | Unnikrishnan et al. |
| 2008/0082026 | A1 | 4/2008 | Schmidt et al. |
| 2008/0091125 | A1 | 4/2008 | Owen et al. |
| 2008/0126665 | A1 | 5/2008 | Burr et al. |
| 2008/0152867 | A1 | 6/2008 | Di Pede |
| 2008/0154132 | A1 | 6/2008 | Hall et al. |
| 2008/0167555 | A1 | 7/2008 | Qian et al. |
| 2008/0177180 | A1 | 7/2008 | Azhari et al. |
| 2008/0183076 | A1 | 7/2008 | Witte et al. |
| 2008/0194965 | A1 | 8/2008 | Sliwa et al. |
| 2008/0214964 | A1 | 9/2008 | Chapelon et al. |
| 2008/0262345 | A1 | 10/2008 | Fichtinger et al. |
| 2008/0262486 | A1 | 10/2008 | Zvuloni et al. |
| 2008/0269614 | A1 | 10/2008 | Adachi et al. |
| 2008/0283303 | A1 | 11/2008 | Cote |
| 2008/0300485 | A1 | 12/2008 | Liu et al. |
| 2008/0312561 | A1 | 12/2008 | Chauhan |
| 2008/0319376 | A1 | 12/2008 | Wilcox et al. |
| 2009/0012514 | A1 | 1/2009 | Moonen et al. |
| 2009/0030339 | A1 | 1/2009 | Cheng et al. |
| 2009/0036773 | A1 | 2/2009 | Lau et al. |
| 2009/0099482 | A1 | 4/2009 | Furuhata et al. |
| 2009/0112098 | A1 | 4/2009 | Vaezy et al. |
| 2009/0171254 | A1 | 7/2009 | Kushculey et al. |
| 2009/0198094 | A1 | 8/2009 | Fenster et al. |
| 2009/0211587 | A1 | 8/2009 | Lawrentschuk |
| 2009/0227874 | A1 | 9/2009 | Suri et al. |
| 2009/0230822 | A1 | 9/2009 | Kushculey et al. |
| 2009/0230823 | A1 | 9/2009 | Kushculey et al. |
| 2009/0254008 | A1 | 10/2009 | Shields, Jr. |
| 2009/0287083 | A1 | 11/2009 | Kushculey et al. |
| 2009/0306502 | A1 | 12/2009 | Lacoste |
| 2010/0011845 | A1 | 1/2010 | Laugham et al. |
| 2010/0042020 | A1 | 2/2010 | Ben-Ezra |
| 2010/0056924 | A1 | 3/2010 | Powers |
| 2010/0059264 | A1 | 3/2010 | Hasegawa et al. |
| 2010/0069797 | A1 | 3/2010 | Cain et al. |
| 2010/0125225 | A1 | 5/2010 | Gelbart et al. |
| 2010/0152624 | A1 | 6/2010 | Tanis et al. |
| 2010/0163694 | A1 | 7/2010 | Fadler et al. |
| 2010/0204578 | A1 | 8/2010 | Schmidt et al. |
| 2010/0210940 | A1 | 8/2010 | Bradley et al. |
| 2010/0241005 | A1 | 9/2010 | Darlington et al. |
| 2010/0251823 | A1 | 10/2010 | Adachi et al. |
| 2010/0255623 | A1 | 10/2010 | Huang |
| 2010/0261994 | A1 | 10/2010 | Davalos et al. |
| 2010/0274136 | A1 | 10/2010 | Cerofolini |
| 2010/0280374 | A1 | 11/2010 | Roberts et al. |
| 2010/0286518 | A1 | 11/2010 | Lee et al. |
| 2010/0286519 | A1 | 11/2010 | Lee et al. |
| 2010/0290856 | A1 | 11/2010 | Zahorec et al. |
| 2010/0298744 | A1 | 11/2010 | Altshuler et al. |
| 2010/0305432 | A1 | 12/2010 | Duhay et al. |
| 2010/0317971 | A1 | 12/2010 | Fan et al. |
| 2010/0318002 | A1 | 12/2010 | Prus et al. |
| 2011/0072970 | A1 | 3/2011 | Slobodzian et al. |
| 2011/0112400 | A1 | 5/2011 | Emery et al. |
| 2011/0118600 | A1 | 5/2011 | Gertner |
| 2011/0118602 | A1 | 5/2011 | Weng et al. |
| 2011/0144490 | A1 | 6/2011 | Davis et al. |
| 2011/0144545 | A1 | 6/2011 | Fan et al. |
| 2011/0172529 | A1 | 7/2011 | Gertner |
| 2011/0178444 | A1 | 7/2011 | Slayton et al. |
| 2011/0208059 | A1 | 8/2011 | Cerofolini |
| 2011/0245671 | A1 | 10/2011 | Sato |
| 2011/0251528 | A1 | 10/2011 | Canney et al. |
| 2011/0257524 | A1 | 10/2011 | Gertner |
| 2011/0257561 | A1 | 10/2011 | Gertner et al. |
| 2011/0263967 | A1 | 10/2011 | Bailey et al. |
| 2011/0270136 | A1 | 11/2011 | Vitek et al. |
| 2011/0302719 | A1 | 12/2011 | Schwirian et al. |
| 2011/0319765 | A1 | 12/2011 | Gertner |
| 2011/0319927 | A1 | 12/2011 | Nita |
| 2012/0010541 | A1* | 1/2012 | Cain ................ A61B 17/22004 601/2 |
| 2012/0029337 | A1 | 2/2012 | Aoyagi |
| 2012/0029353 | A1 | 2/2012 | Slayton et al. |

(56) References Cited

U.S. PATENT DOCUMENTS

2012/0029393 A1 2/2012 Lee
2012/0046592 A1 2/2012 Albright et al.
2012/0059264 A1 3/2012 Hope Simpson et al.
2012/0059285 A1 3/2012 Soltani et al.
2012/0065492 A1 3/2012 Gertner et al.
2012/0065493 A1 3/2012 Gertner
2012/0065494 A1 3/2012 Gertner et al.
2012/0092724 A1 4/2012 Pettis
2012/0101412 A1 4/2012 Vortman et al.
2012/0111339 A1 5/2012 Barthe et al.
2012/0130288 A1 5/2012 Holland et al.
2012/0136279 A1 5/2012 Tanaka et al.
2012/0158013 A1 6/2012 Stefanchik et al.
2012/0172720 A1 7/2012 Asami et al.
2012/0189998 A1 7/2012 Kruecker et al.
2012/0215157 A1 8/2012 Berryman et al.
2012/0232388 A1 9/2012 Curra et al.
2012/0253176 A1 10/2012 Dumoulin
2012/0259250 A1 10/2012 Sapozhnikov et al.
2012/0271167 A1 10/2012 Holland et al.
2012/0271223 A1 10/2012 Khanna
2012/0281902 A1 11/2012 Oikawa et al.
2013/0051178 A1 2/2013 Rybyanets
2013/0053691 A1 2/2013 Kawabata et al.
2013/0090579 A1 4/2013 Cain et al.
2013/0102932 A1 4/2013 Cain et al.
2013/0144165 A1 6/2013 Ebbini et al.
2013/0144194 A1 6/2013 Ahn et al.
2013/0172739 A1 7/2013 Paladini
2013/0190623 A1 7/2013 Bertolina et al.
2013/0190661 A1 7/2013 Wing et al.
2013/0255426 A1 10/2013 Kassow et al.
2013/0257224 A1 10/2013 Wodnicki et al.
2013/0261467 A1 10/2013 Dausch et al.
2013/0267853 A1 10/2013 Dausch et al.
2013/0303906 A1 11/2013 Cain et al.
2013/0338485 A1 12/2013 Mougenot et al.
2014/0005521 A1 1/2014 Kohler et al.
2014/0030806 A1 1/2014 Dudley et al.
2014/0039358 A1 2/2014 Zhou et al.
2014/0046181 A1 2/2014 Benchimol et al.
2014/0058293 A1 2/2014 Hynynen et al.
2014/0058294 A1 2/2014 Gross et al.
2014/0073995 A1 3/2014 Teofilovic et al.
2014/0074076 A1 3/2014 Gertner
2014/0088613 A1 3/2014 Seo et al.
2014/0100459 A1 4/2014 Xu et al.
2014/0112107 A1 4/2014 Guo et al.
2014/0128734 A1 5/2014 Genstier et al.
2014/0180072 A1 6/2014 Davies
2014/0180273 A1 6/2014 Nair
2014/0200489 A1 7/2014 Behar et al.
2014/0243664 A1 8/2014 El-Sayed et al.
2014/0257145 A1 9/2014 Emery
2014/0288428 A1 9/2014 Rothberg et al.
2014/0306126 A1 10/2014 Betrouni et al.
2014/0316269 A1 10/2014 Zhang et al.
2014/0324034 A1 10/2014 Assaf et al.
2014/0330124 A1 11/2014 Carol
2014/0378832 A1 12/2014 Sanghvi et al.
2014/0378964 A1 12/2014 Pearson
2015/0011875 A1 1/2015 Noordhoek et al.
2015/0063668 A1 3/2015 You et al.
2015/0073261 A1 3/2015 Kohler et al.
2015/0080926 A1 3/2015 Emery
2015/0112235 A1 4/2015 Brasset et al.
2015/0148659 A1 5/2015 Vahala
2015/0151141 A1 6/2015 Arnal et al.
2015/0190121 A1 7/2015 Slayton et al.
2015/0190659 A1 7/2015 Kolher
2015/0196239 A1 7/2015 Meehan et al.
2015/0224347 A1 8/2015 Barthe et al.
2015/0257779 A1 9/2015 Sinelnikov et al.
2015/0258352 A1 9/2015 Lin et al.
2015/0265243 A1 9/2015 Kelly
2015/0273246 A1 10/2015 Darlington et al.
2015/0297177 A1 10/2015 Boctor et al.
2015/0305710 A1 10/2015 Stigal et al.
2016/0004933 A1 1/2016 Hu et al.
2016/0038665 A1 2/2016 Schaefer et al.
2016/0114194 A1 4/2016 Gertner
2016/0120572 A1 5/2016 Lee
2016/0135782 A1 5/2016 Chen et al.
2016/0151618 A1 6/2016 Powers et al.
2016/0184614 A1 6/2016 Matula et al.
2016/0206341 A1 7/2016 Slayton
2016/0206867 A1 7/2016 Hossack et al.
2016/0249859 A1 9/2016 Babkin et al.
2016/0287909 A1 10/2016 Maxwell et al.
2016/0303166 A1 10/2016 Katz et al.
2016/0331583 A1 11/2016 Geringer
2016/0331585 A1 11/2016 Kim
2016/0339273 A1 11/2016 Al Mayiah
2016/0345938 A1 12/2016 Tanter et al.
2016/0354087 A1 12/2016 Noonan et al.
2016/0361574 A1 12/2016 Barthe et al.
2017/0000376 A1 1/2017 Partanen et al.
2017/0042521 A1 2/2017 Popovic et al.
2017/0049463 A1 2/2017 Popovic et al.
2017/0071515 A1 3/2017 Chevillet et al.
2017/0072227 A1 3/2017 Khokhlova et al.
2017/0072228 A1 3/2017 Wang et al.
2017/0079519 A1 3/2017 Sung et al.
2017/0100145 A1 4/2017 Khoklova et al.
2017/0120080 A1 5/2017 Phillips et al.
2017/0165046 A1 6/2017 Johnson et al.
2017/0183062 A1 6/2017 Lee
2017/0197099 A1 7/2017 Ruebel et al.
2017/0232277 A1 8/2017 Hall et al.
2017/0263846 A1 9/2017 Nakamura et al.
2017/0281983 A1 10/2017 Marquet et al.
2017/0326589 A1 11/2017 Sudol
2018/0000444 A1 1/2018 Dayton et al.
2018/0008787 A1 1/2018 Schriver et al.
2018/0028841 A1 2/2018 Konofagou et al.
2018/0064412 A1 3/2018 Messas et al.
2018/0161086 A1 6/2018 Davalos et al.
2018/0169444 A1 6/2018 Averkiou et al.
2018/0206816 A1 7/2018 Prus et al.
2018/0207029 A1 7/2018 Herekar et al.
2018/0236271 A1 8/2018 Tanter et al.
2018/0317884 A1 11/2018 Chapelon et al.
2018/0374471 A1 12/2018 Dirksen et al.
2019/0000422 A1 1/2019 West et al.
2019/0023804 A1 1/2019 Onik et al.
2019/0062761 A1 2/2019 Janovjak et al.
2019/0082998 A1 3/2019 Nowroozi et al.
2019/0105113 A1 4/2019 Popovic et al.
2019/0275353 A1 9/2019 Cannata et al.
2019/0282294 A1 9/2019 Davalos et al.
2019/0314045 A1 10/2019 Cunitz et al.
2019/0320904 A1 10/2019 Mei
2019/0323086 A1 10/2019 Leuthardt et al.
2019/0328500 A1 10/2019 Cichon et al.
2020/0010575 A1 1/2020 Hode et al.
2020/0037990 A1 2/2020 Qiao et al.
2020/0055085 A1 2/2020 Taffler
2020/0078608 A1 3/2020 Maxwell et al.
2020/0107843 A1 4/2020 Goertz et al.
2020/0182989 A1 6/2020 Freeman et al.
2020/0194117 A1 6/2020 Krieger et al.
2020/0253550 A1 8/2020 Nair
2020/0254285 A1 8/2020 Jang et al.
2020/0260964 A1 8/2020 Collins et al.
2020/0282239 A1 9/2020 Beder et al.
2020/0289080 A1 9/2020 Yang et al.
2020/0305842 A1 10/2020 Rosenzweig et al.
2020/0308785 A1 10/2020 Sennhauser
2020/0323515 A1 10/2020 Levy
2020/0330039 A1 10/2020 Burkett et al.
2020/0330075 A1 10/2020 O'Reilly et al.
2020/0346044 A1 11/2020 Woodcare et al.
2020/0353293 A1 11/2020 Khokhlova et al.
2020/0367835 A1 11/2020 Anderson

(56) References Cited

U.S. PATENT DOCUMENTS

| | | | |
|---|---|---|---|
| 2020/0375576 | A1 | 12/2020 | Moulton |
| 2020/0405258 | A1 | 12/2020 | Dayton et al. |
| 2020/0405259 | A1 | 12/2020 | Merritt |
| 2021/0000541 | A1 | 1/2021 | Levy et al. |
| 2021/0007759 | A1 | 1/2021 | Jiang et al. |
| 2021/0009936 | A1 | 1/2021 | Kamen et al. |
| 2021/0022703 | A1 | 1/2021 | Nair |
| 2021/0022714 | A1 | 1/2021 | Zagrodsky et al. |
| 2021/0100527 | A1 | 4/2021 | Martin |
| 2021/0108866 | A1 | 4/2021 | Lucht et al. |
| 2021/0121122 | A1 | 4/2021 | Melcher et al. |
| 2021/0161398 | A1 | 6/2021 | Millett et al. |
| 2021/0169515 | A1 | 6/2021 | Pahk et al. |
| 2021/0170204 | A1 | 6/2021 | Vortman et al. |
| 2021/0170205 | A1 | 6/2021 | Vortman et al. |
| 2021/0187331 | A1 | 6/2021 | Zadicario et al. |
| 2021/0196295 | A1 | 7/2021 | Goudot et al. |
| 2021/0220607 | A1 | 7/2021 | Sasamine et al. |
| 2021/0228262 | A1 | 7/2021 | Lennartz et al. |
| 2021/0330294 | A1 | 10/2021 | Hynynen et al. |
| 2021/0339052 | A1 | 11/2021 | Seip et al. |
| 2021/0353161 | A1 | 11/2021 | Merritt et al. |
| 2021/0386451 | A1 | 12/2021 | Escudero et al. |
| 2021/0401366 | A1 | 12/2021 | Weiss et al. |
| 2021/0401400 | A1 | 12/2021 | Sheehan et al. |
| 2022/0008036 | A1 | 1/2022 | Gulsen et al. |
| 2022/0022845 | A1 | 1/2022 | Corl |
| 2022/0031287 | A1 | 2/2022 | Ebbini et al. |
| 2022/0043143 | A1 | 2/2022 | Prus et al. |
| 2022/0059227 | A1 | 2/2022 | Park et al. |
| 2022/0079563 | A1 | 3/2022 | Kemp |
| 2022/0087640 | A1 | 3/2022 | Minas et al. |
| 2022/0110809 | A1 | 4/2022 | Grindstaff et al. |
| 2022/0166462 | A1 | 5/2022 | Deurenberg et al. |
| 2022/0168470 | A1 | 6/2022 | Ricotti et al. |
| 2022/0196771 | A1 | 6/2022 | Zur et al. |
| 2022/0202483 | A1 | 6/2022 | Gertner |
| 2022/0203139 | A1 | 6/2022 | Shapira |
| 2022/0233890 | A1 | 7/2022 | Hynynen et al. |
| 2022/0257329 | A1 | 8/2022 | Stigall et al. |
| 2022/0280233 | A1 | 9/2022 | Park et al. |
| 2022/0280367 | A1 | 9/2022 | Diodato et al. |
| 2022/0296211 | A1 | 9/2022 | Saroha et al. |
| 2022/0331611 | A1 | 10/2022 | Razavi et al. |
| 2022/0338750 | A1 | 10/2022 | Allen et al. |
| 2022/0346756 | A1 | 11/2022 | Chen |
| 2022/0395333 | A1 | 12/2022 | Merritt et al. |
| 2022/0409858 | A1 | 12/2022 | Lin |
| 2023/0000466 | A1 | 1/2023 | Levy et al. |
| 2023/0000469 | A1 | 1/2023 | Prus et al. |
| 2023/0008714 | A1 | 1/2023 | Rajguru et al. |
| 2023/0012365 | A1 | 1/2023 | Alpert et al. |
| 2023/0024998 | A1 | 1/2023 | Greenberg |
| 2023/0037603 | A1 | 2/2023 | Pombo et al. |
| 2023/0038498 | A1 | 2/2023 | Xu et al. |
| 2023/0038543 | A1 | 2/2023 | Minas et al. |
| 2023/0042834 | A1 | 2/2023 | Henderson et al. |
| 2023/0045488 | A1 | 2/2023 | Rajguru et al. |
| 2023/0048979 | A1 | 2/2023 | Lindenmoyer et al. |
| 2023/0061534 | A1 | 3/2023 | Stopek |
| 2023/0073447 | A1 | 3/2023 | Minas et al. |
| 2023/0100912 | A1 | 3/2023 | Amar et al. |
| 2023/0112722 | A1 | 4/2023 | Hoffman et al. |
| 2023/0114972 | A1 | 4/2023 | Bigham et al. |
| 2023/0210603 | A1 | 7/2023 | Barrera et al. |
| 2023/0218930 | A1 | 7/2023 | Stopek et al. |
| 2023/0240615 | A1 | 8/2023 | May et al. |
| 2023/0240663 | A1 | 8/2023 | Lafond et al. |
| 2023/0240792 | A1 | 8/2023 | Rakic et al. |
| 2023/0270388 | A1 | 8/2023 | Richardson et al. |
| 2023/0310899 | A1 | 10/2023 | Hall et al. |
| 2023/0310900 | A1 | 10/2023 | Cannata et al. |
| 2023/0329559 | A1 | 10/2023 | Xu et al. |
| 2023/0338010 | A1 | 10/2023 | Sturm |
| 2023/0372025 | A1 | 11/2023 | Van der Zaag et al. |
| 2023/0389891 | A1 | 12/2023 | Cohen et al. |
| 2023/0398381 | A1 | 12/2023 | Vitek et al. |
| 2024/0000422 | A1 | 1/2024 | Cort |
| 2024/0000426 | A1 | 1/2024 | Davies et al. |
| 2024/0001157 | A1 | 1/2024 | Cannata et al. |
| 2024/0001158 | A1 | 1/2024 | Cannata et al. |
| 2024/0023928 | A1 | 1/2024 | Di Tullio et al. |
| 2024/0023930 | A1 | 1/2024 | Anderson |
| 2024/0023941 | A1 | 1/2024 | Rhodes |
| 2024/0024705 | A1 | 1/2024 | Xu et al. |
| 2024/0065632 | A1 | 2/2024 | Burkett |
| 2024/0138807 | A1 | 5/2024 | Minas |
| 2024/0139553 | A1 | 5/2024 | Miller et al. |
| 2024/0149078 | A1 | 5/2024 | Duryea et al. |
| 2024/0165666 | A1 | 5/2024 | Hynynen et al. |
| 2024/0188929 | A1 | 6/2024 | Minas et al. |
| 2024/0188931 | A1 | 6/2024 | Ossmann et al. |
| 2024/0189267 | A1 | 6/2024 | Strupp |
| 2024/0189628 | A1 | 6/2024 | Grumbir et al. |
| 2024/0207654 | A1 | 6/2024 | Xu et al. |
| 2024/0225592 | A1 | 7/2024 | May et al. |
| 2024/0245374 | A1 | 7/2024 | Jenkins et al. |
| 2024/0245390 | A1 | 7/2024 | Winkler Brown et al. |
| 2024/0245465 | A1 | 7/2024 | Jenkins et al. |
| 2024/0269491 | A1 | 8/2024 | Xu et al. |
| 2024/0285249 | A1 | 8/2024 | May |
| 2024/0285978 | A1 | 8/2024 | Xu et al. |
| 2024/0299092 | A1 | 9/2024 | Boinagrov et al. |
| 2024/0307027 | A1 | 9/2024 | Minas |
| 2024/0307708 | A1 | 9/2024 | Cannata et al. |
| 2024/0315713 | A1 | 9/2024 | Maxwell et al. |
| 2024/0316367 | A1 | 9/2024 | Cannata et al. |
| 2024/0335680 | A1 | 10/2024 | Achrol et al. |
| 2024/0341732 | A1 | 10/2024 | Hoffman et al. |
| 2024/0350118 | A1 | 10/2024 | Jenkins et al. |
| 2024/0350153 | A1 | 10/2024 | Cannata et al. |
| 2024/0350207 | A1 | 10/2024 | Stopek |
| 2024/0374242 | A1 | 11/2024 | Merritt et al. |
| 2024/0399174 | A1 | 12/2024 | Cannata et al. |
| 2024/0408416 | A1 | 12/2024 | Cannata et al. |
| 2025/0072872 | A1 | 3/2025 | Nachtomy et al. |
| 2025/0090130 | A1 | 3/2025 | Schell et al. |
| 2025/0090871 | A1 | 3/2025 | Snell et al. |
| 2025/0128096 | A1 | 4/2025 | Miller et al. |
| 2025/0152135 | A1 | 5/2025 | Shaffer et al. |
| 2025/0186808 | A1 | 6/2025 | Cannata et al. |
| 2025/0249289 | A1 | 8/2025 | Miller et al. |
| 2025/0256132 | A1 | 8/2025 | Xu et al. |
| 2025/0349023 | A1 | 11/2025 | Rajguru et al. |
| 2025/0352828 | A1 | 11/2025 | Miller et al. |
| 2025/0352831 | A1 | 11/2025 | Cannata et al. |
| 2026/0115496 | A1 | 4/2026 | Rootes et al. |

FOREIGN PATENT DOCUMENTS

| | | | |
|---|---|---|---|
| AU | 2022215411 | B2 | 5/2025 |
| BR | 112018017326 | B1 | 12/2022 |
| CA | 3073552 | A1 | 3/2019 |
| CA | 3101381 | A1 | 11/2019 |
| CA | 3055856 | A1 | 4/2020 |
| CA | 3130859 | A1 | 10/2020 |
| CA | 3153080 | A1 | 4/2021 |
| CA | 2910561 | C | 7/2021 |
| CA | 2908740 | C | 10/2021 |
| CA | 2980976 | C | 3/2023 |
| CA | 2840014 | C | 8/2023 |
| CN | 1669672 | A | 9/2005 |
| CN | 1732031 | A | 2/2006 |
| CN | 201197744 | Y | 2/2009 |
| CN | 102292123 | A | 12/2011 |
| CN | 102481164 | A | 5/2012 |
| CN | 102665585 | A | 9/2012 |
| CN | 102740777 | A | 10/2012 |
| CN | 103537016 | A | 1/2014 |
| CN | 103648361 | A | 3/2014 |
| CN | 103812477 | A | 5/2014 |
| CN | 104013444 | A | 9/2014 |
| CN | 104135938 | A | 11/2014 |
| CN | 104208822 | A | 12/2014 |

(56) References Cited

FOREIGN PATENT DOCUMENTS

| | | | |
|---|---|---|---|
| CN | 106999076 | B | 8/2017 |
| CN | 109185113 | A | 1/2019 |
| CN | 109689160 | A | 4/2019 |
| CN | 208725992 | U | 4/2019 |
| CN | 111565642 | A | 8/2020 |
| CN | 111655337 | A | 9/2020 |
| CN | 111699022 | A | 9/2020 |
| CN | 111712300 | A | 9/2020 |
| CN | 111712301 | A | 9/2020 |
| CN | 106999053 | B | 10/2020 |
| CN | 107660137 | B | 10/2020 |
| CN | 111757769 | A | 10/2020 |
| CN | 112204412 | A | 1/2021 |
| CN | 112236195 | A | 1/2021 |
| CN | 106661535 | B | 3/2021 |
| CN | 112533673 | A | 3/2021 |
| CN | 112566694 | A | 3/2021 |
| CN | 106999054 | B | 5/2021 |
| CN | 106793997 | B | 6/2021 |
| CN | 107530049 | B | 6/2021 |
| CN | 112912011 | A | 6/2021 |
| CN | 112912012 | A | 6/2021 |
| CN | 112912013 | A | 6/2021 |
| CN | 112969413 | A | 6/2021 |
| CN | 112996445 | A | 6/2021 |
| CN | 113167877 | A | 7/2021 |
| CN | 113196080 | A | 7/2021 |
| CN | 109196369 | B | 8/2021 |
| CN | 109200484 | B | 8/2021 |
| CN | 113316419 | A | 8/2021 |
| CN | 113329788 | A | 8/2021 |
| CN | 109640830 | B | 10/2021 |
| CN | 113473917 | A | 10/2021 |
| CN | 113507946 | A | 10/2021 |
| CN | 113518588 | A | 10/2021 |
| CN | 113705586 | A | 11/2021 |
| CN | 110662575 | B | 12/2021 |
| CN | 113905666 | A | 1/2022 |
| CN | 114222536 | A | 3/2022 |
| CN | 114423362 | A | 4/2022 |
| CN | 110248606 | B | 6/2022 |
| CN | 115227992 | A | 10/2022 |
| CN | 109843181 | B | 11/2022 |
| CN | 115461000 | A | 12/2022 |
| CN | 115515504 | A | 12/2022 |
| CN | 109091768 | B | 3/2023 |
| CN | 115779285 | A | 3/2023 |
| CN | 115779287 | A | 3/2023 |
| CN | 115813438 | A | 3/2023 |
| CN | 111032157 | B | 4/2023 |
| CN | 115916035 | A | 4/2023 |
| CN | 110958858 | B | 5/2023 |
| CN | 116172611 | A | 5/2023 |
| CN | 111655337 | B | 6/2023 |
| CN | 109416908 | B | 7/2023 |
| CN | 107529989 | B | 8/2023 |
| CN | 111372522 | B | 8/2023 |
| CN | 116617589 | A | 8/2023 |
| CN | 112236195 | B | 9/2023 |
| CN | 114555247 | B | 9/2023 |
| CN | 109416907 | B | 10/2023 |
| CN | 117321444 | A | 12/2023 |
| CN | 117500437 | A | 2/2024 |
| CN | 117580499 | A | 2/2024 |
| CN | 111212606 | B | 3/2024 |
| CN | 113490459 | B | 5/2024 |
| CN | 112601498 | B | 9/2024 |
| CN | 113271866 | B | 10/2024 |
| CN | 112603273 | B | 12/2024 |
| CN | 112639754 | B | 12/2024 |
| CN | 119367006 | A | 1/2025 |
| CN | 112704620 | B | 2/2025 |
| CN | 110410498 | B | 3/2025 |
| CN | 112426634 | B | 3/2025 |
| CN | 112545816 | B | 5/2025 |
| CN | 112546464 | B | 6/2025 |
| CN | 112618971 | B | 6/2025 |
| CN | 113040905 | B | 6/2025 |
| CN | 114340682 | B | 7/2025 |
| CN | 115515567 | B | 7/2025 |
| CN | 112546465 | B | 8/2025 |
| CN | 309464789 | S | 8/2025 |
| CN | 111991712 | B | 9/2025 |
| CN | 112494106 | B | 10/2025 |
| CN | 111388117 | B | 2/2026 |
| CN | 111388121 | B | 2/2026 |
| DE | 3220751 | A1 | 12/1983 |
| DE | 3544628 | A1 | 6/1987 |
| DE | 3817094 | A1 | 11/1989 |
| DE | 4012760 | A1 | 5/1992 |
| DE | 602020055151 | T2 | 7/2025 |
| DE | 602020058523 | T2 | 9/2025 |
| DE | 602020059056 | T2 | 9/2025 |
| DE | 602017092008 | T2 | 10/2025 |
| EP | 0017382 | A1 | 10/1980 |
| EP | 0320303 | A2 | 6/1989 |
| EP | 0332871 | A2 | 9/1989 |
| EP | 0384831 | A2 | 8/1990 |
| EP | 0619156 | A1 | 10/1994 |
| EP | 0755653 | A1 | 1/1997 |
| EP | 1374785 | A1 | 1/2004 |
| EP | 1504713 | A1 | 2/2005 |
| EP | 1566201 | A2 | 8/2005 |
| EP | 2397188 | A1 | 12/2011 |
| EP | 2934308 | B1 | 10/2015 |
| EP | 2934309 | B1 | 10/2015 |
| EP | 3097180 | B1 | 11/2016 |
| EP | 3100767 | B1 | 11/2019 |
| EP | 2759003 | B1 | 8/2020 |
| EP | 3558457 | A4 | 8/2020 |
| EP | 3700629 | A1 | 9/2020 |
| EP | 3218829 | B1 | 10/2020 |
| EP | 3229688 | B1 | 10/2020 |
| EP | 2887989 | B1 | 2/2021 |
| EP | 3777689 | A1 | 2/2021 |
| EP | 2938253 | B1 | 3/2021 |
| EP | 3076864 | B1 | 3/2021 |
| EP | 2802276 | B1 | 4/2021 |
| EP | 2809221 | B1 | 4/2021 |
| EP | 3801761 | A1 | 4/2021 |
| EP | 3801762 | A2 | 4/2021 |
| EP | 3801763 | A1 | 4/2021 |
| EP | 296736981 | | 5/2021 |
| EP | 2967488 | B1 | 6/2021 |
| EP | 3184048 | B1 | 6/2021 |
| EP | 3482390 | B1 | 9/2021 |
| EP | 3870067 | A1 | 9/2021 |
| EP | 3870069 | A1 | 9/2021 |
| EP | 3876843 | A1 | 9/2021 |
| EP | 296737081 | | 9/2021 |
| EP | 2931130 | B1 | 10/2021 |
| EP | 2934304 | B1 | 10/2021 |
| EP | 3887843 | A1 | 10/2021 |
| EP | 3888534 | A1 | 10/2021 |
| EP | 3895604 | A1 | 10/2021 |
| EP | 3897391 | A1 | 10/2021 |
| EP | 3229672 | B1 | 11/2021 |
| EP | 3902603 | A1 | 11/2021 |
| EP | 3903672 | A1 | 11/2021 |
| EP | 2964096 | B1 | 12/2021 |
| EP | 3930776 | A1 | 1/2022 |
| EP | 3545829 | B1 | 3/2022 |
| EP | 3959530 | A2 | 3/2022 |
| EP | 3060129 | B1 | 4/2022 |
| EP | 3986296 | A1 | 4/2022 |
| EP | 3988167 | A1 | 4/2022 |
| EP | 2914166 | B1 | 5/2022 |
| EP | 3229674 | B1 | 5/2022 |
| EP | 2779907 | B1 | 6/2022 |
| EP | 3102098 | B1 | 6/2022 |
| EP | 2965263 | B1 | 7/2022 |
| EP | 2726152 | B1 | 8/2022 |
| EP | 4042936 | A1 | 8/2022 |
| EP | 3298959 | B2 | 9/2022 |

(56) References Cited

FOREIGN PATENT DOCUMENTS

| | | | |
|---|---|---|---|
| EP | 2938268 | B1 | 11/2022 |
| EP | 3581103 | B1 | 11/2022 |
| EP | 4087492 | A1 | 11/2022 |
| EP | 4093470 | A1 | 11/2022 |
| EP | 293113181 | | 11/2022 |
| EP | 3091905 | B1 | 12/2022 |
| EP | 4098203 | A1 | 12/2022 |
| EP | 3057496 | B1 | 1/2023 |
| EP | 4114274 | A1 | 1/2023 |
| EP | 4117534 | A1 | 1/2023 |
| EP | 295073781 | | 1/2023 |
| EP | 2938265 | B1 | 2/2023 |
| EP | 286980481 | | 2/2023 |
| EP | 3024403 | B1 | 3/2023 |
| EP | 4138672 | A1 | 3/2023 |
| EP | 4151156 | A1 | 3/2023 |
| EP | 4161360 | A1 | 4/2023 |
| EP | 293827181 | | 4/2023 |
| EP | 4179995 | A2 | 5/2023 |
| EP | 3171764 | B1 | 6/2023 |
| EP | 3229695 | B1 | 7/2023 |
| EP | 293113281 | | 7/2023 |
| EP | 4226864 | A1 | 8/2023 |
| EP | 4230121 | A2 | 8/2023 |
| EP | 4230146 | A1 | 8/2023 |
| EP | 4233972 | A2 | 8/2023 |
| EP | 3870069 | B1 | 9/2023 |
| EP | 286673381 | | 9/2023 |
| EP | 3658037 | B1 | 10/2023 |
| EP | 3870070 | B1 | 10/2023 |
| EP | 4257151 | A1 | 10/2023 |
| EP | 348437181 | | 10/2023 |
| EP | 368587481 | | 10/2023 |
| EP | 2938255 | B1 | 11/2023 |
| EP | 3229906 | B1 | 11/2023 |
| EP | 3903672 | B1 | 11/2023 |
| EP | 4272654 | A2 | 11/2023 |
| EP | 4275609 | A2 | 11/2023 |
| EP | 376491481 | | 11/2023 |
| EP | 3316804 | B1 | 12/2023 |
| EP | 351910981 | | 12/2023 |
| EP | 3166479 | B1 | 1/2024 |
| EP | 3537984 | B1 | 1/2024 |
| EP | 3908195 | B1 | 2/2024 |
| EP | 3182920 | B1 | 3/2024 |
| EP | 3174643 | B1 | 4/2024 |
| EP | 3814917 | B1 | 4/2024 |
| EP | 3681419 | B1 | 5/2024 |
| EP | 4368118 | A2 | 5/2024 |
| EP | 2804525 | B1 | 6/2024 |
| EP | 4380667 | A2 | 6/2024 |
| EP | 3324836 | B1 | 9/2024 |
| EP | 362473281 | | 11/2024 |
| EP | 4289415 | A4 | 1/2025 |
| EP | 3190958 | B1 | 2/2025 |
| EP | 3277378 | B1 | 5/2025 |
| EP | 4041463 | B1 | 8/2025 |
| EP | 3986296 | B1 | 9/2025 |
| ES | 2774069 | T3 | 7/2020 |
| ES | 2819552 | T3 | 4/2021 |
| ES | 2829822 | T3 | 6/2021 |
| ES | 2998435 | T3 | 2/2025 |
| ES | 3005837 | T3 | 3/2025 |
| GB | 2099582 | A | 12/1982 |
| HK | 1245715 | B | 1/2021 |
| IL | 254768 | A | 5/2021 |
| IL | 261285 | B | 2/2022 |
| IN | 202117039853 | A | 12/2021 |
| IN | 387413 | B | 1/2022 |
| IN | 445766 | B | 8/2023 |
| JP | 60-80779 | A | 5/1985 |
| JP | 61-196718 | A | 8/1986 |
| JP | S62144641 | A | 6/1987 |
| JP | S6468249 | A | 3/1989 |
| JP | H02104343 | A | 4/1990 |
| JP | 02-215451 | A | 8/1990 |
| JP | H02246961 | A | 10/1990 |
| JP | H0422351 | A | 1/1992 |
| JP | 06-197907 | A | 7/1994 |
| JP | 07-504339 | A | 5/1995 |
| JP | H07213527 | A | 8/1995 |
| JP | H07284499 | A | 10/1995 |
| JP | 08-84740 | A | 4/1996 |
| JP | 06-304178 | A | 5/1996 |
| JP | 08-131454 | A | 5/1996 |
| JP | 09-55571 | A | 2/1997 |
| JP | H10305041 | A | 11/1998 |
| JP | 10-512477 | A | 12/1998 |
| JP | 2000300559 | A | 10/2000 |
| JP | 2003510159 | A | 3/2003 |
| JP | 2004505660 | A | 2/2004 |
| JP | 2004249106 | A | 9/2004 |
| JP | 2005167058 | A | 6/2005 |
| JP | 2006511265 | A | 4/2006 |
| JP | 2007144225 | A | 6/2007 |
| JP | 2007520307 | A | 7/2007 |
| JP | 2008049199 | A | 3/2008 |
| JP | 2010019554 | A | 1/2010 |
| JP | 2010029650 | A | 2/2010 |
| JP | 2010204068 | A | 9/2010 |
| JP | 2013538097 | A | 10/2013 |
| JP | 2004512502 | A | 4/2014 |
| JP | 2014204876 | A | 10/2014 |
| JP | 2015002983 | A | 1/2015 |
| JP | 2015519970 | A | 7/2015 |
| JP | 2016508808 | A | 3/2016 |
| JP | 2017/506542 | A | 3/2017 |
| JP | 2017506538 | A | 3/2017 |
| JP | 2019051295 | A | 4/2019 |
| JP | 2020525167 | A | 8/2020 |
| JP | 2020525168 | A | 8/2020 |
| JP | 2020525169 | A | 8/2020 |
| JP | 6785554 | B2 | 10/2020 |
| JP | 6789944 | B2 | 11/2020 |
| JP | 2020534077 | A | 11/2020 |
| JP | 2020195788 | A | 12/2020 |
| JP | 2020535895 | A | 12/2020 |
| JP | 6832958 | B2 | 2/2021 |
| JP | 6835719 | B2 | 2/2021 |
| JP | 6838057 | B2 | 3/2021 |
| JP | 6849592 | B2 | 3/2021 |
| JP | 2021510104 | A | 4/2021 |
| JP | 6896719 | B2 | 6/2021 |
| JP | 6934933 | B2 | 9/2021 |
| JP | 6951560 | B2 | 10/2021 |
| JP | 6979633 | B2 | 12/2021 |
| JP | 6980696 | B2 | 12/2021 |
| JP | 7012726 | B2 | 1/2022 |
| JP | 2022500092 | A | 1/2022 |
| JP | 2022500093 | A | 1/2022 |
| JP | 2022501080 | A | 1/2022 |
| JP | 2022504159 | A | 1/2022 |
| JP | 2022509389 | A | 1/2022 |
| JP | 2022509391 | A | 1/2022 |
| JP | 2022509392 | A | 1/2022 |
| JP | 2022509393 | A | 1/2022 |
| JP | 2022509395 | A | 1/2022 |
| JP | 2022509401 | A | 1/2022 |
| JP | 2022509453 | A | 1/2022 |
| JP | 2022510217 | A | 1/2022 |
| JP | 7019679 | B2 | 2/2022 |
| JP | 7026118 | B2 | 2/2022 |
| JP | 2022514272 | A | 2/2022 |
| JP | 2022515488 | A | 2/2022 |
| JP | 2022516078 | A | 2/2022 |
| JP | 7053500 | B2 | 4/2022 |
| JP | 2022526104 | A | 5/2022 |
| JP | 2022527043 | A | 5/2022 |
| JP | 2022095785 | A | 6/2022 |
| JP | 7171645 | B2 | 11/2022 |
| JP | 7171663 | B2 | 11/2022 |
| JP | 7175640 | B2 | 11/2022 |
| JP | 2022546288 | A | 11/2022 |
| JP | 7187715 | B2 | 12/2022 |

(56) References Cited

FOREIGN PATENT DOCUMENTS

| | | | |
|---|---|---|---|
| JP | 2022551875 | A | 12/2022 |
| JP | 2022552229 | A | 12/2022 |
| JP | 7201819 | B2 | 1/2023 |
| JP | 7232204 | B2 | 3/2023 |
| JP | 7239466 | B2 | 3/2023 |
| JP | 7265525 | B2 | 4/2023 |
| JP | 2023071859 | A | 5/2023 |
| JP | 7299992 | B2 | 6/2023 |
| JP | 7302936 | B2 | 7/2023 |
| JP | 7304344 | B2 | 7/2023 |
| JP | 7321162 | B2 | 8/2023 |
| JP | 7325430 | B2 | 8/2023 |
| JP | 7340594 | B2 | 9/2023 |
| JP | 7346293 | B2 | 9/2023 |
| JP | 7352561 | B2 | 9/2023 |
| JP | 7358391 | B2 | 10/2023 |
| JP | 7359765 | B2 | 10/2023 |
| JP | 7370386 | B2 | 10/2023 |
| JP | 2023162327 | A | 11/2023 |
| JP | 2024010135 | A | 1/2024 |
| JP | 2024020483 | A | 2/2024 |
| JP | 7479288 | B2 | 5/2024 |
| JP | 7479351 | B2 | 5/2024 |
| JP | 7485383 | B2 | 5/2024 |
| JP | 7530561 | B2 | 8/2024 |
| JP | 7542708 | B2 | 8/2024 |
| JP | 2024161427 | A | 11/2024 |
| JP | 7612816 | B2 | 1/2025 |
| JP | 7641600 | B2 | 3/2025 |
| KR | 102574559 | B1 | 9/2023 |
| KR | 102764982 | B1 | 2/2025 |
| KR | 102854907 | B1 | 9/2025 |
| RU | 2589649 | C1 | 7/2016 |
| TW | 201729929 | A | 9/2017 |
| WO | WO94/06355 | A1 | 3/1994 |
| WO | WO98/07373 | A1 | 2/1998 |
| WO | WO02/32506 | A1 | 4/2002 |
| WO | WO2005/018469 | A1 | 3/2005 |
| WO | WO2008/051484 | A2 | 5/2008 |
| WO | WO2011/040054 | A1 | 7/2011 |
| WO | WO2011/092683 | A1 | 8/2011 |
| WO | WO2011/154654 | A2 | 12/2011 |
| WO | WO2012/120740 | A1 | 9/2012 |
| WO | WO2014/008594 | A1 | 1/2014 |
| WO | WO2014/071386 | A1 | 5/2014 |
| WO | WO2015/000953 | A1 | 1/2015 |
| WO | WO2015/031532 | A1 | 3/2015 |
| WO | WO2015/153909 | A2 | 10/2015 |
| WO | WO2016/099279 | A1 | 6/2016 |
| WO | WO2018/149671 | A1 | 8/2018 |
| WO | WO2018/208189 | A1 | 11/2018 |
| WO | WO2019/081329 | A1 | 5/2019 |
| WO | WO2019/117926 | A1 | 6/2019 |
| WO | WO2019/122941 | A1 | 6/2019 |
| WO | WO2019/148154 | A1 | 8/2019 |
| WO | WO2020/074615 | A1 | 4/2020 |
| WO | WO2020/087049 | A1 | 4/2020 |
| WO | WO2020/112688 | A1 | 6/2020 |
| WO | WO2020/217098 | A2 | 10/2020 |
| WO | WO2020/237382 | A1 | 12/2020 |
| WO | WO2020/245660 | A1 | 12/2020 |
| WO | WO2021/014221 | A1 | 1/2021 |
| WO | WO2021/032887 | A1 | 2/2021 |
| WO | WO2021/069216 | A1 | 4/2021 |
| WO | WO2021/069971 | A1 | 4/2021 |
| WO | WO2021/089810 | A1 | 5/2021 |
| WO | WO2021/105358 | A1 | 6/2021 |
| WO | WO2021/115958 | A1 | 6/2021 |
| WO | WO2021/116763 | A1 | 6/2021 |
| WO | WO2021/122253 | A1 | 6/2021 |
| WO | WO2021/123905 | A2 | 6/2021 |
| WO | WO2021/123906 | A1 | 6/2021 |
| WO | WO2021/140042 | A1 | 7/2021 |
| WO | WO2021/142090 | A1 | 7/2021 |
| WO | WO2021/170510 | A1 | 9/2021 |
| WO | WO2021/175626 | A1 | 9/2021 |
| WO | WO2021/176275 | A1 | 9/2021 |
| WO | WO2021/178961 | A1 | 9/2021 |
| WO | WO2021/180501 | A1 | 9/2021 |
| WO | WO2021/180550 | A1 | 9/2021 |
| WO | WO2021/213927 | A1 | 10/2021 |
| WO | WO2021/249936 | A1 | 12/2021 |
| WO | WO2021/258007 | A1 | 12/2021 |
| WO | WO2022/013266 | A1 | 1/2022 |
| WO | WO2022/040493 | A1 | 2/2022 |
| WO | WO2022/047193 | A8 | 3/2022 |
| WO | WO2022/056394 | A1 | 3/2022 |
| WO | WO2022/069254 | A1 | 4/2022 |
| WO | WO2022/069303 | A2 | 4/2022 |
| WO | WO2022/069327 | A2 | 4/2022 |
| WO | WO2022/078744 | A1 | 4/2022 |
| WO | WO2022/097138 | A1 | 5/2022 |
| WO | WO2022/104683 | A1 | 5/2022 |
| WO | WO2022/106891 | A1 | 5/2022 |
| WO | WO2022/152724 | A1 | 7/2022 |
| WO | WO2022/152827 | A1 | 7/2022 |
| WO | WO2022/152828 | A1 | 7/2022 |
| WO | WO2022/238058 | A1 | 11/2022 |
| WO | WO2022/238092 | A1 | 11/2022 |
| WO | WO2022/238229 | A1 | 11/2022 |
| WO | WO2022/238276 | A1 | 11/2022 |
| WO | WO2022/238392 | A1 | 11/2022 |
| WO | WO2022/247242 | A1 | 12/2022 |
| WO | WO2023/274899 | A1 | 1/2023 |
| WO | WO2023/275617 | A2 | 1/2023 |

OTHER PUBLICATIONS

Bader et al.; Assessment of collaborative robot (cobot)-assisted histotripsy for venous clot ablation; IEEE Transactions on Biomedical Engineering; 68(4); pp. 1220-1228; Sep. 11, 2020.

Coon et al.; HIFU treatment time reduction in superficial tumours through focal zone path selection; International journal of hyperthermia; 27(5); pp. 465-481; Aug. 1, 2011.

Froghi et al.; Liver ultrasound histotripsy: novel analysis of the histotripsy site cell constituents with implications for histotripsy application in cell transplantation and cancer therapy; Bioengineering; 10(2); 276; 20 pages; Feb. 20, 2023.

Gobl; Acoustic window planning for ultrasound acquisition. International journal of computer assisted radiology and surgery; 12(6); pp. 993-1001; Jun. 2017.

Stopek; U.S. Appl. No. 19/361,539 entitled "Histotripsy systems and methods for rejected organ recovery" filed Oct. 17, 2025.

Cain et al.; U.S. Appl. No. 19/236,185 entitled "Histotripsy using very short ultrasound pulses," filed Jun. 12, 2025.

Xu et al.; U.S. Appl. No. 19/471,955 entitled "Simultaneous MRI and ultrasound guidance for histotripsy systems and methods," filed Oct. 2, 2025.

Xu et al.; U.S. Appl. No. 19/471,961 entitled "Real-time monitoring of histrotripsy dose delivery damage spatially and temporally," filed Oct. 2, 2025.

Hall et al.; U.S. Appl. No. 19/475,240 entitled "Histotripsy systems and methods," filed Oct. 14, 2025.

Kumar et al.; A comparative study of histotripsy parameters for the treatment of fibrotic ex-vivo human benign prostatic hyperplasia tissue; Research Square rs.3.rs-4549536.2; doi:10.21203/rs-4549536/v1; 24 pages; (Preprint); Jul. 2024.

Vlaisavljevich et al.; Histotripsy-induced caviation cloud initiation thresholds in tissues of different mechanical properties; IEEE Transactions on Ultrasonic, Ferroelectrics, and Frequency control; 61(2); pp. 341-352; 27 pages; (Author manuscript); Feb. 2014.

Vlaisaljevich et al.; Effects of tissue stiffness, ultrasound frequency, and pressure on histotripsy-induced cavitation bubble behavior; Physics in Medical and Biology; 60(6); pp. 2271-2292; 30 pages; (Author manuscript); Mar. 2015.

Vlaisavljevich et al.; Effects of thermal preconditioning on tissue susceptibility to histotripsy; Ultrasound in Medicine and Biology; 41(11); pp. 2938-2954; 27 pages; (Author manuscript); Nov. 2015.

(56) References Cited

OTHER PUBLICATIONS

Vlaisavljevich et al.; Effects of tissue mechanical properties on susceptibility to histotripsy-induced tissue damage; Physics in Medicine and Biology; 59(2); pp. 253-270; 26 pages; (Author Manuscript); Jan. 2014.
Duryea et al.; U.S. Appl. No. 19/270,038, entitled "Histotripsy systems and methods," filed Jul. 15, 2025.
Grumbir et al.; U.S. Appl. No. 19/510,190 entitled "Ultrasound coupling systems for histotripsy and systems, methods, and devices therof," filed Feb. 10, 2026.
Miller et al.; U.S. Appl. No. 19/335,154, entitled "Histotripsy systems and methods," filed Sep. 22, 2025.
Xu et al.; U.S. Appl. No. 19/542,355 entitled "Minimally invasive histotripsy systems and methods," filed Feb. 17, 2026.
Maxwell et al.; U.S. Appl. No. 19/187,641 entitled "Histotripsy for thrombolysis," filed Apr. 23, 2025.
Duryea et al.; U.S. Appl. No. 19/139,227 entitled "Systems and methods for enhancing histotripsy bubble cloud size through pulse shape optimization," filed Jun. 13, 2025.
Cannata et al.; U.S. Appl. No. 19/329,331 entitled "Histotripsy systems and associated methods including user interfaces and workflows for treatment planning and therapy," filed Sep. 15, 2025.
Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Appel et al.; Stereoscopic highspeed recording of bubble filaments; Ultrasonics Sonochemistry; vol. 11(1); pp. 39-42; Jan. 2004.
Arani et al.; Transurethral prostate magnetic resonance elestography; prospective imaging requirements; Magn. Reson. Med.; 65(2); pp. 340-349; Feb. 2011.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Atchley et al.; Thresholds for cavitation produced in water by pulsed ultrasound; Ultrasonics.; vol. 26(5); pp. 280-285; Sep. 1988.
Avago Technologies; ACNV2601 High Insulation Voltage 10 MBd Digital Opotcoupler. Avago Technologies Data Sheet; pp. 1-11; Jul. 29, 2010.
Avago Technologies; Avago's ACNV2601 optocoupler is an optically coupled logic gate; Data Sheet; 2 pages; Jul. 29, 2010.
Avtech; AVR-8 Data sheet; May 23, 2004; 3 pages; retrieved from the internet (http//www.avtechpulse.com).
Bader et al.; For whom the bubble grows: physical principles of bubble nucleation and dynamics in histotripsy ultrasound therapy; Ultrasound in medicine & biology; 45(5); pp. 1056-1080; May 1, 2019.
Bak; Rapid protytyping or rapid production? 3D printing processes move industry towards the latter; Assembly Automation; 23(4); pp. 340-345; Dec. 1, 2003.
Billson et al.; Rapid prototyping technologies for ultrasonic beam focussing in NDE; IEEE International Ultrasonic Symposium Proceedings; pp. 2472-2474; Oct. 2011.
Bjoerk et al.; Cool/MOS CP.—How to make most beneficial use of the generation of super junction technology devices. Infineon Technologies AG. [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderid=db3a304412b407950112b408e8c90004&field=db3a304412b407950112b40ac9a40688>pp. 1, 4, 14; Feb. 2007.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain et al.; Concentric-ring and sector-vortex phased-array applicators for ultrasound hyperthermia; IEEE Transactions on Microwave Theory and Techniques; 34(5); pp. 542-551; May 1986.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vase Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Dovedi et al.; Acquired Resistance to Fractionated Radiotherapy Can Be Overcome by Concurrent PD-LI Blockade; Cancer Research: 74(19); pp. 5458-5468; Oct. 1, 2014.
Emelianov et al.; Triplex ultrasound: Elasticity imaging to age deep venous thrombosis; Ultrasound Med Biol; 28(6); pp. 757-767; Jun. 2002.
Gateau et al.; Transcranial ultrasonic therapy based on time reversal of acoustically induced cavitation bubble signature. IEEE Transactions on Biomedical Engineering; 57(1); pp. 134-144; Sep. 18, 2009.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System For Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Haller et al.; Determination of acoustic cavitation probabilities and thresholds using a single focusing transducer to induce and detect acoustic cavitation events: 1. Method and terminology; Ultrasound in Medicine & Biology; 44(2); pp. 377-396; Feb. 1, 2018.
Hartmann; Ultrasonic properties of poly(4-methyl pentene-1), Journal of Applied Physics, vol. 51, pp. 310-314, Jan. 1980.
Hobarth et al.; Color flow doppler sonography for extracorporal shock wave lithotripsy; Journal of Urology; 150(6); pp. 1768-1770; Dec. 1, 1993.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.

(56) References Cited

OTHER PUBLICATIONS

Hynynen et al.; Feasibility of using ultrasound phased arrays for MRI monitored noninvasive surgery; IEEE transactions on ultrasonics, ferroelectrics, and frequency control; 43(6); pp. 1043-1053; Nov. 1996.
Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue) 1993.
International Society for Magnetic Resonance in Medicine (ISMRM); No. 105; XP040714022;I Jul. 24, 2020.
Hoogenboom et al.; Mechanical high-intensity focused ultrasound destruction of soft tissue: working mechanisms and physiologic effects; Ultrasound in medicine & biology; 41(6); pp. 1500-1517; Jun. 1, 2015.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.
Kim et al.; Dependence of particle vol. fraction on sound velocity and attenuation of EPDM composites; Ultrasonics, vol. 46, pp. 177-183, Feb. 2007.
Kim et al.; Development of a wearable robotic positioning system for noninvasive transcranial focused ultrasound stimulation; IEEE/ASME Transactions on Mechatronics; 21(5); pp. 2284-2293; Jun. 13, 2016.
Konofagou; Quo vadis elasticity imaging?; Ultrasonics; 42(1-9); pp. 331-336, Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Lin et al; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Lu et al.; Transcranial MR-guided histotripsy system; IEEE transactions on ultrasonics, ferroelectrics, and frequency control; 68(9); pp. 2917-2929; Mar. 23, 2021.
Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Maxwell et al.; In-vivo study of non-invasive thrombolysis by histotripsy in a porcine model; IEEE international Ultrasonics Symposium; IEEE; p. 220-223; Sep. 20, 2009.
Maxwell et al.; The role of compressional pressure in the formation of dense bubble clouds in histotripsy; 2009 IEEE International Ultrasonics Symposium; pp. 81-84; Sep. 20, 2009.
Miller et al.; A review of in vitro bioeffects of inertial ultrasonic cavitation from a mechanistic perspective; Ultrasound in Medicine and Biology; vol. 22; pp. 1131-1154; (the year of publication is sufficiently earlier than the effective U.S. filing date and any foreign priority date so that the particular month of publication is not in issue) 1996.
Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.
Miller et al.; Real-time elastography-based monitoring of histotripsy tissue fractionation using color doppler; Ultrasonics Symposium (IUS); 2012 IEEE International; 8 pages; Oct. 7-10, 2012.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Qu et al.; Non-thermal histotripsy tumor ablation promotes abscopal immune responses that enhance cancer immunotherapy; Journal for immunotherapy of cancer; 8(1); Jan. 15, 2020.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rosnitskiy et al.; Method for designing multielement fully populated random phased arrays for ultrasound surgery applications. IEEE transactions on ultrasonics, ferroelectrics, and frequency control; 65(4); pp. 630-637; Jan. 31, 2018.

(56) References Cited

OTHER PUBLICATIONS

Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.
Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Stocker et al.; Endocavity histotripsy for efficient tissue ablationRtransducer design and characterization. IEEE transactions on ultrasonics, ferroelectrics, and frequency control; 68(9); pp. 2896-2905; Jan. 28, 2021.
Sukovich et al.; Real-lime transcranial histotripsy treatment localization and mapping using acoustic cavitation emission feedback; IEEE transactions on ultrasonics, ferroelectrics, and frequency control; 67(6); pp. 1178-1791; Jan. 17, 2020.
Therapeutic Ultrasound Group. Non-Invasive Ultrasonic Tissue Fraction for Treatment of Benign Disease and Cancer—"Histotripsy" University research [online]. Biomedical Engineering Department, University of Michigan. Jul. 2011 [retrieved on Jan. 28, 2014] from: (http:/web.archive.org/web/20110720091822/http://www.histotripsy.umich.edu/index.html> entiredocument) Jul. 2011.
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.
Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.
Wikipedia; Medical ultrasound; 15 pages; retrieved from the internet (https://en.wikipedia.org/w/index.php?title=Medical_utrasound&oldid=515340960) on Jan. 12, 2018.
Wijlemans et al.; Magnetic resonance-guided high-intensity focused ultrasound (MR-HIFU) ablation of liver tumours; Cancer Imaging; 12(2); pp. 387-394; Sep. 28, 2012.
Woodacre et al.; A low-cost miniature histotripsy transducer for precision tissue ablation. IEEE transactions on ultrasonics, ferroelectrics, and frequency control; 65(11); pp. 2131-2140; Nov. 1, 2018.
Wu et al.; Mechanism and dynamics of hydrodynamic-acoustic cavitation (HAC); Ultrasonics sonochemistry; vol. 49., pp. 89-96; Dec. 1, 2018.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).
Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.
Xu et al.; Controlled ultrasound tissue erosion: the role of dynamic interaction between insonation and microbubble activity; Journal of the Acoustical Society of America; vol. 117(1); pp. 424-435; Jan. 2005.
Xu et al.; Controlled ultrasound tissue erosion; IEEE Transaction on Ultrasonics, Ferroelectrics, and Frequency Control; vol. 51 (6); pp. 726-736; Jun. 2004.
Xu et al.; Effects of acoustic parameters on bubble cloud dynamics in ultrasound tissue erosion (histotripsy); Journal of the Acoustical Society of America; vol. 122(1); pp. 229-236; Jul. 2007.
Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.
Xu et al.; Investigation of intensity threshold for ultrasound tissue erosion; Ultrasound in Med. & Biol.; vol. 31(12); pp. 1673-1682; Dec. 2005.
Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.
Yan et al.; A review of rapid prototyping technologies and systems; Computer-Aided Design, vol. 28, pp. 307-318, Apr. 1996.
Zhang et al.; A fast tissue stiffness-dependent elastography for HIFU-induced lesions inspection; Ultrasonics; 51(8); pp. 857-869; Dec. 2011.
Zheng et al.; An acoustic backscatter-based method for localization of lesions induced by high-intensity focused ultrasound; Ultrasound Med Biol; 36(4); pp. 610-622; Apr. 2010.
Cannata et al.; U.S. Appl. No. 18/311,050 entitled "Histotripsy systems and methods," filed May 2, 2023.
Miller; U.S. Appl. No. 19/103,752 entitled "Histotripsy systems and methods," filed Feb. 13, 2025.
Xu et al.; U.S. Appl. No. 19/006,948 entitled "Histotripsy therapy systems and methods for the treatment of brain tissue," filed Dec. 31, 2024.

* cited by examiner

ULTRASOUND TRANSDUCER WITH TRANSMIT-RECEIVE CAPABILITY FOR HISTOTRIPSY

CROSS REFERENCE TO RELATED APPLICATIONS

This application is a continuation of U.S. application Ser. No. 18/043,251, filed Feb. 27, 2023, which is a 371 national phase application of International Application No. PCT/US2021/048008, filed Aug. 27, 2021, which claims the benefit of U.S. Provisional Patent Application No. 63/071,301, filed Aug. 27, 2020, titled "ULTRASOUND TRANSDUCER WITH TRANSMIT-RECEIVE CAPABILITY FOR HISTOTRIPSY", which is incorporated by reference in its entirety.

GOVERNMENT RIGHTS

This invention was made with government support under CA211217, EB028309, and NS108042 awarded by the National Institutes of Health and under N00014-17-1-2058 and N00014-18-1-2625 awarded by the U.S. Office of Naval Research. The government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure details novel histotripsy systems configured to produce acoustic cavitation, methods, devices and procedures for the minimally and non-invasive treatment of healthy, diseased and/or injured tissue. The histotripsy systems and methods described herein, also referred to Histotripsy, may include transducers, drive electronics, positioning robotics, imaging systems, and integrated treatment planning and control software to provide comprehensive treatment and therapy for soft tissues in a patient.

BACKGROUND

Many medical conditions require invasive surgical interventions. Invasive procedures often involve incisions, trauma to muscles, nerves and tissues, bleeding, scarring, trauma to organs, pain, need for narcotics during and following procedures, hospital stays, and risks of infection. Non-invasive and minimally invasive procedures are often favored, if available, to avoid or reduce such issues. Unfortunately, non-invasive and minimally invasive procedures may lack the precision, efficacy or safety required for treatment of many types of diseases and conditions. Enhanced non-invasive and minimally invasive procedures are needed, preferably not requiring ionizing or thermal energy for therapeutic effect.

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, and high-intensity focused ultrasound (HIFU), Histotripsy relies on the mechanical action of cavitation for tissue destruction.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

SUMMARY OF THE DISCLOSURE

Figure 1A:
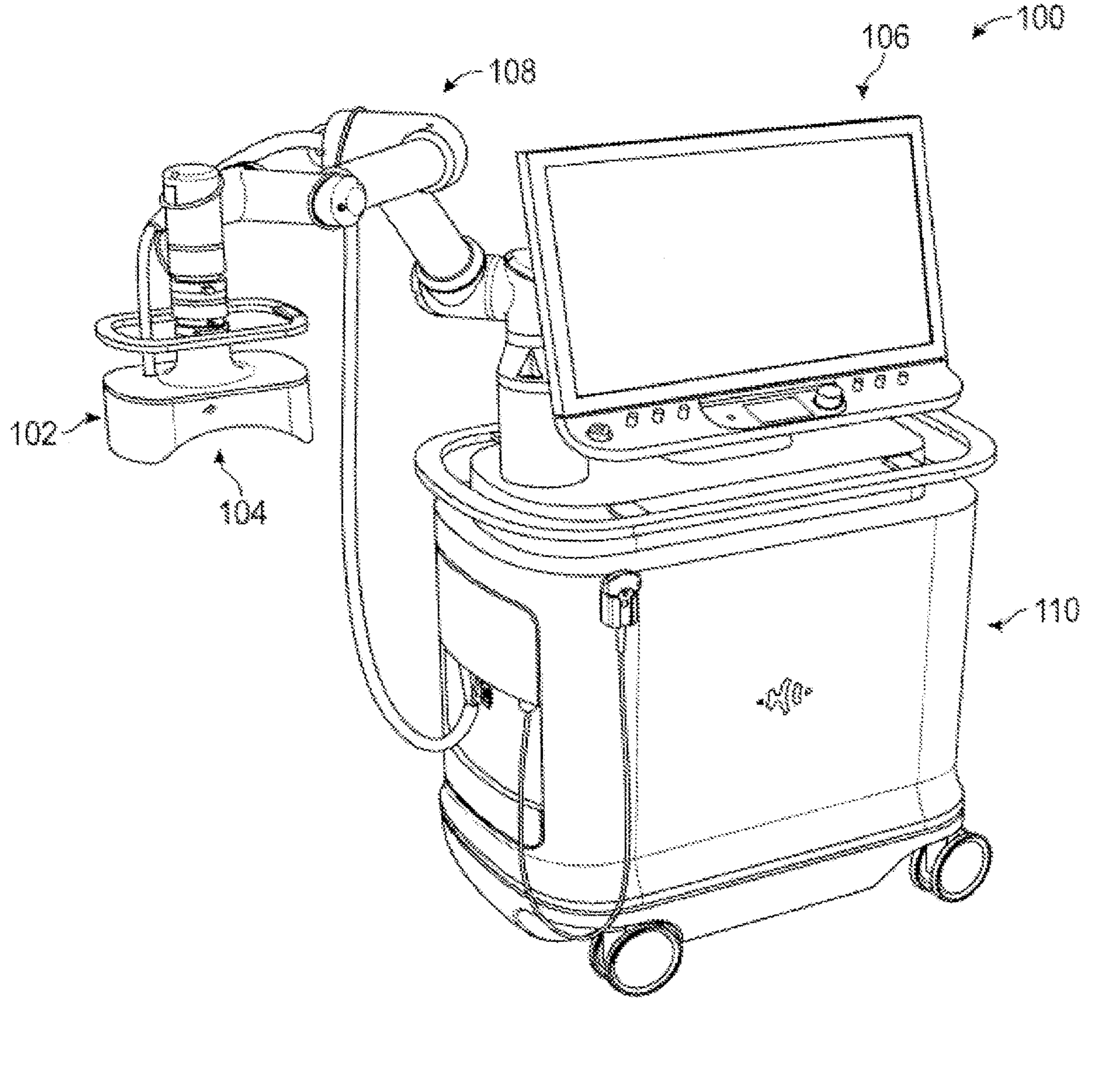
FIGS. 1A-1B illustrate an ultrasound imaging and therapy system.

Histotripsy produces tissue fractionation through dense energetic bubble clouds generated by short, high-pressure, ultrasound pulses. When using pulses shorter than 2 cycles, the generation of these energetic bubble clouds only depends on where the peak negative pressure (P−) exceeds an intrinsic threshold for inducing cavitation in a medium (typically 26-30 MPa in soft tissue with high water content).

A transmit-receive driving electronics for a histotripsy system is provided, comprising at least one transducer element configured to transmit ultrasound pulses in a transmit mode and receive ultrasound reflections and/or acoustic cavitation emissions in a receive mode, a current sense resistor configured to measure a current in the transmit-receive driving electronics during the receive mode, a bypass circuit electrically coupled to the at least one transducer element and the current sense resistor, wherein the bypass circuit is configured to be switched on during the transmit mode to bypass the current sense resistor and switched off during the receive mode to allow the sense resistor to measure the current; a gain adjustment circuit electrically coupled to the current sense resistor and to a low sensitivity resistor, the gain adjustment circuit being configured to operate in a high sensitivity setting in which the current sense resistor is switched on and the low sensitivity resistor is switched off, and wherein the gain adjustment circuit is further configured to operate in a low sensitivity setting in which the current sense resistor and the low sensitivity resistor are switched on.

In some embodiments, he transmit-receive driving electronics further comprises a drive transformer electrically coupled to the at least one transducer element.

In some examples, the bypass circuit further comprises a pair of bypass transistors. In other embodiments, the bypass circuit further comprises a pair of bypass diodes.

In some embodiments, the gain adjustment circuit further comprises a pair of transistors. In other embodiments, the current sense resistor has a higher resistance than the low sensitivity resistor.

In one example, the current sense resistor has a resistance of approximately 200 ohms and the low sensitivity resistor has a resistance of approximately 5 ohms.

A transmit-receive driving electronics for a histotripsy system is also provided, comprising an ultrasound transducer array, high-voltage transmission electronics coupled to the ultrasound transducer array and configured to provide up to thousands of volts to the ultrasound transducer array to produce one or more histotripsy pulses, first receive electronics coupled to the ultrasound transducer array and configured to receive incoming voltage signals from the transmitted one or more histotripsy pulses, the first receive electronics being configured to attenuate the incoming voltage signals by 90-99%, second receive electronics configured to compress any attenuated incoming voltage signals above IV, and third receive electronics configured to voltage shift the attenuated incoming voltage signals, and an analog-to-digital converter configured to receive the voltage-shifted attenuated incoming voltage signals from the third receive electronics for ADC conversion.

In some embodiments, the first electronics comprise a voltage divider.

In other embodiments, the voltage divider comprises a capacitive voltage divider.

In one embodiment, the capacitive voltage divider comprises a first capacitor and a second capacitor in parallel with a first transducer element of the ultrasound transducer array.

In one embodiment, the second receive electronics comprise a diode-resistor voltage divider. In another embodiment, the third receive electronics are configured to voltage shift the attenuated incoming voltage signals to an appropriate voltage range for the analog-to-digital converter.

In some embodiments, the transmit-driving electronics comprise a separate circuitry board that is configured to be retrofitted to an existing histotripsy system that includes a transmit-only histotripsy driving system.

In one example, the transmit-driving electronics is added in parallel to the transmit-only histotripsy driving system and is configured to passively receive signals without affecting the transmit-only electronics.

In some embodiments, the transmit-receive driving electronics are further configured to synchronize a time clock of the transmitted one or more histotripsy pulses, received incoming voltage signals, and the ADC conversion to obtain an appropriate time window after each histotripsy pulse transmission.

In one embodiment, the transmit-receive driving electronics further comprise one or more Field Programmable Gate Array (FPGA) boards coupled to the analog-to-digital converter and being configured to control transmit and receive operations of the transmit-receive driving electronics with a single clock. In some examples, the one or more FPGA includes software or firmware configured to reduce a data load for received signals. In other embodiments, the one or more FPGA are configured to artificially downsample incoming data from the analog-to-digital converter. In another embodiment, the one or more FPGA are configured to oversample and average the received signals to increase a signal to noise ratio (SNR).

A method of using a transmit-receive histotripsy system for cavitation detection is provided, comprising the steps of transmitting high-voltage histotripsy therapy pulses into a target tissue with transmit electronics and a histotripsy therapy transducer array to generate cavitation in the target tissue, receiving low-voltage acoustic cavitation emission signals from the cavitation with receive electronics and the histotripsy therapy transducer array, processing the received acoustic cavitation emission signals to monitor treatment progression.

In some examples, the method further comprises generating a 3D map of cavitation produced by the transmitted pulses in real-time.

A method of using a transmit-receive histotripsy system for aberration correction is provided, comprising the steps of transmitting histotripsy therapy pulses into a target tissue with a histotripsy therapy transducer array having a plurality of transducer elements to generate cavitation in the target tissue, receiving acoustic cavitation emission signals from the cavitation with the histotripsy therapy transducer array, calculating a travel time from the cavitation to each transducer element of the ultrasound transducer array based on the received acoustic cavitation emission signals, and adjusting a transmission time delay for at least one of the plurality of transducer elements based on the calculated travel times such that subsequent histotripsy therapy pulses arrive at the target tissue simultaneously.

In some embodiments, calculating the travel time includes using information encoded in the acoustic cavitation emissions.

In one example, the information comprises a start time of the acoustic cavitation emission generated from cavitation expansion.

In some embodiments, the information comprises a start time of the acoustic cavitation emission generated from cavitation collapse.

In one embodiment, the information comprises a peak time from cavitation collapse.

A receive-drive circuit configured to be retrofitted onto one or more transducer elements of an existing transmit-only histotripsy system is provided, comprising a voltage divider configured to be electrically coupled to a first transducer element, the voltage divider configured to attenuate voltage signals received by the first transducer element, a diode-resistor voltage divider electrically coupled to the voltage divider, the diode-resistor voltage divider being configured to provide nonlinear attenuation to compress signals above a predetermined voltage, and being further configured to AC couple the received signals to an analog to digital converter.

In some embodiments, the voltage divider and the diode-resistor voltage divider are configured to be disposed on a first circuitry board and that is configured to be electrically coupled to high-voltage histotripsy driving electronics disposed on a separate second circuitry board.

In another embodiment, the receive-drive circuit and high-voltage histotripsy driving electronics are disposed on a single circuitry board.

A transmit-receive histotripsy system is provided, comprising a transducer element, transmit electronics coupled to the transducer element and configured to deliver histotripsy pulses to the transducer element, a non-linear compressor receive electronics coupled to the transducer element, wherein the non-linear compressor receive electronics are configured to compress a first voltage signal with a first attenuation, and are further configured to compress a second voltage signal with a second attenuation, wherein the first voltage signal is higher than the second voltage signal and the first attenuation is higher than the second attenuation.

A transmit-receive driving electronics for a histotripsy system is also provided, comprising a transducer element, a secondary transformer coil electrically coupled to the transducer element, a primary transformer coil positioned adjacent to the secondary transformer coil, the primary transformer coil being configured to generate ultrasound pulses in the transducer element via the secondary transformer coil, a third transformer coil positioned adjacent to the secondary transformer coil, the third transformer coil being configured to attenuate voltage signals received by the transducer element by a predetermined amount.

In some embodiments, the third transformer coil is configured to attenuate the received voltage signals by 90-99%. In another embodiment, the third transformer coil is wound with approximately 7-10× fewer windings than the secondary transformer coil.

In some embodiments, the third transformer coil is configured to saturate during transmission of ultrasound pulses.

In another embodiment, the third transformer coil is coupled to a signal transformer with a specifically chosen core material and size such that the signal transformer is configured to saturate during transmission of ultrasound pulses.

A transmit-receive driving electronics of a histotripsy system is provided, comprising an ultrasound transducer array, transmission electronics coupled to the ultrasound transducer array and configured to transmit one or more histotripsy pulses to generate cavitation in a target tissue, receive electronics configured to receive acoustic cavitation emissions from the cavitation, a transmit-receive switch configured to enable only the transmission electronics during transmission of the one or more histotripsy pulses, the transmit-receive switch being further configured to enable only the receive electronics at a predetermined time after the transmission of the one or more histotripsy pulses, to block transmission signals without attenuating received signals.

In one embodiment, a different linear gain follows the transmit-receive switch to amplify or attenuate a selected portion of the received signal based on its amplitude to maximize a receive sensitivity of the receive electronics.

A method histotripsy therapy is provided, comprising the steps of transmitting histotripsy therapy pulses into a target tissue with a histotripsy therapy transducer array to generate cavitation in the target tissue, receiving acoustic cavitation emission signals from the cavitation with the histotripsy therapy transducer, detecting a selected acoustic cavitation emission feature to separate from tissue signals, calculating a cavitation parameter that correlates to tissue damage generated by the histotripsy therapy pulses, determining a change in the cavitation parameter that correlates to treatment progression, determining a change in the cavitation parameter that correlates to treatment completion.

In one example, the selected acoustic cavitation emission feature comprises a timing of cavitation bubble expansion signals.

In another example, the selected acoustic cavitation emission feature comprises an amplitude of cavitation bubble expansion signals.

In some embodiments, the selected acoustic cavitation emission feature comprises a timing of cavitation bubble collapse signals.

In another embodiment, the selected acoustic cavitation emission feature comprises an amplitude of cavitation bubble collapse signals.

In some embodiments, the selected acoustic cavitation emission feature comprises a timing of cavitation bubble rebound signals.

In one embodiment, the selected acoustic cavitation emission feature comprises an amplitude of cavitation bubble rebound signals.

In another embodiment, the cavitation parameter comprises a collapse time of the cavitation.

In some examples, the collapse time comprises a time between expansion and collapse signals of the cavitation.

In another embodiment, the cavitation parameter comprises a peak amplitude of an expansion signal of the cavitation.

In some embodiments, the cavitation parameter comprises a peak amplitude of a collapse signal of the cavitation.

In another embodiment, the cavitation parameter comprises amplitude ratios of a growth ACE signal of the cavitation.

In some embodiments, the cavitation parameter comprises amplitude ratios of a collapse ACE signal of the cavitation.

In another embodiment, the cavitation parameter comprises a decay rate of rebound-associated ACE signal amplitudes.

In one example, determining a change in the cavitation parameter that correlates to treatment progression further comprises identifying an increasing slope in the cavitation parameter.

In another example, determining a change in the cavitation parameter that correlates to treatment completion further comprises identifying saturation of the change in the cavitation parameter.

A method for cavitation detection during histotripsy is provided, comprising the steps of transmitting histotripsy therapy pulses into a target tissue with a histotripsy therapy transducer array to generate cavitation in the target tissue, receiving acoustic cavitation emission signals from the cavitation with the histotripsy therapy transducer array, detecting a selected acoustic cavitation emission feature to separate from tissue signals, processing and forming a cavitation map based on the selected acoustic cavitation emission feature, and overlaying the cavitation map onto an image of the target tissue.

In some examples, the selected acoustic cavitation emission feature comprises a timing of cavitation bubble expansion signals. In other examples, the selected acoustic cavitation emission feature comprises an amplitude of cavitation bubble expansion signals. In additional examples, the selected acoustic cavitation emission feature comprises a timing of cavitation bubble collapse signals. In one embodiment, the selected acoustic cavitation emission feature comprises an amplitude of cavitation bubble collapse signals. In some embodiments, the selected acoustic cavitation emission feature comprises a timing of cavitation bubble rebound signals. In another example, the selected acoustic cavitation emission feature comprises an amplitude of cavitation bubble rebound signals.

A method of performing aberration correction during histotripsy therapy is provided, comprising the steps of transmitting histotripsy therapy pulses into a target tissue with a histotripsy therapy transducer array to generate cavitation in the target tissue, receiving acoustic cavitation emission signals from the cavitation with the histotripsy therapy transducer array, analyzing the acoustic cavitation emission signals to detect the cavitation generated in the target tissue, testing presets of transmission time delays to select a set of transmission time delays that can maximize a peak signal amplitude in the detected cavitation, and applying the selected set of transmission time delays such that subsequent histotripsy therapy pulses arrive at the target tissue simultaneously.

DETAILED DESCRIPTION

Provided herein are systems and methods that provide efficacious non-invasive and minimally invasive therapeutic, diagnostic and research procedures. In particular, provided herein are optimized systems and methods that provide targeted, efficacious histotripsy in a variety of different regions and under a variety of different conditions without causing undesired tissue damage to intervening/non-target tissues or structures.

Balancing desired tissue destruction in target regions with the avoidance of damage to non-target regions presents a technical challenge. This is particularly the case where time efficient procedures are desired. Conditions that provide fast, efficacious tissue destruction tend to cause undue heating in non-target tissues. Undue heating can be avoided by reducing energy or slower delivery of energy, both of which run contrary to the goals of providing a fast and efficacious destruction of target tissue. Provided herein are a number of technologies that individually and collectively allow for fast, efficacious target treatment without undesired damage to non-target regions.

The system, methods and devices of the disclosure may be used for the minimally or non-invasive acoustic cavitation and treatment of healthy, diseased and/or injured tissue, including in extracorporeal, percutaneous, endoscopic, laparoscopic, and/or as integrated into a robotically-enabled medical system and procedures. As will be described below, the histotripsy system may include various electrical, mechanical and software sub-systems, including a Cart, Therapy, Integrated Imaging, Robotics, Coupling and Software. The system also may comprise various Other Components, Ancillaries and Accessories, including but not limited to patient surfaces, tables or beds, computers, cables and connectors, networking devices, power supplies, displays, drawers/storage, doors, wheels, illumination and lighting and various simulation and training tools, etc. All systems, methods and means creating/controlling/delivering histotripsy are considered to be a part of this disclosure, including new related inventions disclosed herein.

In one embodiment, the histotripsy system is configured as a mobile therapy cart, which further includes a touchscreen display with an integrated control panel with a set of physical controls, a robotic arm, a therapy head positioned on the distal end of the robot, a patient coupling system and software to operate and control the system.

The mobile therapy cart architecture can comprise internal components, housed in a standard rack mount frame, including a histotripsy therapy generator, high voltage power supply, transformer, power distribution, robot controller, computer, router and modem, and an ultrasound imaging engine. The front system interface panel can comprise input/output locations for connectors, including those specifically for two ultrasound imaging probes (handheld and probe coaxially mounted in the therapy transducer), a histotripsy therapy transducer, AC power and circuit breaker switches, network connections and a foot pedal. The rear panel of the cart can comprise air inlet vents to direct airflow to air exhaust vents located in the side, top and bottom panels. The side panels of the cart include a holster and support mechanism for holding the handheld imaging probe. The base of the cart can be comprised of a cast base interfacing with the rack mounted electronics and providing an interface to the side panels and top cover. The base also includes four recessed casters with a single total locking mechanism. The top cover of the therapy cart can comprise the robot arm base and interface, and a circumferential handle that follows the contour of the cart body. The cart can have inner mounting features that allow technician access to cart components through access panels.

The touchscreen display and control panel may include user input features including physical controls in the form of six dials, a space mouse and touchpad, an indicator light bar, and an emergency stop, together configured to control imaging and therapy parameters, and the robot. The touchscreen support arm is configured to allow standing and seated positions, and adjustment of the touchscreen orientation and viewing angle. The support arm further can comprise a system level power button and USB and ethernet connectors.

The robotic arm can be mounted to the mobile therapy cart on arm base of sufficient height to allow reach and ease of use positioning the arm in various drive modes into the patient/procedure work space from set up, through the procedure, and take down. The robotic arm can comprise six degrees of freedom with six rotating joints, a reach of 850 mm and a maximum payload of 5 kg. The arm may be controlled through the histotripsy system software as well as a 12 inch touchscreen polyscope with a graphical user interface. The robot can comprise force sensing and a tool flange, with force (x, y, z) with a range of 50 N, precision of 3.5 N and accuracy of 4.0 N, and torque (x, y, z) with a range of 10.0 Nm, precision of 0.2 Nm and accuracy of 0.3 Nm. The robot has a pose repeatability of +/−0.03 mm and a typical TCP speed of 1 m/s (39.4 in/s). In one embodiment, the robot control box has multiple I/O ports, including 16 digital in, 16 digital out, 2 analog in, 2 analog out and 4 quadrature digital inputs, and an I/O power supply of 24V/2 A. The control box communication comprises 500 Hz control frequency, Modbus TCP, PROFINET, ethernet/IP and USB 2.0 and 3.0.

The therapy head can comprise one of a select group of four histotripsy therapy transducers and an ultrasound imaging system/probe, coaxially located in the therapy transducer, with an encoded mechanism to rotate said imaging probe independent of the therapy transducer to known positions, and a handle to allow gross and fine positioning of the therapy head, including user inputs for activating the robot (e.g. for free drive positioning). In some examples, the therapy transducers may vary in size (22×17 cm to 28×17 cm), focal lengths from 12-18 cm, number of elements, ranging from 48 to 64 elements, comprised within 12-16 rings, and all with a frequency of 700 kHz. The therapy head subsystem has an interface to the robotic arm includes a quick release mechanism to allow removing and/or changing the therapy head to allow cleaning, replacement and/or selection of an alternative therapy transducer design (e.g., of different number of elements and geometry), and each therapy transducer is electronically keyed for auto-identification in the system software.

The patient coupling system can comprise a six degree of freedom, six joint, mechanical arm, configured with a mounting bracket designed to interface to a surgical/interventional table rail. The arm may have a maximum reach of approximately 850 mm and an average diameter of 50 mm. The distal end of the arm can be configured to interface with an ultrasound medium container, including a frame system and an upper and lower boot. The lower boot is configured to support either a patient contacting film, scaled to patient, or an clastic polymer membrane, both designed to contain ultrasound medium (e.g., degassed water or water mixture), either within the frame and boot and in direct contact with the patient, or within the membrane/boot construct. The lower boot provides, in one example, a top and bottom window of approximately 46 cm×56 cm and 26 cm×20 cm, respectively, for placing the therapy transducer with the ultrasound medium container and localized on the patient's abdomen. The upper boot may be configured to allow the distal end of the robot to interface to the therapy head and/or transducer, and to prevent water leakage/spillage. In preferred embodiments, the upper boot is a sealed system. The frame is also configured, in a sealed system, to allow two-way fluid communication between the ultrasound medium container and an ultrasound medium source (e.g., reservoir or fluidics management system), including, but not limited for filling and draining, as well as air venting for bubble management.

The system software and workflow can be configured to allow users to control the system through touchscreen display and the physical controls, including but not limited to, ultrasound imaging parameters and therapy parameters. The graphical user interface of the system comprises a workflow based flow, with the general procedure steps of 1) registering/selecting a patient, 2) planning, comprising imaging the patient (and target location/anatomy) with the freehand imaging probe, and robot assisted imaging with the transducer head for final gross and fine targeting, including contouring the target with a target and margin contour, of which are typically spherical and ellipsoidal in nature, and running a test protocol (e.g., test pulses) including a bubble cloud calibration step, and a series of predetermined locations in the volume to assess cavitation initiation threshold and other patient/target specific parameters (e.g., treatment depth), that together inform a treatment plan accounting for said target's location and acoustic pathway, and any related blockage (e.g., tissue interfaces, bone, etc.) that may require varied levels of drive amplitude to initiate and maintain histotripsy. Said parameters, as measured as a part of the test protocol, comprising calibration and multi-location test pulses, are configured in the system to provide input/feedback for updating bubble cloud location in space as needed/desired (e.g., appropriately calibrated to target cross-hairs), as well as determining/interpolating required amplitudes across all bubble cloud treatment locations in the treatment volume to ensure threshold is achieved throughout the volume. Further, said parameters, including but not limited to depth and drive voltage, may be also used as part of an embedded treatability matrix or look up table to determine if additional cooling is required (e.g., off-time in addition to time allocated to robot motions between treatment pattern movements) to ensure robust cavitation and intervening/collateral thermal effects are managed (e.g., staying below t43 curve for any known or calculated combination of sequence, pattern and pathway, and target depth/blockage). The workflow and procedure steps associated with these facets of planning, as implemented in the system software may be automated, wherein the robot and controls system are configured to run through the test protocol and locations autonomously, or semi-autonomously. Following planning, the next phase of the procedure workflow, 3) the treatment phase, is initiated following the user accepting the treatment plan and initiating the system for treatment. Following this command, the system is configured to deliver treatment autonomously, running the treatment protocol, until the prescribed volumetric treatment is complete. The status of the treatment (and location of the bubble cloud) is displayed in real-time, adjacent to various treatment parameters, including, but not limited to, of which may include total treatment time and remaining treatment time, drive voltage, treatment contours (target/margin) and bubble cloud/point locations, current location in treatment pattern (e.g., slice and column), imaging parameters, and other additional contextual data (e.g., optional DICOM data, force torque data from robot, etc.). Following treatment, the user may use the therapy head probe, and subsequently, the freehand ultrasound probe to review and verify treatment, as controlled/viewed through the system user interface. If additional target locations are desired, the user may plan/treat additional targets, or dock the robot to a home position on the cart if no further treatments are planned.

FIG. 1A generally illustrates histotripsy system 100 according to the present disclosure, comprising a therapy transducer 102, an imaging system 104, a display and control panel 106, a robotic positioning arm 108, and a cart 110. The system can further include an ultrasound coupling interface and a source of coupling medium, not shown.

Figure 1B:
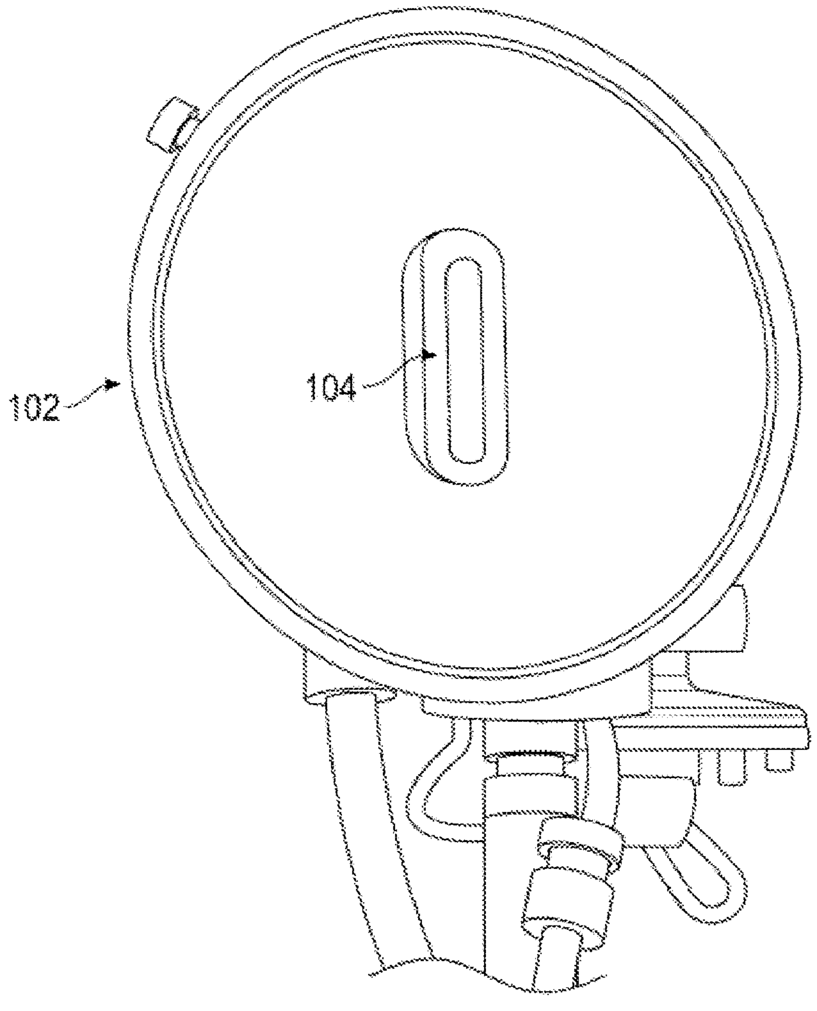

FIG. 1B is a bottom view of the therapy transducer 102 and the imaging system 104. As shown, the imaging system can be positioned in the center of the therapy transducer. However, other embodiments can include the imaging system positioned in other locations within the therapy transducer, or even directly integrated into the therapy transducer. In some embodiments, the imaging system is configured to produce real-time imaging at a focal point of the therapy transducer.

The histotripsy system may comprise one or more of various sub-systems, including a Therapy sub-system that can create, apply, focus and deliver acoustic cavitation/histotripsy through one or more therapy transducers, Integrated Imaging sub-system (or connectivity to) allowing real-time visualization of the treatment site and histotripsy effect through-out the procedure, a Robotics positioning sub-system to mechanically and/or electronically steer the therapy transducer, further enabled to connect/support or interact with a Coupling sub-system to allow acoustic coupling between the therapy transducer and the patient, and Software to communicate, control and interface with the system and computer-based control systems (and other external systems) and various Other Components, Ancillaries and Accessories, including one or more user interfaces and displays, and related guided workflows, all working in part or together. The system may further comprise various fluidics and fluid management components, including but not limited to, pumps, valve and flow controls, temperature and degassing controls, and irrigation and aspiration capabilities, as well as providing and storing fluids. It may also contain various power supplies and protectors.

Cart

The Cart 110 may be generally configured in a variety of ways and form factors based on the specific uses and procedures. In some cases, systems may comprise multiple Carts, configured with similar or different arrangements. In some embodiments, the cart may be configured and arranged to be used in a radiology environment and in some cases in concert with imaging (e.g., CT, cone beam CT and/or MRI scanning). In other embodiments, it may be arranged for use in an operating room and a sterile environment, or in a robotically enabled operating room, and used alone, or as part of a surgical robotics procedure wherein a surgical robot conducts specific tasks before, during or after use of the system and delivery of acoustic cavitation/histotripsy. As such and depending on the procedure environment based on the aforementioned embodiments, the cart may be positioned to provide sufficient work-space and access to various anatomical locations on the patient (e.g., torso, abdomen, flank, head and neck, etc.), as well as providing work-space for other systems (e.g., anesthesia cart, laparoscopic tower, surgical robot, endoscope tower, etc.).

The Cart may also work with a patient surface (e.g., table or bed) to allow the patient to be presented and repositioned in a plethora of positions, angles and orientations, including allowing changes to such to be made pre, peri and post-procedurally. It may further comprise the ability to interface and communicate with one or more external imaging or image data management and communication systems, not limited to ultrasound, CT, fluoroscopy, cone beam CT, PET, PET/CT, MRI, optical, ultrasound, and image fusion and or image flow, of one or more modalities, to support the procedures and/or environments of use, including physical/mechanical interoperability (e.g., compatible within cone beam CT work-space for collecting imaging data pre-, peri-and/or post-histotripsy).

In some embodiments one or more Carts may be configured to work together. As an example, one Cart may comprise a bedside mobile Cart equipped with one or more Robotic arms enabled with a Therapy transducer, and Therapy generator/amplifier, etc., while a companion cart working in concert and at a distance of the patient may comprise Integrated Imaging and a console/display for controlling the Robotic and Therapy facets, analogous to a surgical robot and master/slave configurations.

In some embodiments, the system may comprise a plurality of Carts, all slave to one master Cart, equipped to conduct acoustic cavitation procedures. In some arrangements and cases, one Cart configuration may allow for storage of specific sub-systems at a distance reducing operating room clutter, while another in concert Cart may comprise essentially bedside sub-systems and componentry (e.g., delivery system and therapy).

One can envision a plethora of permutations and configurations of Cart design, and these examples are in no way limiting the scope of the disclosure.

Histotripsy

Histotripsy comprises short, high amplitude, focused ultrasound pulses to generate a dense, energetic, "bubble cloud", capable of the targeted fractionation and destruction of tissue. Histotripsy is capable of creating controlled tissue erosion when directed at a tissue interface, including tissue/fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat or ionizing (high) energy to treat tissue. Instead, histotripsy uses acoustic cavitation generated at the focus to mechanically effect tissue structure, and in some cases liquefy, suspend, solubilize and/or destruct tissue into sub-cellular components.

Histotripsy can be applied in various forms, including: 1) Intrinsic-Threshold Histotripsy: Delivers pulses with at least a single negative/tensile phase sufficient to cause a cluster of bubble nuclei intrinsic to the medium to undergo inertial cavitation, 2) Shock-Scattering Histotripsy: Delivers typically pulses 3-20 cycles in duration. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed totally non-invasively by acoustically coupling a focused ultrasound transducer over the skin of a patient and transmitting acoustic pulses transcutaneously through overlying (and intervening) tissue to the focal zone (treatment zone and site). It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 3 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the "shock scattering mechanism".

This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When ultrasound pulses less than 2 cycles are applied, shock scattering can be minimized, and the generation of a dense bubble cloud depends on the negative half cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

With high-frequency Histotripsy pulses, the size of the smallest reproducible lesion becomes smaller, which is beneficial in applications that require precise lesion generation. However, high-frequency pulses are more susceptible to attenuation and aberration, rendering problematical treatments at a larger penetration depth (e.g., ablation deep in the body) or through a highly aberrative medium (e.g., transcranial procedures, or procedures in which the pulses are transmitted through bone(s)). Histotripsy may further also be applied as a low-frequency "pump" pulse (typically <2 cycles and having a frequency between 100 kHz and 1 MHz) can be applied together with a high-frequency "probe" pulse (typically <2 cycles and having a frequency greater than 2 MHz, or ranging between 2 MHz and 10 MHz) wherein the peak negative pressures of the low and high-frequency pulses constructively interfere to exceed the intrinsic threshold in the target tissue or medium. The low-frequency pulse, which is more resistant to attenuation and aberration, can raise the peak negative pressure P− level for a region of interest (ROI), while the high-frequency pulse, which provides more precision, can pinpoint a targeted location within the ROI and raise the peak negative pressure P− above the intrinsic threshold. This approach may be referred to as "dual frequency", "dual beam histotripsy" or "parametric histotripsy."

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such.

Technical Challenges With Histotripsy

There are two technical challenges for using ultrasound therapy such as histotripsy to treat a deep tissue target (e.g., >8 cm) or through heterogenous tissue: 1) acoustic aberration and 2) real-time feedback of the ultrasound therapy.

Acoustic aberration is a problem that impacts ultrasound therapy and imaging, including histotripsy. Acoustic aberration can reduce the focal pressure and distort the focus due to ultrasound propagation through multi-layer heterogenous tissue. Reduction of the focal pressure can cause ineffective treatment or reduced treatment efficiency. For example, in histotripsy, focal pressures at the target tissue site are precisely controlled to generate cavitation at the target tissue site. Reduction of the focal pressures due to aberration can prevent cavitation from occurring. Distortion of the focus can also decrease treatment accuracy. Typically, a focused ultrasound transducer is shaped as a segment of a spherical surface, such that the sound wave emitted from all locations from the transducer surface go through the same distance to arrive at the focus at the same time. However, due to the variation of speed of sound across bones and heterogeneous soft tissue, the travel time from different elements of an ultrasound transducer array to arrive at the focus may be different. As a result, aberration can result in loss of focal pressure and defocusing, decreasing treatment efficacy and accuracy.

As ultrasound is a non-invasive therapy technique, real-time feedback is critical to achieve high treatment accuracy and minimizing any potential complications. Ultrasound imaging has been used to provide real-time feedback for histotripsy, as histotripsy-generated cavitation can be visualized on ultrasound images as a dynamic, bright zone. Typically, an ultrasound imaging probe is inserted in a central hole of the histotripsy transducer, thus the 2D ultrasound imaging plane contains the histotripsy focus. Ultrasound imaging can then be used to guide the targeting to place histotripsy focus to the correct target tissue and to monitor the treatment progression. However, there are two main limitations of using ultrasound imaging as the sole guidance for histotripsy. 1) When the ultrasound imaging probe is blocked by bone of the patient (e.g., ribs or skull), ultrasound images of the histotripsy focus cannot be obtained. For example, histotripsy can be used to treat a tumor volume in the liver of a patient, which is partially behind the ribcage. When the histotripsy transducer is mechanically moved to scan the histotripsy focus to cover the tumor volume, the imaging probe can be blocked by the ribs for a certain duration of the therapy, at which point no real-time imaging of the therapy is available due to the rib blockage. Without any feedback during this duration, there is no way of knowing if cavitation is still generated at the target locations in the tumor (i.e., if the treatment is implemented over this duration). 2) Ultrasound imaging probes can only view the tissue and cavitation within the 2D image plane that contains the histotripsy focus. Thus, ultrasound imaging probes cannot view any potential unwanted cavitation occurring outside the image plane. Unwanted cavitation may generate undesired off-target damage.

The problems described above can be solved with a novel histotripsy ultrasound phased array transducer, as described herein, that is configured to transmit ultrasound signals to generate cavitation and deliver histotripsy as well as is configured to receive ultrasound signals (i.e., a transmit-receive histotripsy array).

For example, when the ultrasound therapy transducer comprises a phased array, phase correction techniques can be used to correct aberration to recover reduced focal pressure. This can be accomplished by adjusting the phase/time delay at transmission from each transducer element of the phased array to compensate for the travel time variation from each array element to the focus due to the speed of sound variation. In doing so, the aberration can be corrected to increase the focal pressure and improve the focusing.

An ultrasound phased array transducer that can delivery histotripsy and receive acoustic cavitation emission signals can further be configured to allow detection, localization, and mapping of cavitation. Currently, a typical histotripsy system only transmits ultrasound pulses to generate cavitation at the focus. A transmit-receive histotripsy system can not only be used to deliver ultrasound pulses to generate cavitation, but also can receive signals such as the acoustic cavitation emission (ACE) signals. Both the rapid expansion and rapid collapse of cavitating bubbles during histotripsy produce shockwaves that can be detected by an acoustic receiver. In some embodiments, received reflections of the main therapy pulse (if >1-2 cycles long and not fully transformed to shockwave in cavitation generation event) or subsequent low amplitude therapy pulses could be used in various receive application listed below. By processing the ACE signals received from a histotripsy transducer array system with hundreds of elements and transmit-receive capability, cavitation can be detected and localized to provide a real-time, 3D cavitation map. The acoustic emission signals from the growth and/or collapse of histotripsy-induced cavitation microbubbles, received by the histotripsy array, can be used to localize and monitor the cavitation in 3D and real-time, even in situations where the ultrasound imaging probe is blocked by bone. 3D cavitation mapping can also allow real-time monitoring of any off-focus cavitation to increase safety and identify unwanted cavitation.

Transmit-receive driving electronics found in typical phased array systems cannot be directly adapted for a histotripsy phased array transducer because of the extremely high voltages (thousands of volts) necessary for generating high-pressure histotripsy pulses. A novel driving electronics, as described herein, is configured to safely block or significantly attenuate the transmit signal to the ultrasound transducer array while maintaining high sensitivity and high dynamic range for received ultrasound signals. This disclosure provides both hardware and software for a phased array histotripsy transducer array with transmit and receive capability. This disclosure further describes the methods and signal processing algorithms that can be used with the transmit-receive histotripsy system for aberration correction and cavitation mapping.

Transmit-Receive Electric Driving System

The electric transmit signal to a histotripsy transducer is typically on the order of Kilovolts, while received ultrasound signals typically range from millivolts to tens of Volts. Thus, the transmit-receive electric driving circuitry as described herein is designed and configured to block or heavily attenuate the high-amplitude transmit waveform signals on the order of thousands of Volts, while having sufficient sensitivity and dynamic range to receive the low-amplitude signals on the order of tens of Volts.

Many drive circuitry embodiments and implementations to achieve the stated function/purpose above are described herein. In some examples, the drive circuitry can be retrofitted or added-on to an existing transmit-only histotripsy system to provide transmit-receive capabilities. In other embodiments, the drive circuitry is integrated into an entirely new transmit-receive histotripsy system.

Figure 2A:
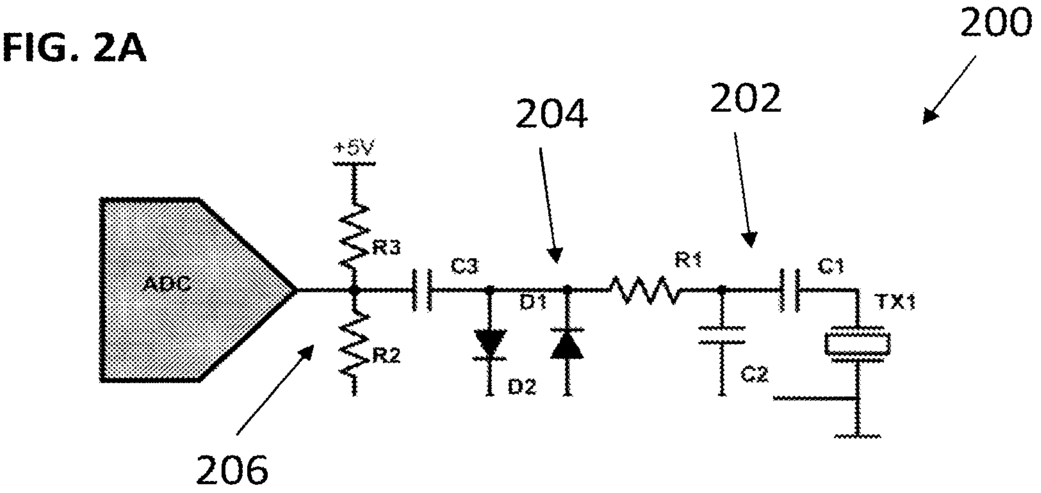
FIGS. 2A-2D illustrate various schematic illustrations of transmit-receive drive electronics for a histotripsy system.

FIG. 2A is one embodiment of a novel receive drive circuitry 200 configured to be retrofitted onto an existing transmit-only histotripsy system to enable transmit-receive functionality. In the illustrated schematic drawing, a non-linear compressor can attenuate all the signals connected to each of the histotripsy elements, but with more attenuation for the high-amplitude signals and less attenuation for the low-amplitude signals. For example, a capacitive voltage divider 202, as indicated by C1 and C2, can first be configured to attenuate all incoming/received voltage signals from transducer element TX1 to approximately 1-10% (or to attenuate the signals by 90-99%). Then a diode-resistor voltage divider 204, as indicated by D1, D2, and C3, is configured to provide nonlinear attenuation to compress all signals above approximately 1 Volts and alternating current (AC) couple the signal into the analog to digital converter (ADC) for ADC conversion. The final component before the ADC is a voltage level shifter 206, as indicated by R2 and R3, that puts the signal in the appropriate voltage range for the ADC (e.g., typically between +/−0.5V to +/−2V). As described above, this circuitry is configured to be retrofitted to an existing transmit-only histotripsy driving system. For example, separate circuitry boards can be added and connected to the existing transmit circuitry to add the receive functions. In one embodiment, the receive circuitry is added in parallel to the transmit electronics and passively receives signals without affecting the transmit electronics.

Figure 2B:
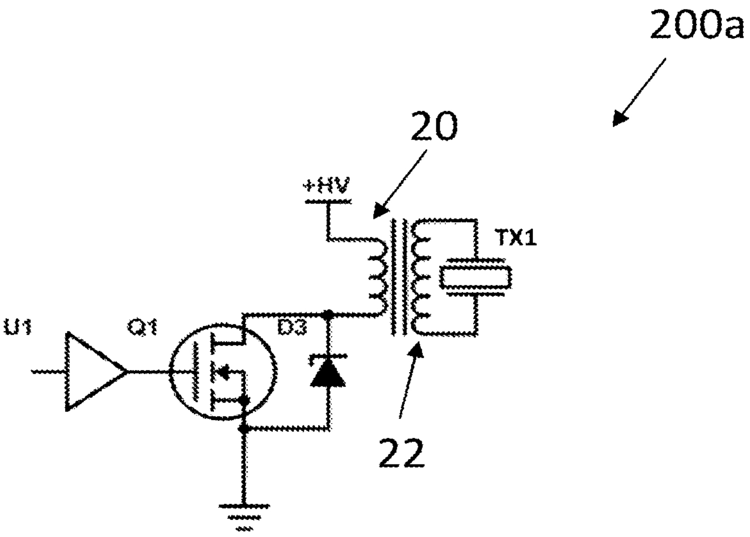

FIG. 2B is one embodiment of a drive circuitry 200*a* that is integrated into high voltage histotripsy driving electronics. In the embodiment of FIG. 2B, a bank of capacitors (not shown) in series with the primary coil 20 of the transformer are charged by a high voltage supply. A driver chip, U1, then triggers the n-channel MOSFET transistor, Q1, which sends a high voltage AC pulse through the transformer primary coil thereby generating an AC pulse in the transformer secondary coil 22 with a voltage proportional to the turn ratio between the coils. The secondary coil can be electrically coupled to each of the transducer elements (in this illustration, transducer element TX1). In one implementation, a turn ratio of approximately 1:3 was used between the primary and secondary coils. This receive drive circuitry is thereby able to generate single-cycle pulses at the center frequency of the transducer on the order of 3 kV. It should be understood that other turn ratios can be implemented.

Figure 2C:
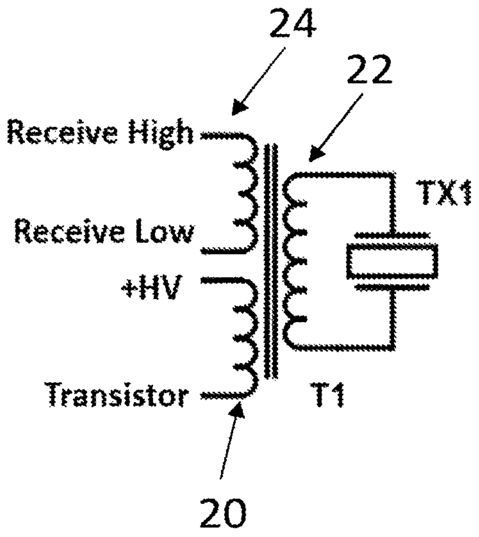

Referring to FIG. 2C, another embodiment of receive drive electronics for a histotripsy system are shown. As shown, the receive drive electronics can include a secondary transformer coil 22 coupled to the transducer element TX1. Because the driver for this system already includes a transformer at the output of each channel, a third coil 24 can be added to each transformer to be used for the receive electronics, thereby providing total isolation between the driver (e.g., the primary coil 20) and the receiver (e.g., third coil 24). In one implementation, the receive or third coil can be wound with approximately 10-times fewer windings than the secondary transformer coil 22, thereby providing a 10×reduction in voltage between the secondary coil and the third coil. The number of windings on the tertiary or third coil can be tuned for the specific application and need not necessarily be 10-times fewer than the secondary. The ratio depends on the receive signal amplitude and can be adjusted based on desired voltages. In one embodiment, the receive winding (third coil 24) from FIG. 2C can be coupled to a second transformer designed for small signal use with the specifically chosen core material and size such that it would be configured to saturate during the transmit pulses to protect the analog to digital circuitry (ADC) behind it. When receiving signals, however, the second small signal transformer would be configured to not saturate, thereby enabling the appropriate gain and sensitivity for the received signals.

Figure 2D:
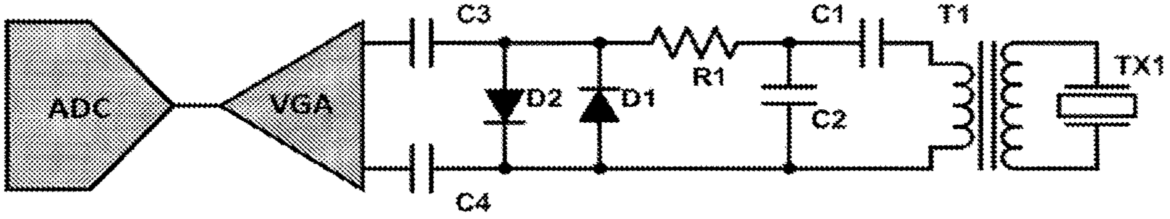

A schematic design of receive circuitry for the integrated receive-capable histotripsy system is shown in FIG. 2D. The primary difference in the embodiment shown in FIG. 2D compared to the embodiment above in FIG. 2A is the transformer, which is described in the embodiment of FIG. 2C. The VGA circuit is added in the embodiment of FIG. 2D, and the "balanced" input with the two capacitors C3 and C4 in series instead of the level shifter as shown in FIG. 2A comprises a digitizer.

In another embodiment, the transmit-receive drive circuitry can include a transmit-receive switch. An integrated drive-receive circuitry with both transmit and receive circuitry on the same board can use a switch to separate the receive signal from the transmit signal. For example, a traditional TR switch with diodes blocks high-voltage transmit signals without attenuating receive signals. A circuit with different linear gain can follow the switch to amplify or attenuate the selected portion of the receive signal properly based on its amplitude to maximize the sensitivity. However, this design would waste a lot of power, be large, and expensive.

Figure 3A:
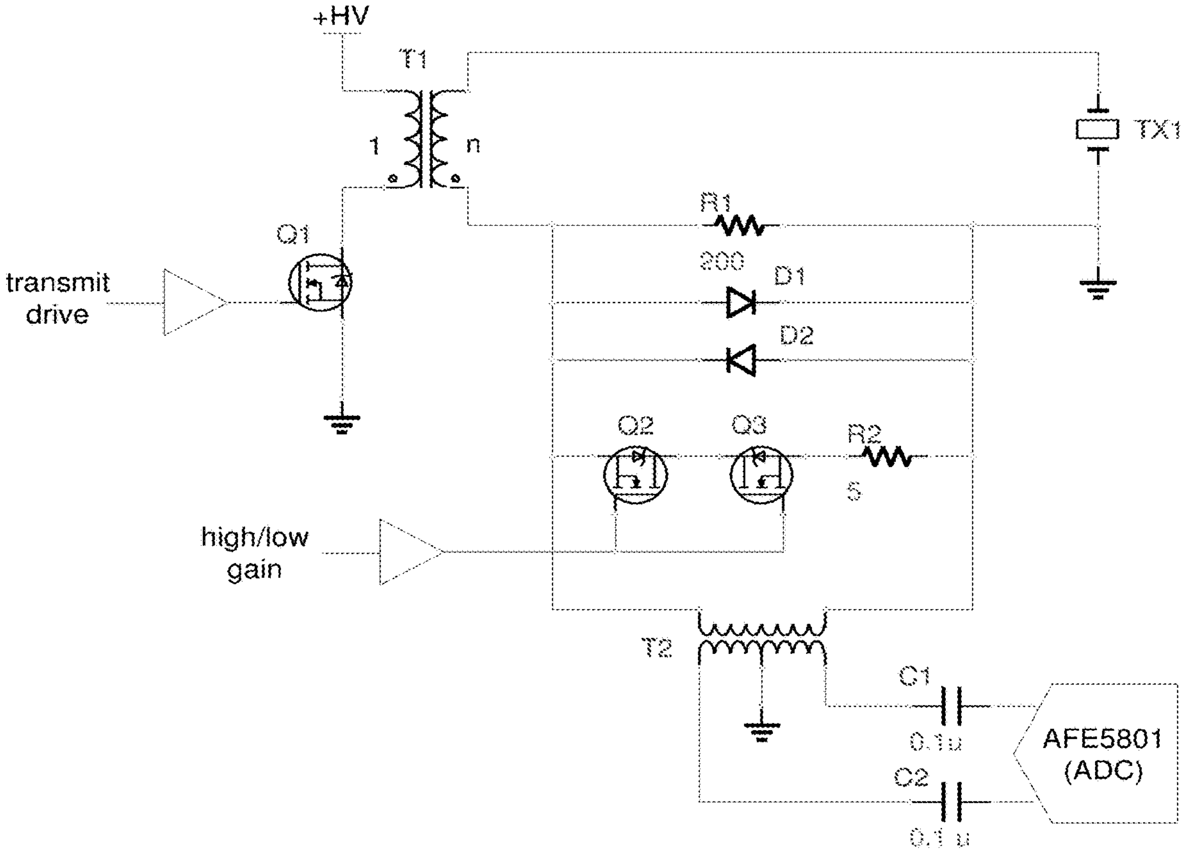
FIGS. 3A-3C are embodiments of current sense electronics for a histotripsy system.

FIG. 3A illustrates another embodiment of drive-receive circuitry that is configured to measure current flowing back from the transducer TX1 through the drive transformer T1 (instead of measuring voltage generated on the transducer during receive as discussed above). The relatively large surface area of therapy transducer array elements compared to a traditional imaging transducer means the transducer array generates a relatively large current, which makes high sensitivity during receive possible, whereas with an imaging transducer, it is only practical to measure the voltage induced by acoustic signals. Normal ultrasound imaging elements would be too small to generate a useable receive current. Therapy elements as described herein are hundreds to thousands of times larger in surface area than traditional imaging elements, so the currents are substantially larger and easy to measure (in the milliamp range rather than microamp). In the circuitry illustrated, current can be measured by a sense resistor in the electrical path (R1). The drive-receive circuitry is configured to pass excess current from large reflections or during the transmit pulse through a set of bypass diodes (D1 and D2). Transmit currents can be as large as 40 A. While the drive-receive circuitry is receiving reflections such as ultrasound reflection signals and/or acoustic cavitation emissions, the sense resistor is configured to measure a current induced in the circuitry by those reflections. Voltage generated across the current sensing resistor is coupled to the ADC through a Balun (T2) and Capacitors C1 and C2. This balanced input configuration is the manufacturer's preferred circuit for the AFE5801 digitizer. Single-ended operation would also be possible for this or other digitizers by directly measuring the voltage on R1 with respect to ground.

The drive-receive circuitry of FIG. 3A can be configured to operate in a low gain mode and a high gain mode. Referring still to FIG. 3A, the circuitry can have two current sensing resistors R1 and R2 so that the overall sensitivity of the circuit can be changed by a large amount. As shown, this can be implemented with a pair of transistors Q2 and Q3 that are configured to switch on/off a small value resistor R2 (low sensitivity) in parallel with the larger value resistor R1 (high sensitivity). The resistance of the circuit can be changed very rapidly with these transistors to enable the use of both the low setting over part of a received burst of data (e.g., a received signal with a higher amplitude such as ultrasound reflection signals from bones) and the high setting a few microseconds later (e.g., a received signal with a lower amplitude such as acoustic cavitation emission signal from cavitation collapse). Because the sensor is directly changed, both scales have very high SNR unlike a variable gain amplifier where the SNR is usually worse for higher gain. In some embodiments, additional sense resistors can be implemented in the same manner for even wider dynamic range. For the circuit shown in FIG. 3A, the high gain mode is configured to measure currents up to 5 mA in the ADC which is coupled to the circuitry via transformer T2, while the low gain mode is configured to measure currents up to 200 mA in the ADC.

Figure 3B:
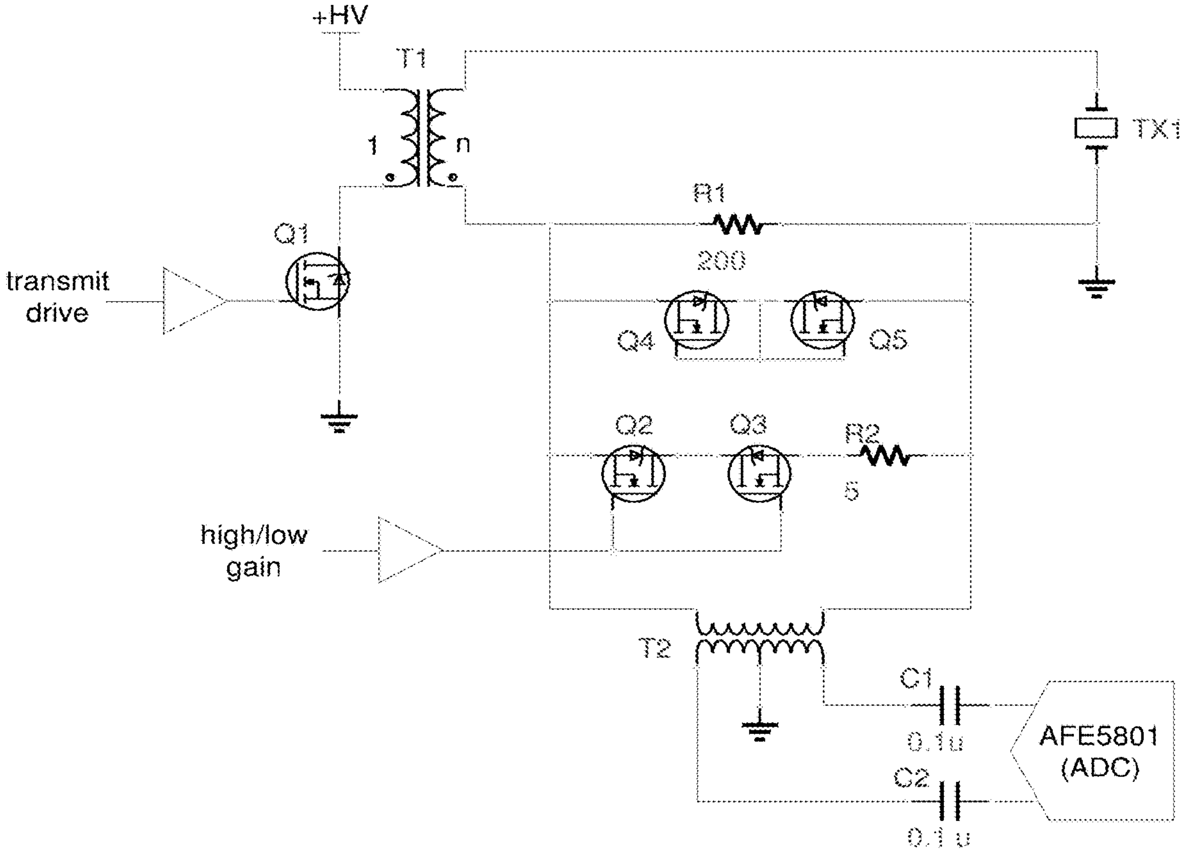

FIG. 3B shows an alternate embodiment where instead of bypass diodes, low gate threshold MOSFET transistors Q4 and Q5 can be implemented for passing the large transmit currents. With the advances in transistors, there are now transistors that are smaller, cheaper, and higher performance than any diode for this bypass role. These transistors can have a higher turn on voltage than a single diode, which allows the use of the full dynamic range of the ADC more easily.

Figure 3C:
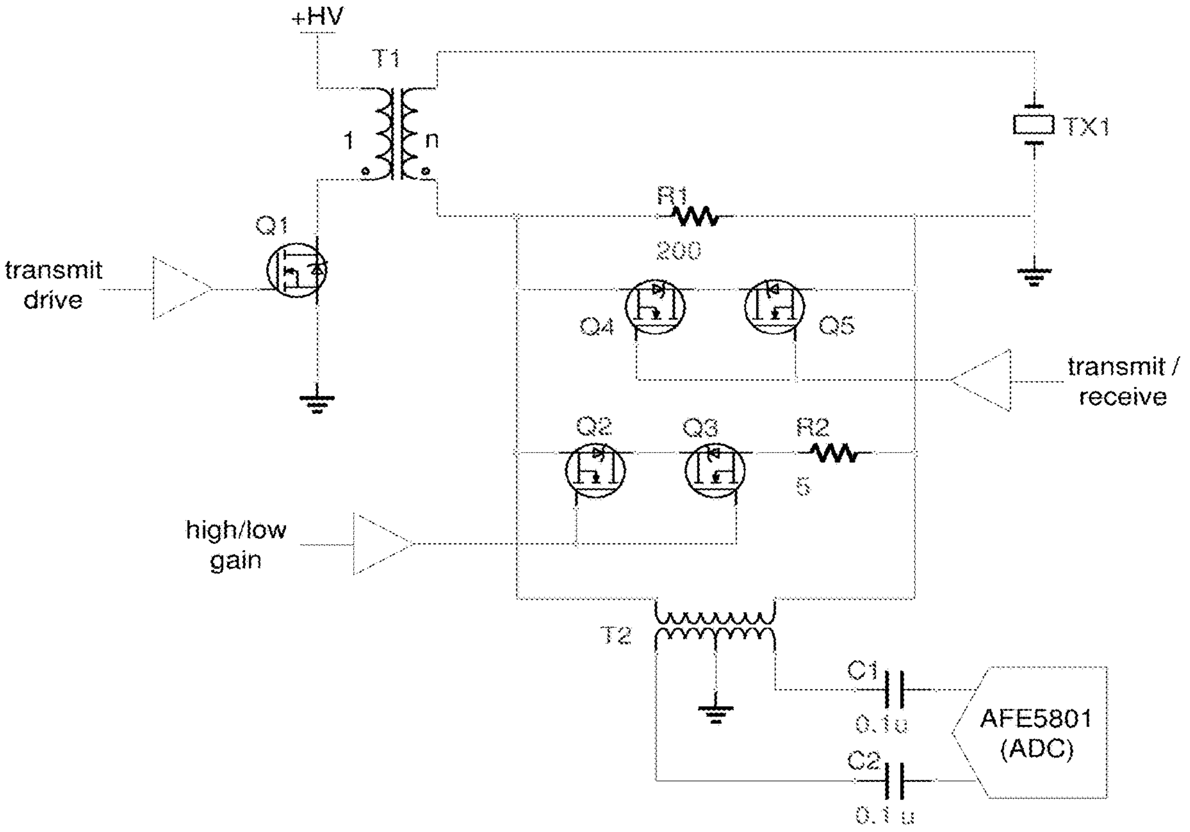

FIG. 3C shows a third embodiment where the bypass transistors Q4 and Q5 are explicitly controlled as an active transmit-receive switch. The transistor gates are connected to a gate drive signal to force the transistors fully on (for transmit mode) or fully off (for receive mode) which could be +/−5 V, for example, depending on the transistor drive requirements. This configuration may reduce RF noise generated during transmit where instead passively switched bypass components must turn on and off rapidly at the frequency of the ultrasound. This design has a tradeoff of a minor increase in complexity.

The analog received signals described above can be converted to digital signals and then collected and processed. The signal received from the histotripsy transducer array can be, for example, reflections from bones or soft tissue or acoustic emission signals from cavitation. These signals are typically received in a specific time window after the histotripsy pulse (e.g., tens to hundreds of microseconds after transmission of the therapy pulse(s)). Thus, the hardware and software described herein is configured to synchronize the time clock of transmit, receive, and ADC conversion and sampling to obtain the appropriate time window after each histotripsy pulse that contains the desired received signals. If the synchronization and time window is set properly, then the desired received signals can be collected and processed.

To achieve proper synchronization and time windowing, any of the transmit-receive drive electronics described herein can include an embodiment in which a single field-programmable gated array (FPGA) device connected to the ADC can be used to control both the transmit and receive operations of the transducer, as well as the ADC for some subset of or all channels of a histotripsy system. By providing the FPGA with a single clock off of which the timings of the operations to be executed by the separate subsystems are based, synchronization between subsystems can be guaranteed especially when multiple FPGAs are used to control various subsets of histotripsy transducer elements. Setting the appropriate time window to receive the signals can then be achieved through appropriate assignment of the timings of the respective operations when programming of the FPGA. In cases where multiple FPGAs are required, for instance in arrays with too many transducer elements to control from a single device, a single clock line can be fanned out to all of them for synchronization, and a centralized 'master' FPGA can be used to trigger the execution of their operations within the appropriate time window.

Alternatively, any of the transmit-receive driving electronics described herein can include multi-FPGA systems can be setup to run in a 'headless' mode wherein no centralized 'master' FPGA is required to issue/fan out a single shared clock line or trigger the execution of individual boards' operations. In such a mode, each FPGA would be set to run off of its own individual clock and to monitor and update two common 'program-execution-state', and one common 'execute-operation', open-drain hardware IO lines shared by the whole system. The open-drain lines operate such that, if any single FPGA applies a low signal to the lines, the signal measured anywhere on the line would register low; if and only if all FPGAs apply a high signal to the lines, the signal measured everywhere on the line would register high. The two 'program-execution-state' lines would be used to the FPGAs to issue system-wide 1) 'ready-to-execute' and 2) 'done-executing' signals and by default each FPGA would apply a low signal to each of these lines; each FPGA would apply a high signal to the 'execute-operation' line. While running a program, upon reaching a new executable instruction in the program, each FPGA would update the 'ready-to-execute' line to apply a high signal to it, and enter a wait state wherein it would monitor the signals on both the 'ready-to-execute' line and the 'execute-operation' lines. Once all FPGAs reached the 'ready-to-execute' state, the signal registered on the 'ready-to-execute' line would become high; the first FPGA in the system to detect a high state on the 'ready-to-execute' line would issue a low signal on the 'execute-program' line causing it to register low everywhere. Upon detection of the low signal on the 'execute-program' line, each FPGA would set the value on its own terminal of the 'execute-program' line to be low and execute its stored commands. Once each FPGA finished running its respective commands, it would apply a high signal to both the 'done-executing' and 'execute-program' lines. Once both the 'done-executing' and 'execute-program' lines registered high, the FPGAs would reset all of the shared open-drain line values to their defaults, load the next instruction in the program, and repeat the process for each instruction until the program was completed.

A fully connected set of receiving elements can generate large amounts of data, so strategies to reduce the data load are proposed to allow acquired signals to be transferred and processed in real-time to meet the monitoring needs during therapy. These strategies can be applied to any of the transmit-receive driving electronics described herein. Such strategies may include, for example, artificially down sampling the incoming data from the ADC in the firmware running on FPGA (e.g., by storing only every other data point generated by the ADC, or the average of the data points generated across multiple acquisition cycles). This effectively reduces the sampling frequency, thus reducing the data load, but doesn't sacrifice temporal precision or dynamic range or result in an increase in noise in the system. Differential compression schemes, wherein all data captured after the first time point is stored as the difference between the values captured at adjacent time points may also be applied. For example, for a value at time 1 of X, and at time 2 of Y, one could store the value of the difference between Y and X, D=Y−X, at time 2 instead of the value of Y directly, and then calculate the actual value of Y during processing as Y=X+D. In this way, nominal values of say X=64000 and Y=63900, which combined represent 4 bytes of data, could be stored as X=64000 and D=−100, which combined represent 3 bytes of data and allow the full recovery of the value of Y. As the length of the data record gets longer, this compression strategy results in data reductions proportional to ratio of the size of the variable needed to store the difference value compared to the size of the variable required to store the actual value, which can generally reduce data loads in the current system by 30%-50%, but could result in significantly larger reductions in systems where the individual data elements are larger in size. In applications not demanding real-time processing/compression, further reductions in data size can be achieved through frequency domain transforms using methods similar to those employed to compress audio files.

As some of the events that need to be monitored during histotripsy therapies will require very high temporal precision (e.g., the signals from individual cavitation events), while others will require little precision (e.g., the reflections of signals off of large boundaries, e.g., the skull, ribs, tissue interfaces), strategies to dynamically alter the compression ratio can be implemented to fully utilize the incoming data for real-time applications. To that end, the firmware and software that control the data acquisition have been configured such that the sampling frequency and compression strategy used during acquisition can be set on a per-channel basis in the array, and can be independently updated in real-time, even in the middle of an individual acquisition event. This allows for different sub-apertures of the array to be set up to monitor different features of the therapy at the requisite sampling frequency and compression settings, as well as for the receive system to be set to the maximum sampling frequency/minimum compression settings across all elements of the array as needed to monitor short-lived events with potentially weak signals, and then set back to lower sampling frequencies with higher compression settings outside the window requiring maximal monitoring. This allows short-lived events of this type to be fully monitored without necessitating cut-offs in the acquisition to reduce the data load which could otherwise potentially result in reducing the physical size of the actively-monitored field or drastic reductions in monitoring speed during therapy.

In some situations, the receive signal amplitude may be low and the noise may be high, resulting in a low signal-to-noise ratio (SNR). One method to reduce the noise and increase SNR is to oversample and average in firmware (e.g., FPGA firmware) before storing data. This also helps increase dynamic range and reduces memory requirements. Another technique is to implement a dynamic variable sample rate. For example, the ADC can be configured to always run at 50 MHz, but high time precision may only be needed over certain portions of the data record. In the portions of the signals where such a high frame rate is not needed, samples can be decimated or averaged to greatly reduce storage requirements.

The bandwidth of the therapy transducer elements is typically low, but a high sampling rate can be used for sampling for good timing precision. Receive data should compress exceptionally well in the Fourier domain (at least a factor of 10, maybe a lot more). The FPGAs can be configured to perform this compression before storage or transmit either in firmware or in software. Data compression is the key to implementing real time monitoring, the system will be overwhelmed by the amount of receive data collected.

In applications where real time monitoring is not essential, or where treatment speed needs to remain higher than possible while simultaneously transferring the full acquired signals to the user's computer after each pulse, the system can be configured to transfer only partial signals and/or store the acquired signals directly on the FPGA devices themselves for transfer to the control computer later. This would allow uninterrupted acquisition of signals from all delivered pulses without limiting treatment speed. Such capabilities are useful for monitoring long-term changes in acquired signals. For example, there is inherent variability in the ACE signal features associated with the ablative state of the targeted tissues that make the tissue state difficult to track pulse-to-pulse, but characteristic changes in the ACE signals exist over longer treatment time scales (e.g., >20 applied pulses) that allow the ablative state of the tissue to be assessed. One could transfer partial signals in real time to allow localization and mapping of the cavitation events on a per-pulse basis, while storing larger-record length signals on the FPGA to be transferred intermittently to assess the state of the ablation in the therapy target.

In some situations, it is possible to generate focal pressures far in excess of twice what is nominally required to generate cavitation during therapy and in such cases it may be possible to generate cavitation using fewer than half of the histotripsy transducer array elements. The software controlling the histotripsy array allows for the elements of the array to be easily partitioned into independently controllable sub-apertures, effectively allowing a single physical histotripsy transducer array to be operated as multiple separate histotripsy arrays. In this way, multiple locations within the focal volume can be targeted for treatment concurrently using the separate sub-apertures of the array, allowing for increases in treatment speed without necessitating an increase in the rate at which pulses are delivered.

Aberration Correction Techniques

Below are described examples of aberration correction methods and techniques that are new and specific for histotripsy therapy.

One embodiment of aberration correction enabled by transmit-receive histotripsy arrays utilizes the arrival time of robust shockwaves emitted by the initial rapid expansion of histotripsy-induced cavitation bubbles. This can be referred to as acoustic cavitation emission (ACE) signals. This shockwave construct emanates spherically from the focal cavitation region back toward the histotripsy therapy array. Any aberrations in the propagation path can be determined by calculating the travel time from the focal cavitation site to each histotripsy array element. After processing the arrival time of the ACE signal received by each element, a correction time delay for each element can be applied to subsequent transmissions for each respective transducer element, such that the ultrasound pulse wave generated by each histotripsy array element will arrive at the focal cavitation position at the same time. This is done by applying the variation in time-of-flight for ACE signals to the transmission pulse signal to each histotripsy array element, such that the transmission signals would arrive at the cavitation site at the same time, correcting the aberration and improving focusing.

Figure 4:
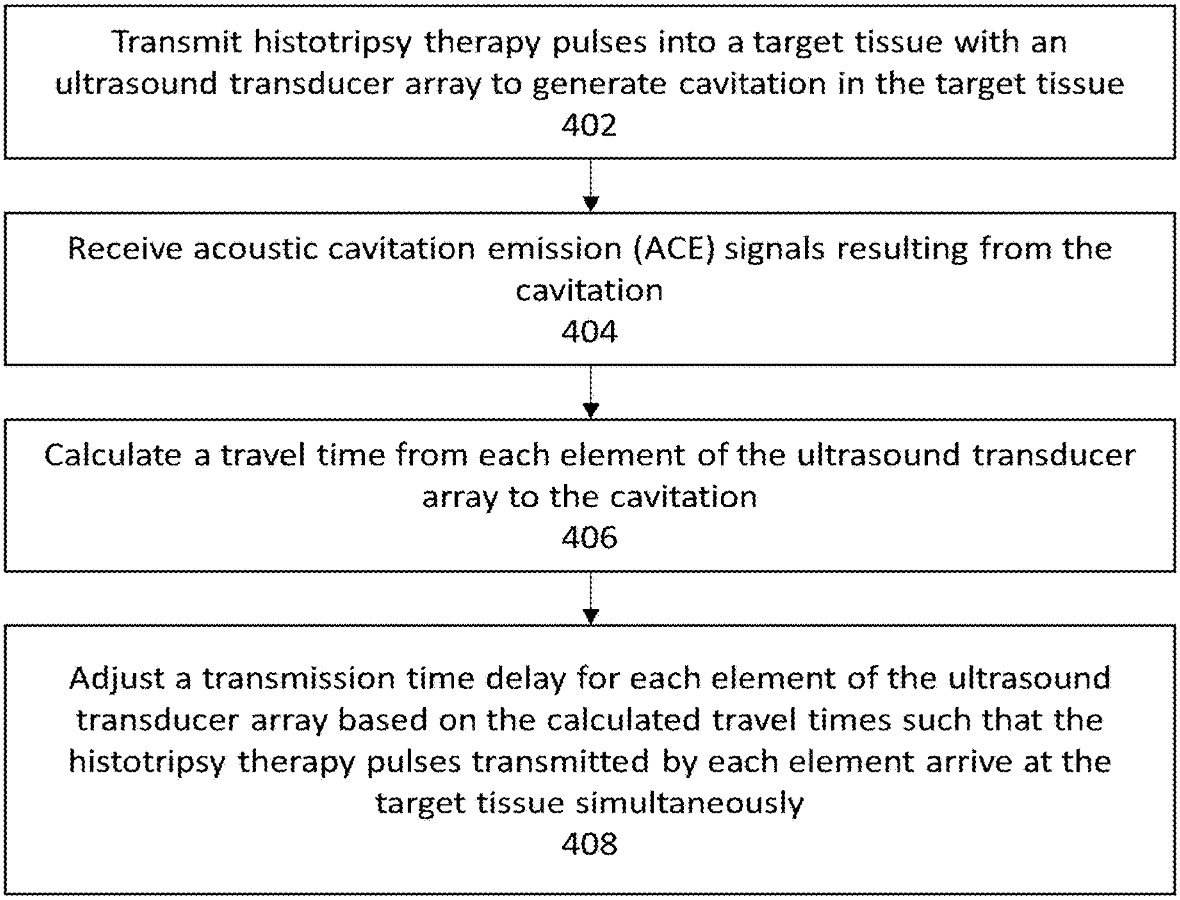
FIG. 4 is a method of providing histotripsy therapy to a patient.

For ACE-based aberration correction, a specialized method and algorithm illustrated by the flowchart in FIG. 4 can be implemented that includes the following operations: At step 402, the method can include transmitting histotripsy therapy pulses into a target tissue with an ultrasound transducer array to generate cavitation in the target tissue. As described above, a plurality of transducer elements of the array can each transmit separate histotripsy pulses into the tissue. Next, at operation 404, the method can include receiving acoustic cavitation emissions (ACE signals) resulting from the histotripsy-induced cavitation. The receiving of ACE signals can utilize, for example, any of the systems or drive electronics described above. Next, at an operation 406, the method can use the information encoded in these ACE signals (e.g., start time of the emission generated from cavitation bubble expansion, peak time from cavitation bubble collapse) to calculate the travel time from each element of the histotripsy array to the cavitation in the target tissue. Finally, at operation 408, the method can include adjusting the time delay of the driving electric signal to each array element to correct for the difference in the travel time, such that the ultrasound pulse delivered by each element are configured to arrive at the focus/target tissue at the same time in subsequent transmissions. This method can be used for aberration correction with bones or heterogeneous tissue in the pathway.

Although the method described above discusses receiving ACE transmissions from the rapid expansion of cavitation, the same technique can be used to receive the acoustic shockwave/signals from the cavitation bubble collapse. The signals from the cavitation bubble collapse received by each array element can be used similarly as the cavitation expansion signals to calculate the time-of-flight for aberration correction as described above.

Shockwave pressure tends to increase linearly with increasing histotripsy focal pressure. One embodiment of the time of flight analysis of these shockwaves involves using the Hilbert transform to calculate an envelope of these shockwaves. A cross-correlation algorithm can then be used to determine the temporal shift required to realign these envelope signals. These temporal shifts are then inverted to correct for variations in time-of-flight across histotripsy elements and are then applied to subsequent pulses as described above. Other methods for analyzing these signals include detecting the peak shockwave pressure or using a window-averaging filter and edge detection algorithm to determine the arrival time of shockwaves. Without aberration correction, the focal pressure at a sub-cavitation threshold amplitude is found to drop to 49.7%, and the transducer power required to induce cavitation triples. Using the ACE aberration correction methods described above, over 20% of the lost pressure can be recovered, and the transducer power required to induce cavitation can be reduced by approximately 31.5%.

Acoustic cavitation emission (ACE) signals may not always be detectable (e.g., due to attenuation effects from propagating through tissues/bone) and/or differentiable from background signals components (e.g., the ACE signals may arrive at the array elements concurrent with histotripsy pulse reflections/reverberations) at sufficient levels to perform aberration correction. In such cases, using the cavitation events as the basis for aberration correction may be achieved using pulse-echo techniques by partitioning the histotripsy array elements into multiple sub-apertures, one of which would be used to generate the cavitation events (sub-aperture A), the other of which would be used to fire interrogation pulses (sub-aperture B). In this scenario, all elements of sub-aperture A would fire histotripsy pulses with sufficient amplitude to generate the cavitation event at the target, say at time=0. At some time later when the generated cavitation event would have grown in size, say at time=100 us, the elements sub-aperture B would fire pulses directed towards the event. Upon reaching the cavitation event generated by sub-aperture A, the pulses from sub-aperture B would be reflected off of the cavitation event and scattered back towards the array. The array elements of both sub-apertures could then be used to receive the signals reflected off of the cavitation event and the arrival timing of these signals could then be used to calculate the aberration correction delays per the methods described in [69] and [70]. A key benefit of this technique is that the timing of the pulses from sub-aperture B can be set arbitrarily such that the reflected/scattered signals arrive back at the array elements for detection in a region of the signal where background components are minimal.

In another embodiment, aberration correction can be based on scatter signals from soft tissue.

A focal dithering method can also be used for aberration correction based on receive signals. The challenge of using scatter or reflection signals from soft tissue is that the amplitude from the scatter signal from a target tissue is often small and/or buried by the background signals of scatter signals from other tissues. The scattered signals with the array focus at the geometric focus are received from all elements of the array ($Sc1_n$, n is the element number). Then the array focus can be dithered to a small distance away (e.g., ½ or 3/2 wavelength) from the geometric focus, and the scattered signals are also received from all elements of the array ($Sc2_n$, n is the element number). Both these signals contain the background scatter signals from all heterogeneous tissue in the pathway should, while the difference ($Sc2_n-Sc1_n$) is only due to the scatter signal from the dithered focus with the opposite phase. Combinations of phase or time delays to all elements will be tested to determine a combination of phase or time delays that can maximize the difference ($Sc2_n-Sc1_n$). This resulted combination can then be used for aberration correction. As the speed of sounds difference between tissue is small, the variations in time-of-flight due to the heterogenous soft tissue path across elements are expected to be small. Thus, a pre-set of combinations of delays can be calculated beforehand to use for testing. This method allows aberration correction without generating cavitation and potentially maintaining a good enough SNR for processing.

For ultrasound therapy, water is often used as a coupling medium to ensure ultrasound transmission from the transducer array to the skin of the patient. The speed of sound difference between water and soft tissue can result in a substantial location shift of the focus (e.g., a few millimeters). Reflection signals from the water-skin interface can be received by each array element to determine the time-of-flight from each element surface to the water-skin interface, and use that time-of-flight determination to correct for the focal shift caused by the coupling medium.

Reflection signals from bone can have high amplitudes. The methods and algorithms described herein can also include detection of transducer elements blocked by ribs (via high amplitude reflected signals) and turning off these transducer elements, or reducing the amplitude of the transmission signals to these transducer elements (amplitude aberration correction) to reduce the potential of rib or bone heating during histotripsy treatment.

The reflection signals from various tissue surfaces and layers may be received by each array element to model the tissue layers. Based on the speed of sound of each tissue layer using a literature value, the time-of-flight from each element to the array focus may be calculated for aberration correction. This method would only provide a coarse aberration correction.

Cavitation Localization and Mapping

The ACE signals received by the transmit-receive histotripsy transducer array, described above, can be used to localize and map the cavitation in the target tissue. With the known locations of each histotripsy transducer array element, conventional beamforming methods used in ultrasound imaging and passive cavitation mapping can be used. However, to image cavitation behind bone or other aberrators, such as the ribs, through the skull, or through deep-overlying tissue, because the speed of sound in the path for each element may vary, modifications to existing beamforming or passive cavitation mapping algorithms are required and discussed herein to account for the travel time variation for different elements to arrive at the focus. The travel time difference can be accounted for using iterative methods to maximize the signal amplitude within the focal cavitation region after beamforming.

For example, a brute force method can be used to test a range of ultrasound travel time delays iteratively for all histotripsy array elements. The combination of time delays that results in the highest amplitude of the summed-together ACE signals can then be used for cavitation localization and mapping. This can be achieved sufficiently fast for real-time imaging. The example below shows a frame rate of 70 Hz for cavitation localization through an excised human skull with accuracy within 1.5 mm based on the transmit-receive histotripsy system and the brute force method. It should be noted that the same method can also be used to obtain mapping of the skull surface or ribs that are in the pathway, as the strong reflection signals from the bone can be received by the histotripsy array and separated for processing.

Example: transcranial cavitation localization and mapping. In this example, a brute force iterative method can be used to localize cavitation through the human skull. The same method can be applied to generate cavitation mapping through the ribs to monitor cavitation behind the ribs. Cavitation localization and mapping are accomplished with the following two steps: 1) signal processing to separate the ACE signals from the skull reflection signals; and 2) generating a cavitation map by projecting the ACE signals acquired by each element of the array back into the field and summing their signal amplitudes.

Signal processing to separate the ACE signals from skull reflection signals can include three basic steps. First, low amplitude, sub-cavitation threshold histotripsy pulses can be delivered to the target tissue, and the reflections of the pulses off the intervening tissue can be recorded using the transducer array elements. These signals can then be scaled up and subtracted from the ACE-containing signals generated after delivering high-amplitude histotripsy pulses in order to isolate the ACE signals from the background. Next, the signals can then be smoothed using a moving window average to reduce spurious effects of noise in the acquired signals on the localization results. The magnitudes of the signals can then be taken as a precondition for a localization algorithm.

Localization and mapping of cavitation events can be accomplished by brute force, iterative methods by projecting the acquired ACE signals back into the field to generate volumetric maps of the projected signal amplitude with the focal region of the transducer. The volumetric maps used in the computations can be generated on grids of voxels centered at the expected locations of the cavitation events in the field. Based on the known locations of the histotripsy transducer elements, and their distances from each voxel in the volumetric grid, the there-and-back times-of-flight of acoustic pulses propagating between the voxels and transducers can be calculated under the assumption that the speed of sound is constant everywhere between them, and having a known speed of sound constant. The signal amplitudes measured from each transducer at the corresponding times at each respective voxel can then be summed together to determine the sum signal amplitude at each voxel. To account for the fact that the sound speed between the transducers and voxels is not constant due to the presence of tissue between them, the process of selecting the time points within the acquired ACE signals from which the measured signal amplitudes were taken can be repeated by iterating in time about the calculated there-and-back times-of-flight at each voxel element and recalculating the signal amplitude field at each time step. The sum signal amplitude at each voxel at the end of the iterative calculations can be taken to be the maximum value calculated at each voxel within the whole iteration window. This process accounts for the combined effects of the tissue sound speed and thickness on ultrasound propagation by considering only the end result, which in this simplified case is to produce a uniform modulation of the signal arrival times at the transducer elements. This greatly reduces computational complexity and allows the effects of tissues to be accounted for during the localization process through iterative time shifting operations. The locations of the cavitation events can then be calculated by finding the center-of-mass of all points within the voxel grid whose amplitudes were >90% of the maximum detected value.

Using this method, 3D cavitation localization can be achieved through bone, such as through ribs or through a human skull. The ACE feedback localization results are accurate to within ≤1.5 mm of the actual positions of the generated cavitation events' centers-of-mass (as measured through optical imaging). Taking into account the physical sizes of the bubbles, localization results have been found to fall within <1 mm of the volumes encompassed by the bubbles in >90% of cases. Localization of cavitation in real-time at rates of up to 70 Hz has been achieved during experiments using the described methods, but benchmark tests indicate that the localization algorithm scales efficiently and thus higher rates are likely possible with more powerful hardware.

Figure 5:
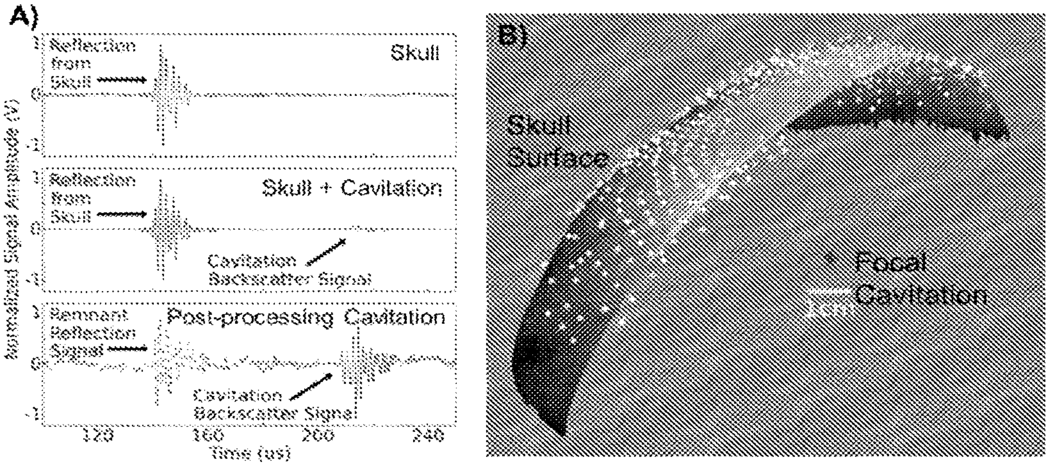
FIG. 5 illustrates cavitation mapping through bone such as a human skull.

Referring to FIG. 5A, signals received from each element of the transmit-receive histotripsy array are shown, including the reflection signal from the skull at a sub-threshold cavitation pressure, the skull reflection signal and the ACE signal at a supra-threshold cavitation pressure, and post-processing ACE signals acquired by subtracting the skull reflection signal. FIG. 5B illustrates a skull surface map and the focal cavitation localization/map produced by processing the ACE signal using the brute-force iterative method.

In another embodiment, the method described for mapping transcranial cavitation is extended for use in applications where targets lie below highly non-uniform aberrators (i.e., the ribs) or where path length variations through tissues en route to the target are significant (e.g., when the transducer must be obliquely aligned with respect to the tissue surface in order to focus at the target). The same signal processing and localization methods as described above can be applied with two important additions.

Signal Processing: An additional step in the signal processing may be required to account for the presence of non-uniform aberrators and oblique surfaces. First, each element of the array is fired individually, and the reflections of the pulses off of the tissue(s) are recorded by all array elements. Given the known positions of the transducer elements and sound speed of the coupling medium, traditional delay sum beamforming can be used to generate a 3D map of the tissue surface and underlying features (i.e., the ribs) from the acquired signals.

2) Cavitation Localization and mapping: Given the known surface geometry of the tissue, and/or locations of underlying features such as the ribs, non-uniform delays can be applied to the ACE signals acquired during the time-iteration process used to localize the cavitation events. In the case of ribs, based on their known positions, the delays assigned to the ACE signals known to propagate through ribs can be assigned a fixed offset with respect to those that don't, in order to maximize the projected signal amplitude in the field to localize the cavitation event. Or, given the known surface geometry of the tissue with respect to an obliquely aligned transducer, the time-delays assigned to each element can be set in a graduated way to account for the different path lengths of tissue through which the ACE signals would need to travel in order to reach each array element.

In another embodiment, the methods described are extended for use in applications where targets lie within an approximately uniform aberrator (i.e., the liver) whose sound speed may not be well known, particularly where path length variations through tissues en route to the target are significant (e.g., when the transducer must be obliquely aligned with respect to the tissue surface in order to focus at the target). The same signal processing and localization methods as described, as well as method for mapping the tissue surface geometry described above can be applied with the following addition.

Given the known surface geometry of the tissue, sound speed of the coupling medium, and timings of the generated ACE signals, the location of the cavitation events as well as the sound speed of the nucleation medium itself can be determined via minimization of a coupled system of equations through the application of Snell's law describing refraction. Given the known positions of the array elements with respect to the tissue surface, the time of flight from each element to every point on the tissue surface, and the respective trajectories of the pulses with respect to it, can be calculated. Upon exiting the tissue, the trajectory of the ACE signal from the cavitation event will be altered due to the difference in sound speeds between the tissue and the coupling medium per Snell's law. The sound speed of the coupling medium, and distance from the array elements to every point on the tissue surface are known, but not which point on the tissue surface the received portion of the ACE signal acquired by each array element originated from; the sound speed of the tissue and the location of the cavitation event being mapped are also unknown. The timings of the ACE signals at the individual array elements, $t_{ACE,n}$, will only depend on the distance propagated through the coupling medium and the tissue, and their respective sound speeds as $$t_{ACE,n}=[D_{cm,n}/C_{cm,n}+D_{t,n}/C_{t,n}],$$

where the 'D' and 'C' correspond to the 'distance traveled' and 'sound speed of the medium', respectively, and the subscripts 'cm', 't', and 'n' correspond to 'coupling medium', 'tissue', and 'element number' respectively. The values of three of these variables ($D_{cm,n}$, $D_{t,n}$, $C_{t,n}$) are unknown, however, the value of $D_{cm,n}$ becomes immaterial through the enforcement of Snell's law at the tissue-coupling medium boundary because it can be re-expressed purely in terms of the values of $D_{t,n}$ and $C_{t,n}$ once they are known. One can then solve for the sound speed of the medium and the location of the generated cavitation by minimizing the value returned by $\Sigma t_{ACE,n,exp}-t_{ACE,n}$, where $t_{ACE,n,exp}$ is the experimentally measured timing of the ACE signal, through adjusting the values of $C_{t,n}$ and the location of the cavitation bubble in the tissue (which is expressed through the value of $D_{t,n}$).

Real-Time Treatment Monitoring

As discussed above, histotripsy generates cavitation to mechanically fractionate target tissue. With increasing dosage or therapy, treated tissue becomes increasingly soft and eventually liquefied into an acellular debris. As a result, over the course of treatment, the cavitation bubbles generated grow larger, take a longer time to collapse, and eventually the cavitation activity mimics strong cavitation activity in fluid. The cavitation expansion and collapse signals can be detected via the acoustic cavitation emission (ACE) signals received by the transmit-receive histotripsy array, which can then be processed to quantitatively monitor the treatment progression and determine the treatment completion. For example, the time to maximum cavitation bubble growth and bubble collapse time increase over the treatment and eventually saturate when the target tissue is liquefied and the treatment is complete. This increasing trend can be detected by processing ACE via specific algorithms to indicate when the treatment is progressing, and the saturation trend can be detected by specific algorithms to determine the treatment is completed, all in real-time. Examples of such algorithms might include using peak detection in the acquired waveforms individually to identify the ACE signals associated with the bubble's growth and collapse, and measuring the timing between them. In cases where signals are embedded within strong background environments, individual waveforms can be processed via autocorrelation to identify the timings between self-similar regions within the waveforms (i.e., the growth and collapse ACE signals). As the background environments of the individual signals would not be equivalent to each other, the ACE signals could then be identified by comparing all of the individual autocorrelation results from each array element with each other, for example by median filtering them, which would show consistent peaks at the time corresponding to the bubble's lifespan. Backprojecting the acquired signals into the field to image for the volume as a function of time would similarly show peaks in the projected signal amplitudes within the image-formed volumes at times corresponding the growth and collapse ACE signals.

Figure 6:
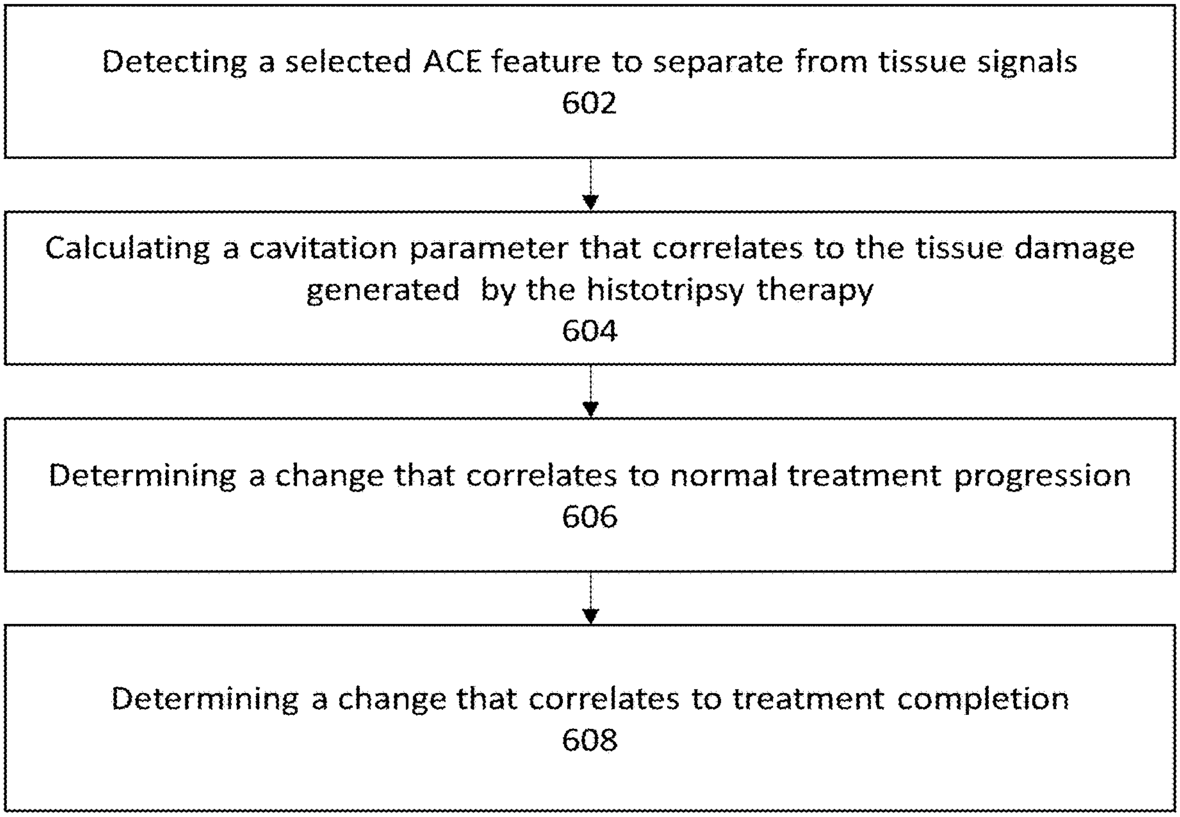
FIG. 6 is a method of providing histotripsy therapy to a patient.

However, the acoustics of these ACE signals are very complicated and can be analyzed in many different ways to obtain desired metrics for treatment progression monitoring. Therefore, specialized algorithms are needed, which include the following functions. Referring to the flowchart of FIG. 6, a method of histotripsy treatment progression monitoring can include, at step 602, detecting a selected ACE feature (e.g., the timings and amplitudes of the cavitation bubble expansion signals, collapse signals, and/or rebound signals) to separate from tissue signals, at step 604, calculating a cavitation parameter (e.g., collapse time i.e., the time between the expansion signal and collapse signal, peak amplitude of the expansion signal, peak amplitude of the collapse signal, amplitude ratios of the growth and collapse ACE signals, or the decay rates of the rebound-associated ACE signal amplitudes) that correlates to the tissue damage generated by histotripsy, at step 606, determining a change (e.g., increasing slope of the selected cavitation parameter) that correlates to normal treatment progression, and at step 608, determining a change (e.g., saturation of the change of the selected cavitation parameter) that correlates to treatment completion.

An example of the cavitation parameter collapse time is provided. This example shows that the increase and saturation of the cavitation collapse time is correlated with the treatment progression and completion. The change in the collapse time ($t_{col}$) of the cavitation bubble cloud over the histotripsy treatment is an indicator for progression of the tissue fractionation process during the histotripsy treatment.

Figure 7:
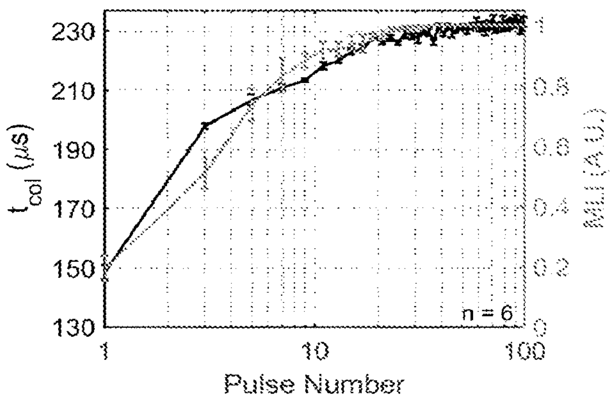
FIGS. 7-10 illustrate data collected via received ultrasound signals from histotripsy therapy to predict treatment progress and tissue fractionation.

In an experiment, 500-kHz, 112-element histotripsy array was used to generate single-location lesions within tissue-mimicking agar phantoms of varying stiffness levels as well as ex vivo bovine liver samples. Cavitation collapse signals were received, and cavitation was imaged using a high-speed camera in transparent tissue-mimicking phantoms. The high-speed-camera-acquired measurements of $t_{col}$ optically validate the acoustic hydrophone measurements. Increases in $t_{col}$ are observed both with decreasing phantom stiffness and throughout histotripsy treatment with increasing number of pulses applied. The increasing trend of $t_{col}$ throughout the histotripsy treatment correlated well with the progression of lesion formation generated in tissue-mimicking phantoms (R2=0.87) (FIG. 7). Referring to FIG. 7, $t_{col}$ (left y-axis) and mean lesion intensity (MLI) (right y-axis) vs. pulse number throughout 100 pulses are shown. The MLI, defined as the average pixel intensity over the ROI, was calculated for the entire treatment on a normalized scale from 0 to 1 to indicate the treatment progress (0—no treatment; 1—treatment completion). The majority of changes in $t_{col}$ and MLI occur early in treatment and at the same time. The change in $t_{col}$ is greater than the change in MLI in the first several pulses, but both metrics even out quickly and reach a plateau threshold around 40 pulses.

Figure 8A:
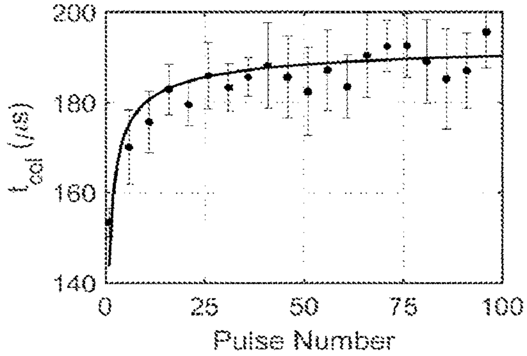
Figure 8B:
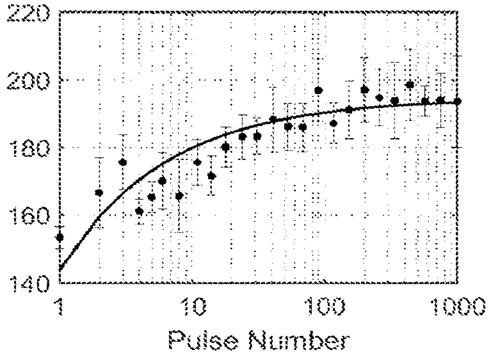

Finally, the increasing trend of $t_{col}$ over the histotripsy treatment was validated in ex vivo bovine liver. The $t_{col}$ experienced an overall average increase of approximately 50 μs throughout treatment, and it reached this steady-state value around 40 to 50 histotripsy pulses (FIGS. 8A-8B). In FIGS. 8A-8B, collapse time $t_{col}$ for first 100 pulses (right, linear scale) and 1000 pulses (left, log scale) in ex vivo bovine liver (n=4) are shown. The majority of the change in tcol is observed within the first 100 pulses of treatment with little to no change between pulse 100 and pulse 1000.

Figure 9:
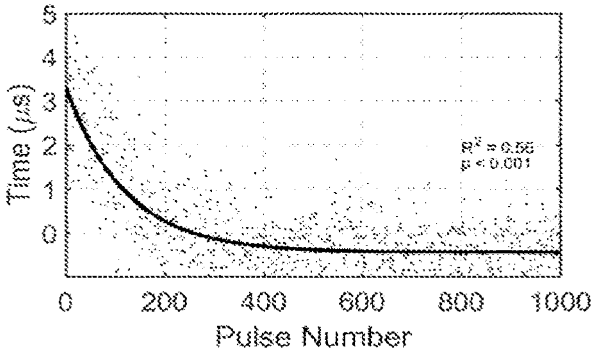

The acoustic cavitation emission (ACE) signal generated by the cavitation cloud during histotripsy therapy was also investigated as a potential feedback mechanism for tissue integrity during treatment. A 500-kHz, 112-element phased histotripsy array was used to generate approximately 6×6×7 mm lesions within ex vivo bovine liver tissue by scanning over 219 locations with 30-1000 pulses-per-location. A custom nonlinear voltage compressor was designed and constructed to allow 8 elements of the array to transmit histotripsy pulses and receive ACE signals from the central treatment location within the lesion. The ACE signal was quantitatively analyzed by measuring the change in the peak pressure arrival time throughout treatment. The ACE peak pressure arrival time decreased as the treatment progressed and eventually saturated (FIG. 9). Referring to FIG. 9, quantified ACE using the peak pressure arrival time is shown. The trend exhibited by the peak pressure arrival throughout treatment suggests that the majority of physical changes that influence this metric occur in the first 200 pulses. A nonlinear least squares best-fit line is shown in black. The best-fit line reached an exponential decay time constant at 80 pulses.

Figure 10:
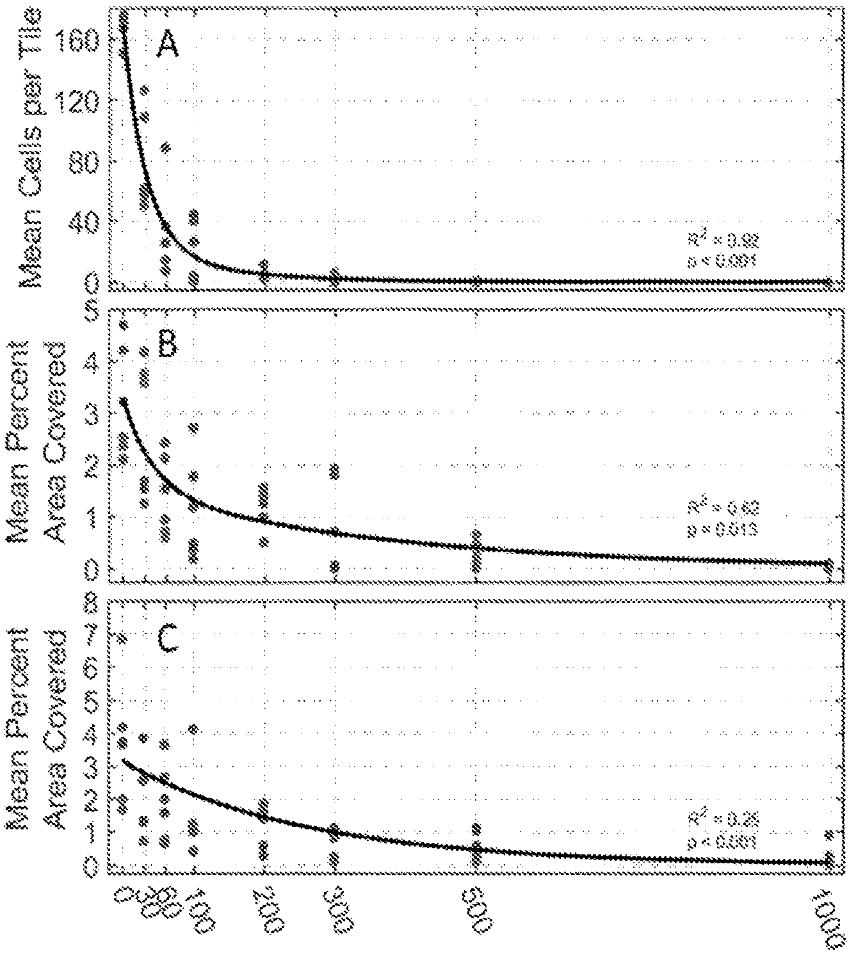

The histology of the treated tissue was analyzed, and correspondingly the cell count, reticulin-stained type III collagen area, and trichrome-stained type I collagen area all decreased over the course of histotripsy treatment (FIG. 10).

Using the Pearson correlation coefficient (PCC), the ACE signal was compared to histological analytics of lesions generated by different numbers of pulses using a significance level of 0.05. Histological analytics included viable cell count, reticulin-stained type III collagen area, and trichrome-stained type I collagen area. It was found that the decrease of the peak pressure arrival time had a statistically significant correlation with the reduction in reticulin-stained type III collagen area with a PCC of 0.72 (p=0.043). This indicates the feasibility of using the ACE peak pressure arrival time as an indicator for histotripsy treatment monitoring. The transmit-receive hardware and software can be significantly improved to improve the sensitivity of this detection. Referring to FIG. 10, a histological analysis of 42 histotripsy treated samples at varying dosages is shown. FIG. 10A shows a viable cell count remaining in imaged medium. The cell count experienced the greatest amount of destruction early in treatment. FIG. 10B shows a percent area with intact reticulin-stained collagen and FIG. 10C shows a percent area with intact trichrome-stained collagen. Both collagen metrics experienced slower amounts of destruction than remaining cell count. Nonlinear least square best-fit lines are shown in red. All best fit lines exhibited statistical significance when compared to a normal distribution as indicated by the p-values on each plot.

The advantages of the transmit-receive histotripsy phased array as described herein can be summarized as following.

1) Aberration correction—Transmit-receive histotripsy can correct aberration due to the speed of sound variation in the ultrasound pathway and improve focusing. As correction needs to be applied to each array element, the correction methods based on the signal received by each element provides the most accurate aberration correction. The advanced transmit-receive histotripsy hardware and software along with the specialized aberration correction algorithms can enable aberration correction on-the-fly immediately before or even during the treatment.
2) Cavitation localization and mapping—As cavitation is the causative agent for histotripsy to generate damage, the real-time, 3D cavitation map can facilitate targeting and treatment monitoring, even with ribs or skull in the pathway. The 3D cavitation map would also allow us to detect both intended cavitation at the target and any potential unwanted off-target cavitation. Therefore, the real-time 3D feedback provided by the transmit-receive histotripsy transducer array can overcome the two main limitations of the ultrasound imaging feedback as described earlier.
3) Treatment monitoring—Cavitation dynamics are correlated to the level of tissue damage generated by histotripsy. The received ACE signals can be processed to monitor the treatment progress and determine the completion of the treatment in real-time. The 3D cavitation mapping can also be co-registered or overlaid onto a pre-treatment MRI or CT scan.
4) Compact system—The transmit-receive histotripsy array system can be compact and of similar size of a transmit-only histotripsy system, but with many added features as described above. The transmit-receive histotripsy array can be used independent of and/or supplemental to the ultrasound imaging that is currently used for histotripsy feedback.
5) Automatic registration—The map of cavitation generated by the transducer receive is automatically registered to the therapy side coordinate system. The treatment accuracy then only relies on a single registration between therapy transducer and treatment planning imaging.

Methods of Use

The transmit—receive ultrasound systems described herein can enable ultrasound and/or histotripsy therapy that provides general amplitude aberration correction to make therapy more efficient, and can further provide corrections for focal shift. These methods are described below:

General Amplitude Aberration Correction

Methods of providing general amplitude aberration correction during ultrasound therapy are provided. These methods can include transmitting ultrasound pulses into a single test pulse location (e.g., the center of the planned treatment volume aligned with the target tissue), and receiving time delays from the single location. Next, the received time delays can be used as a representative aberration correction map for the entire planned treatment volume (e.g., all treatment pattern locations within the planned treatment volume). Aberration correction can then be applied to subsequent ultrasound treatment pulses to increase efficiency of the therapy.

In some examples, multiple discrete test pulse locations can be used (e.g., seven-point test locations). The method can include receiving time delays at each test location/position and modeling the received delays to interpolate the aberration correction map for the entire planned treatment volume.

Alternatively, the method can include real-time testing. For example, the method can include using received signals for aberration correction at each test pulse and treatment location and updating the aberration correction in real-time during therapy.

In some examples, test pulse sequences can be different than therapy pulses (automated treatment) to afford smaller clouds or more thermally favorable sequences to assess aberration/threshold, before transitioning to therapy pulses.

Correcting for Focal Shift

During ultrasound/histotripsy therapy, it is common to see a focal shift, typically along the "Z" axis and mostly due to the difference of sound speed in water (coupling medium) and tissue. This can typically be corrected for in the ultrasound system by visualizing the bubble cloud with an imaging system (e.g., ultrasound imaging). As described herein, the receive capability of the system can be used to map the reflection signals from the water-skin interface to determine the time-of-flight from each element surface to the water-skin interface, and use that time-of-flight determination to correct for the focal shift caused by the coupling medium.

To build and expand upon this method, other inputs can be used to make the prediction of focal shift more accurate. For example, focal shift correction can be based on a single test pulse at (e.g., at the center of the planned treatment volume), or based on multiple test-pulses interpolated over the volume.

The receive data received by the system can be registered with imaging data from an imaging system to provide more visual feedback regarding cavitation. Additionally, the receive and imaging data can be registered with the robotic positioning arm of the therapy system so the image/receive data is in context to the six degrees of freedom of the positioning arm.

The methods described above can be used to correct for focal shift/aberration when the imaging system is obscured (such as when the focal zone is behind bone or another aberrator).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A transmit-receive driving electronics for a histotripsy system, comprising:

at least one transducer element configured to transmit ultrasound pulses to generate cavitation at a focal location in a transmit mode and receive ultrasound reflections and/or acoustic cavitation emissions in a receive mode;

a current sense resistor configured to measure a current in the transmit-receive driving electronics during the receive mode; and a bypass circuit electrically coupled to the at least one transducer element and the current sense resistor, wherein the bypass circuit is configured to be switched on during the transmit mode to bypass the current sense resistor and switched off during the receive mode to allow the sense resistor to measure the current.

2. The transmit-receive driving electronics of claim 1, further comprising:

a drive transformer electrically coupled to the at least one transducer element.

3. The transmit-receive driving electronics of claim 1, wherein the bypass circuit further comprises a pair of bypass diodes.

4. The transmit-receive driving electronics of claim 1, wherein the bypass circuit further comprises a pair of bypass transistors.

5. The transmit-receive driving electronics of claim 1, further comprising an analog-to-digital converter (ADC) configured to process the ultrasound reflections.

6. The transmit-receive driving electronics of claim 5, wherein the ADC is coupled to the sense resistor with a transformer.

7. The transmit-receive driving electronics of claim 1, further comprising a field-programmable gated array (FPGA) device configured to control the transmit mode and the receive mode.

8. The transmit-receive driving electronics of claim 1, further comprising one or more processors configured to calculate a travel time of ultrasound pulses from the at least one transducer element to the cavitation.

9. The transmit-receive driving electronics of claim 8, wherein the one or more processors are configured to adjust a transmission time delay for the at least one transducer element based on the calculated travel time such that all ultrasound pulses transmitted by the histotripsy system arrive at the focal location simultaneously.

10. The transmit-receive driving electronics of claim 1, further comprising one or more processors configured to:

detect a selected acoustic cavitation emissions feature; and evaluate a change in the selected acoustic cavitation emissions feature over time.

11. The transmit-receive driving electronics of claim 10, wherein the one or more processors are further configured to correlate the change in the selected acoustic cavitation emissions feature to treatment progression.

12. The transmit-receive driving electronics of claim 10, wherein the one or more processors are further configured to correlate the change in the selected acoustic cavitation emissions feature to treatment completion.

13. The transmit-receive driving electronics of claim 10, wherein the selected acoustic cavitation emission feature comprises one or more timings of cavitation expansion bubble signals.

14. The transmit-receive driving electronics of claim 10, wherein the selected acoustic cavitation emission feature comprises one or more amplitudes of cavitation expansion bubble signals.

15. The transmit-receive driving electronics of claim 10, wherein the selected acoustic cavitation emission feature comprises one or more collapse signals of the cavitation.

16. The transmit-receive driving electronics of claim 10, wherein the selected acoustic cavitation emission feature comprises one or more rebound signals of the cavitation.

* * * * *